US010561651B2

(12) United States Patent
Lim et al.

(10) Patent No.: US 10,561,651 B2
(45) Date of Patent: Feb. 18, 2020

(54) METHODS FOR TREATING NEUROBLASTOMA

(71) Applicants: IGNYTA, INC., San Diego, CA (US); Nerviano Medical Sciences S.r.I., Nerviano (MI) (IT)

(72) Inventors: Jonathan Lim, San Diego, CA (US); Elena Ardini, Sesto san Giovanni (IT); Maria Menichincheri, Milan (IT)

(73) Assignees: IGNYTA, INC., San Diego, CA (US); NERVIANO MEDICAL SCIENCES, S.R.L., Nerviano (MI) (IT)

( * ) Notice: Subject to any disclaimer, the term of this patent is extended or adjusted under 35 U.S.C. 154(b) by 0 days.

(21) Appl. No.: 16/050,516

(22) Filed: Jul. 31, 2018

(65) Prior Publication Data
US 2018/0333412 A1 Nov. 22, 2018

Related U.S. Application Data

(63) Continuation of application No. 15/114,367, filed as application No. PCT/EP2015/053544 on Feb. 19, 2015, now abandoned.

(60) Provisional application No. 62/069,999, filed on Oct. 29, 2014, provisional application No. 62/055,450, filed on Sep. 25, 2014, provisional application No. 62/052,994, filed on Sep. 19, 2014, provisional application No. 61/942,287, filed on Feb. 20, 2014.

(51) Int. Cl.
A61K 31/496 (2006.01)

(52) U.S. Cl.
CPC .................................. *A61K 31/496* (2013.01)

(58) Field of Classification Search
None
See application file for complete search history.

(56) References Cited

U.S. PATENT DOCUMENTS

| 4,555,402 | A | 11/1985 | Matsuda et al. |
|---|---|---|---|
| 7,015,231 | B2 | 3/2006 | Lackey et al. |
| 7,230,098 | B2 | 6/2007 | Cui et al. |
| 7,534,792 | B2 | 5/2009 | Wittman et al. |
| 7,790,756 | B2 | 9/2010 | Flynn et al. |
| 7,799,782 | B2 | 9/2010 | Munson et al. |
| 7,964,592 | B2 | 6/2011 | Garcia-Echeverria et al. |
| 8,114,865 | B2 | 2/2012 | Bandiera et al. |
| 8,114,989 | B2 | 2/2012 | Wang et al. |
| 8,299,057 | B2 * | 10/2012 | Lombardi Borgia ........... C07D 231/56 514/210.21 |
| 8,372,858 | B2 | 2/2013 | Michellys et al. |
| 8,404,846 | B2 | 3/2013 | Claridge et al. |
| 8,497,284 | B2 | 7/2013 | Bannen et al. |
| 8,513,263 | B2 | 8/2013 | Haas et al. |
| 8,673,893 | B2 | 3/2014 | Lombardi Borgia et al. |
| 8,680,111 | B2 | 3/2014 | Bailey et al. |
| 9,102,662 | B2 | 8/2015 | Lombardi Borgia et al. |
| 10,085,979 | B2 | 10/2018 | Hornby et al. |
| 10,231,965 | B2 | 3/2019 | Lim et al. |
| 2004/0014802 | A1 | 1/2004 | Dutruc-Rosset et al. |
| 2005/0014829 | A1 | 1/2005 | Remenar et al. |
| 2009/0263397 | A1 | 10/2009 | Buck et al. |
| 2010/0197665 | A1 | 8/2010 | Bandiera et al. |
| 2013/0018036 | A1 | 1/2013 | Lombardi Borgia et al. |
| 2014/0107107 | A1 | 4/2014 | Gautschi et al. |
| 2015/0051222 | A1 | 2/2015 | Barbugian et al. |
| 2015/0283132 | A1 | 10/2015 | Lim et al. |
| 2017/0007599 | A1 | 1/2017 | Lim et al. |
| 2017/0065582 | A1 | 3/2017 | Hornby et al. |
| 2018/0177792 | A1 | 6/2018 | Wei |
| 2018/0333412 | A1 | 11/2018 | Lim et al. |
| 2019/0000840 | A1 | 1/2019 | Li et al. |
| 2019/0022089 | A1 | 1/2019 | Codallos et al. |
| 2019/0070173 | A1 | 3/2019 | Hornby et al. |

FOREIGN PATENT DOCUMENTS

| CN | 101594862 | 12/2009 |
|---|---|---|
| CN | 101754956 | 6/2010 |
| CN | 102924479 A | 2/2013 |
| IT | WO2013/174876 | * 11/2013 |
| JP | 2002-275068 A | 9/2002 |
| WO | WO-99/43302 A1 | 9/1999 |
| WO | WO-03/051847 A1 | 6/2003 |
| WO | WO-03/078403 A2 | 9/2003 |
| WO | WO-2004/007676 | 1/2004 |
| WO | WO-2004/022544 A1 | 3/2004 |
| WO | WO-2004/062662 A1 | 7/2004 |
| WO | WO-2004/075898 A1 | 9/2004 |
| WO | WO-2005/040413 A1 | 5/2005 |
| WO | WO-2006/003276 A1 | 1/2006 |
| WO | WO-2006/080450 A1 | 8/2006 |
| WO | WO-2006/111035 A1 | 10/2006 |

(Continued)

OTHER PUBLICATIONS

Brodeur et al. in Clinical Cancer Research 15(10), 3244-3250 (2009) (Year: 2009).*
Adriaenssens, E. et al., Nerve growth factor is a potential therapeutic target in breast cancer, Cancer Res, Jan. 15, 2008, 68(2):346-351.
Albaugh, P. et al., Discovery of GNF-5837, a selective TRK inhibitor with efficacy in rodent cancer tumor models, Med. Chem. Lett, 2012, 3:140-145.
Alecensa® (alectinib) capsules, for oral use, Prescribing Information, Dec. 2015, 16 pp.
Asaumi, K. et al., Expression of neurotrophins and their receptors (TRK) during facture healing, Bone, Jun. 2000, 26(6);625-633.
Awad et al., "ALK inhibitors in non-small cell lung cancer: crizotinib and beyond", Clin Adv Hemotol Oncol, Jul. 2014, 12(7):429-439.
Bardelli, A. et al., Mutational analysis of the tyrosine kinome in colorectal cancers, Science, 2003, 300:949.

(Continued)

*Primary Examiner* — Dennis Heyer
(74) *Attorney, Agent, or Firm* — Foley & Lardner LLP

(57) ABSTRACT

Methods of treating neuroblastoma associated with a deregulated protein kinase activity are disclosed. The treatment may include administration of substituted indazole derivatives of formula (I) or formula 2.(I) and pharmaceutically acceptable salts therefor, as degined in the specification.

8 Claims, 1 Drawing Sheet

(56) References Cited

FOREIGN PATENT DOCUMENTS

| WO | WO-2007/017497 A2 | 2/2007 |
|---|---|---|
| WO | WO-2007/075847 A2 | 7/2007 |
| WO | WO-2008/003396 A1 | 1/2008 |
| WO | WO-2008/073480 A1 | 6/2008 |
| WO | WO-2008/074749 A1 | 6/2008 |
| WO | WO-2009/013126 A1 | 1/2009 |
| WO | WO-2013/119950 A2 | 8/2013 |
| WO | WO-2013/174876 A1 | 11/2013 |
| WO | WO-2014/093750 A1 | 6/2014 |
| WO | WO-2015/124697 A1 | 8/2015 |
| WO | WO-2015/189814 A1 | 12/2015 |
| WO | WO-2016/089760 A1 | 6/2016 |
| WO | WO-2016/089853 A1 | 6/2016 |
| WO | WO-2017/106492 A1 | 6/2017 |
| WO | WO-2019/077506 | 4/2019 |

OTHER PUBLICATIONS

Bardelli, A. et al., Mutational analysis of the tyrosine kinome in colorectal cancers, Science, 2003, 300:949; Supplemental Material.
Baserga, R. et al., The IGF-I receptor in cell growth, transformation and apoptosis, Biochip Biophys Acta, 1997, 1332:F105-F126.
Bavetsias, V. et al., Hit generation and exploration: imidazo[4,5-b]pyridine derivatives as inhibitors of aurora kinases, Bioorganic & Medicinal Chemistry Letters, 2007, 17:6567-6571.
Bergethon, K. et al., ROS1 rearrangements define a unique molecular class of lung cancers, Journal of Clinical Oncology, Mar. 10, 2012, 30(8):863-870.
Bouhana, K. et al., LOXO-101, a pan TRK inhibitor, for the treatment of TRK-driven cancers, 26th EORTC-NCI-AACR Symposium on Molecular Targets and Cancer Therapeutics, Barcelona, Spain, Poster, Nov. 2014, Abstract #291, 1 p.
Brodeur, G. M., Neuroblastoma: biological insights into a clinical enigma, Nat. Rev. Cancer, Mar. 2003, 3:203-216.
Brodeur, GM, et al. Trk receptor expression and inhibition in neuroblastomas. Clin Cancer Res. May 15, 2009;15(10):3244-50.
Broekman, F. et al., Tyrosine kinase inhibitors: multi-targeted or single-targeted?, World J. Clin Oncol, Feb. 10, 2011, 2(2):80-93.
Brose, M. et al., LOXO-101, a selective pan-TRK inhibitor for patients with TRK-alterations 15th International Thyroid Congress, Oct. 2015, Lake Buena Vista, Florida, Poster, 1 p.
Brzezianska, E. et al., Rearrangements of NTRK1 oncogene in papillary thyroid carcinoma, Neuroendocrinology Letters, 2007, 28(3):221-229.
Burris, H. A., III. et al., A first-in-human study of LOXO-101, a highly selective inhibitor of the tropomyosin receptor kinase (TRK) family, American Society of Clinical Oncology (ASCO) 2015 Annual Meeting, May-Jun. 2015, Chicago, IL, Poster, 1 p.
Calvo, E., Posters Discussion: Developmental Therapeutics, 2014 ESMO Congress, Sep. 26-30, 2014, 21 pp.
Cho, H. et al., Expression of mRNA for brain-derived neurotrophic factor in the dorsal root ganglion following peripheral inflammation, Brain Research, 1997, 749:358-362.
ClinicalTrials.gov, Aug. 20, 2014, A phase 1/2a study of oral RXDX-101 in adult patients with locally advanced or metastatic cancer; study targeting ALK, ROS1 or TRKA/8/C (STARTRK:1), 4 pp.
ClinicalTrials.gov, Aug. 2014, A phase 1/2a study of oral RXDX-101 in adult patients with locally advanced or metastatic cancer; study targeting ALK, ROS1 or TRKA/8/C, 36 pp.
ClinicalTrials.gov, Sep. 11, 2014, A phase 1/2a study oforal RXDX-101 in adult patients with locally advanced or metastatic cancer; study targeting ALK, ROS1 or TRKA/8/C (STARTRK-1), 7 pp.
Cohen, P., Protein kinases—the major drug targets of the twenty-first century?, Nature Reviews, Apr. 2002, Drug Discovery 1:309-315.
Cohen, P., The development and therapeutic potential of protein kinase inhibitors, Current Opinion in Chemical Biology, 1999, 3:459-465.
Collymore, D. C. et al., Genomic testing in oncology to improve clinical outcomes while optimizing utilization: the evolution of diagnostic testing, American Journal of Managed Care, Feb. 2016, 22(2):S20-S28.
Croucher et al., "TrkB inhibition by GNF-4256 slows growth and enhances chemotherapeutic efficacy in neuroblastoma xenografts", Cancer Chemother Pharmacol, 2015, 75:131-141.
Dang, C. et al., Expression of nerve growth factor receptors is correlated with progression and prognosis of human pancreatic cancer, Journal of Gastroenterology and Hepatology, 2006, 21(5):850-858.
Davidson, B. et al., Expression and activation of the nerve growth factor receptor TrkA in serous ovarian carcinoma, Clin. Cancer Res., Jun. 2003, 9:2248-2259.
Davies, K. D. et al., Resistance of ROS1 inhibition mediated by EGFR pathway activation in non-small cell lung cancer, PlOS ONE, Dec. 2013, 8(12):e82236.
Davies, K. et al., Identifying and targeting ROS1 gene fusions in non-small cell lung cancer, Clin Cancer Res, Sep. 1, 2012, 18(17):4570-4579.
De Braud, F. et al., 2014, Phase 1 open label, dose escalation study of RXDX-101, an oral pan-trk, ROS1, and ALK inhibitor, in patients with advanced solid tumors with relevant molecular alterations, Poster, 1P.
De Braud, F. et al., 2014, RXDX-101, an oral pan-TRK, POS1, and ALK inhibitor, in patients with advanced solid tumors with relevant molecular alterations, Annals of Oncology 25(Supplement 4): iv146-iv164 (abstract).
De Braud, F., 2014, Phase 1 open label, dose escalation study of RXDX-101, an oral pan-trk, ROS1, and ALK inhibitor, in patients with advanced solid tumors with relevant molecular alterations, PowerPoint presentation, ASCO 50th Annual Meeting, 18 pp.
De Melo-Jorge, M. et al., The chagas' disease parasite trypanosoma cruzi exploits nerve growth factor receptor TrkA to infect mammalian hosts, Cell Host & Microbe, Jun. 2007, 1(4):251-261.
Delafoy, L. et al., Role of nerve growth factor in the trinitrobenzene sulfonic acid-induced colonic hypersensitivity, Pain, 2003, 105:489-497.
Di Mola, F. F. et al., Nerve growth factor and Trk high affinity receptor (TrkA)gene expression in inflammatory bowel disease, Gut, 2000, 46(5):670-678.
Dionne, C. A. et al., Cell cycle-independent death of prostate adenocarcinoma is induced by the trk tyrosine kinase inhibitor CEP-751 (KT6587), Clin. Cancer Res., Aug. 1998, 4(8):1887-1898.
Doebele, R. C. et al., An oncogenic NTRK fusion in a patient with soft-tissue sarcoma with response to the tropomyosin-related kinase inhibitor LOXO-101, Cancer Discovery, Oct. 2015, 1049-1057.
Dou, Y. et. al., 2006, Increased nerve growth factor and its receptors in atopic dermatitis: an immunohistochemical study, Archives of Dermatological Research, 2008, 298(1):31-37.
Drug Class Detail: TRK Receptor Inhibitor (Pan); https://ckb.jax.org/drugClass/show?drugClassId=Trk Receptor Inhibitor %28Pan%29: (Jul. 16, 2014).
Duffy, M. J. et al., Companion biomarkers: paving the pathway to personalized treatment for cancer, Clinical Chemistry, 2013, 59(1):1447-1456.
Evans et al., "Antitumor Activity of CEP-751 (KT-6587) on Human Neuroblastoma and Medulloblastoma Xenografts", American Association for Cancer Research, 1999, 5:3594-3602.
Freund-Michel, V. et al., The nerve growth factor and its receptors in airway inflammatory diseases, Pharmacology & Therapeutics, 2008, 117(1):52-76.
Gainor, Justin, MD,RXDX-101 & RXDX-102, PowerPoint Presentation, Feb. 20, 2014, 13 pp.
Greco, A. et al., Rearrangement of NKRK1 gene in papillary thyroid carcinoma, Molecular and Cellular Endocrinology, May 1, 2010, 321(1):44-49.
Hansen, K. et al., Autophagic cell death induced by TrkA receptor activation in human glioblastoma cells, Journal of Neurochemistry, 2007, 103:259-275.
Hofmann, F. et al., Blocking insulin-like growth factor-I receptor as a strategy for targeting cancer, Drug Discov Today, Aug. 2005, 10(15):1041-1047.

(56) References Cited

OTHER PUBLICATIONS

Hu, V. Y. et al., Decrease in bladder overactivity with ren1820 in rats with cyclophosphamide induced cystitis, The Journal of Urology, 2005, 173(3):1016-1021.

Hu, Y. et al., Identification of brain-derived neurotrophic factor as a novel angiogenic protein in multiple myeloma, Cancer Genetics and Cytogenetics, 2007, 178:1-10.

Ignyta Inc., Aug. 12, 2014, Ignyta announces second quarter 2014 company highlights and financial results, Press Release, 4 pp.

Ignyta Inc., Dec. 3, 2013, Ignyta announces completion of $54 million in private placements to catalyze precision medicine for cancer patients, Press Release, 2 pp.

Ignyta Inc., Feb. 20, 2014, Ignyta announces preliminary data from RXDX-101 phase I clinical trial, Press Release, 2 pp.

Ignyta Inc., Feb. 27, 2014, Ignyta announces of IND for RXDX-101, Press Release, 2 pp.

Ignyta Inc., Feb. 28, 2014, Ignyta announces 2013 company highlights and full year financial results, Press Release, 5 pp.

Ignyta Inc., Jul. 21, 2014, Ignyta announces initiation of STARTKR-1 global phase I/II clinical trial of RXDX-101, Press Release, 2 pp.

Ignyta Inc., May 31, 2014, Ignyta announces interim data from RXDX-101 phase I clinical trial, Press Release, 2 pp.

Ignyta Inc., May 7, 2014, Ignyta announces RXDX-101 phase I data abstract accepted for oral presentation at the 2014 ASCO annual meeting, Press Release, 2 pp.

Ignyta Inc., Nov. 1, 2013, Ignyta completes merger and announces license agreement for the development of two leading tyrosine kinase inhibitors, Press Release, 1 p.

Ignyta Inc., Nov. 18, 2014, Ignyta announces RXDX-101 phase 1 presentations at the 2014 EORTC-NCI-AACR 'molecular targets and cancer therapeutics' conference, Press Release, 2 pp.

Ignyta Inc., Nov. 7, 2014, Ignyta announces third quarter 2014 company highlights and financial results, Press Release, 5 pp.

Ignyta Inc., Sep. 15, 2014, Ignyta announces RXDX-101 phase 1 data presentation at the 2014 ESMO Congress, Press Release, 2 pp.

Ignyta Inc., Sep. 28, 2014, Ignyta announces interim data from RXDX-101 phase I clinical trial at 2014 ESMO Congress, Press Release, 2 pp.

Ignyta, Feb. 2014, Catalyzing precision medicine with integrated Rx/Ox in oncology, presentation, 23 pp.

Ignyta, Inc., Feb. 20, 2014, Form 8-K (Current Report Filing), 20 pp.

Ignyta, Inc., Jan. 13, 2014, Form 8-K (Current Report Filing), 28 pp.

Ignyta, Inc., Jun. 2, 2014, Form 8-K (Current Report Filing), 26 pp.

Ignyta, Inc., May 12, 2014, Form 8-K (Current Report Filing), 11 pp.

Ignyta, Inc., May 2, 2014, Form 8-K (Current Report Filing), 4 pp.

Ignyta, Inc., Nov. 7, 2014, Form 8-K (Current Report Filing), 13 pp.

Ignyta, Inc., Oct. 14, 2014, Form 8-K (Current Report Filing), 61 pp.

Isaacson, Jerry, Ph.D. et al., "Ignyta, Inc.: Initiation of Coverage," LifeSci Advisors Research, Feb. 14, 2014, pp. 1-37.

Iyer et al., "AZ64 inhibits TrkB and enhances the efficacy of chemotherapy and local radiation in neuroblastoma xenografts", Cancer Chemother Pharmacol, 2012, 70:477-486.

Iyer et al., "Lestaurtinib Enhances the Antitumor Efficacy of Chemotherapy in Murine Xenograft Models of Neuroblastoma", Clin Cancer Res; 2010; 16(5):1478-1485.

Jaggar, S. I. et al., Inflammation of the rat urinary bladder is associated with a referred thermal hyperalgesia which is nerve growth factor dependent, Br. J. Anaesth., 1999, 83:442-448.

Jantzen, G. M. et al., "Sustained- and controlled-release drug delivery systems", in Banker et al. eds., Modern Pharmaceutics, 1996, 3rd Ed. pp. 575-609, Marcel Dekker, Inc., New York, NY.

Johnson, T. W. et al., Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a macrocyclic inhibitor of anaplastic lymphoma kinase (ALK) and c-ros oncogene 1(ROS1) with preclinical brain exposure and broad-spectrum potency against ALK-resistant mutations, Journal of Medicinal Chemistry, 2014, 57(11);4720-4744.

Karaman, M. W. et al., A quantitative analysis of kinase inhibitor selectivity, Nature Biotechnology, Jan. 2008, 26(1):127-132.

Khandwala, H. M. et al., The effects of insulin-like growth factors on tumorigenesis and neoplastic growth, Endocr Rev, 2000, 21(3):215-244.

Kruettgen, A. et al., The dark side of the NGF family: neurotrophins in neoplasias, Brain Pathology, 2006, 16:304-310.

Kushner, BH, et al. Irinotecan plus temozolomide for relapsed or refractory neuroblastoma. J Clin Oncol. Nov. 20, 2006;24(33):5271-6.

Lamant et al., 2000, Expression of the ALK tyrosine kinase gene in neuroblastoma, American Journal of Pathology, 156:1711-1721.

Lamb et al., Nerve growth factor and gastric hyperalgesia in the rat, Neurogastroenterol. Motil, 2003, 15:355-361.

Laron, Z., Laron syndrome (primary growth hormone resistance or insensitivity): the personal experience 1958-2003, J Clin Endocrinol Metab, 2004, 89(3):1031-1044.

Le Roith et al., The somatomedin hypothesis: 2001, Endocr Rev, 2001, 22(1):53-74.

Lee, J. et al., Identification of ROS1 rearrangement in gastric adenocarcinoma, Cancer, May 1, 2013, 119:1627-1635.

Li, Q. et al., Brain derived neurotrophic factor (BDNF) contributes to the pain hypersensitivity following surgical incision in the rats, Molecular Pain, 2008, 4:27, 11 pp.

Li, T. et al., Genotyping and genomic profiling of Non-Small-Cell lung cancer: implications for current and future therapies, Journal of Clinical Oncology, Mar. 10, 2013, vol. 31, No. 8, pp. 1039-1049.

Lindeman, N. I., MD et al., Molecular testing guideline for selection of lung cancer patients for EGFR and ALK tyrosine kinase inhibitors, Journal of Thoracic Oncology, Jul. 2013, 8(7):823-859.

Lipska, B. S. et al., c.1810C>T polymorphism of NTRK1 gene is associated with reduced survival in neuroblastoma patients, BMC Cancer, Biomed Central, Dec. 13, 2009, London, GB, 9(1):436.

Ma, Q. et al., The progressive tactile hyperalgesia induced by peripheral inflammation is nerve growth factor dependent, Neuroreport, 1997, 8(4):807-810.

Marchetti, A. et al., Frequent mutations in the neurotrophic tyrosine receptor kinase gene family in large cell neuroendocrine carcinoma of the lung, Human Mutation, 2008, 29(5):609-616.

Marsilje, T. H. et al., Synthesis, structure-activity relationships and in vivo efficacy of the novel potent and selective anaplastic lymphoma kinase (ALK) inhibitor LDK378 currently in phase 1 and 2 clinical trials, J. Med. Chem., 2013, 56:5675-5690 and Supporting Information.

Matayoshi, S. et al., Actions of brain-derived neurotrophic factor on spinal nociceptive transmission during inflammation in the rat, J. Physiol., 2005, 569(2):685-695.

McMahon, S. B. et al., The biological effects of endogenous nerve growth factor on adult sensory neurons revealed by a trkA-IgG fusion molecule, Nat. Med., Aug. 1995, 1(8):774-780.

Meyer, J. et al., Remarkable leukemogenic potency and quality of a constitutively active neurotrophin receptor, ΔTrkA, Leukemia, 2007, 21:2171-2180.

Milkeiwicz, K. L. et al., Inhibitors of anaplastic lymphoma kinase: a patent review, Expert Opin. Ther. Patents, 2010, 20(12):1653-1681.

Minturn et al, "Phase I trial of lestaurtinib for children with refractory neuroblastoma: a new approaches to neuroblastoma therapy consortium study," Cancer Chemother Pharmacol, Feb. 22, 2011, 9 pages.

Molina-Vila, M. A. et al., Impact of the new EGF receptor and ALK testing guideline on personalized lung cancer medicine, Personalized Medicine, 2013, 19(5):415-417.

Murphy et al., "Monitoring activity of RXDX-101 in Phase 1/2 patients using a pharmacodynamics assay for TrkA activation", European Journal of Cancer, Poster Session—Molecular Targeted Agents II, 2014, 50(6):143-144.

Nakagawara et al.; "Association between high levels of expression of the Trk gene and favorable outcome in human neuroblastoma"; N Engl J Med; 1993; 328:847-54.

(56) References Cited

OTHER PUBLICATIONS

Nakagawara, A., Trk receptor tyrosine kinases: a bride between cancer and neural development, Cancer Letters, 2001, 169:107-114.
National Comprehensive Cancer Network, NCCN Clinical Practice Guidelines in Oncology: Non-small cell lung cancer, Apr. 2016, Version 4.2016. 169 pp.
Okimoto, R. A. et al., Recent advances in personalized lung cancer medicine, Personalized Medicine, 2014, 11(3):309-321.
Patapoutian, A. et al., Trk receptors: mediators of neurotrophin action, Current Opinion in Neurobiology, 2001, 11:272-280.
PCT International Search Report and Written Opinion for Application No. PCT/US2015/062975, dated Feb. 12, 2016, 16 pages.
PCT International Preliminary Report on Patentability (Chapter 1) for Application No. PCT/US2015/062975 dated Jun. 15, 2017.
PCT International Search Report for international application No. PCT/EP2015/053544 dated Mar. 30, 2015.
PCT Written Opinion of the International Searching Authority for Application No. PCT/EP2015/053544 dated Aug. 27, 2015. (6 pages).
Perez-Pinera,P. et al., The Trk tyrosine kinase inhibitor K252a regulates growth on lung adenocarcinomas, Molecular and Cellular Biochemistry, 2007, 295:19-26.
Pierotti, A. et al., Oncogenic rearrangements of the NRTK1/NGF receptor, Cancer Letters, 2006, 232:90-98.
Pinski, J. et al., Trk receptor inhibition induced apoptosis of proliferating but not quiescent human osteoblasts, Cancer Research, Feb. 15, 2002, 62:986-989.
Puig De La Bellacasa, R. et al., ALK and ROS1 as a joint target for the treatment of lung cancer: a review, Translational Lung Cancer Research, 2013, vol. 2, No. 2, pp. 72-86.
Raychaudhuri, S. P. et al., K252a, a high-affinity nerve growth factor receptor blocker, improves psoriasis: an in vivo study using the severe combined immunodeficient mouse-human skin model, Journal of Investigative Dermatology, Mar. 3, 2004, 122(3);812-819.
Sakamoto, H. et al., CH5424802, a selective ALK inhibitor capable of blocking the resistant gatekeeper mutant, Cancer Cell, 2011, 19:679-690.
Shaw, A. T. et al., Crizotinib versus chemotherapy in advanced ALK-positive lung cancer, The New England Journal of Medicine, Jun. 30, 2013, 268(25):2385-2394.
Shaw, A. T. et al., Targeting anaplastic lymphoma kinase in lung cancer, Clin. Cancer Res., 2011, 17:2081-2086.
Shelton, D. et al., Nerve growth factor mediates hyperalgesia and cachexia in auto-immune arthritis, Pain, 2005, 116:8-16.
Sohrabji, F. et al., Estrogen-BDNF interactions: implications for neurodegenerative diseases, Neuroendocrinology, 2006, 27(4):404-414.
Stumpfova, M. et al., Zeroing in on ROS1 rearrangements in non-small cell lung cancer, Clin Cancer Res, Aug. 2, 2012, 18(16):4222-4224.
Tatematsu, T. et al., Investigation of neurotrophic tyrosine kinase receptor 1 fusions and neurotrophic tyrosine kinase receptor family expression in non-small-cell lung cancer and sensitivity to AZD7451 in vitro, Molecular and Clinical Oncology, 2014, 2:725-730.
Thompson S. W. N. et al., Brain-derived neurotrophic factor is an endogenous modulator of nociceptive responses in the spinal cord, Proc. Natl. Acad. Sci. USA, Jul. 1999, 96:7714-7718.
Tremodar PI-2, Highlights or Prescribing Information, 2014. (17 pages).
Truzzi, F. et al., Neurotrophins and their receptors stimulate melanoma cell proliferation and migration, Journal of Investigative Dermatology, 2008, 128(8):2031-2040.
Tzelepi, V., Editorial: Personalized cancer treatment, Current Molecular Pharmacology, 2014, 7(1), 2 pp.
U.S. Office Action for U.S. Appl. No. 14/623,904 dated Oct. 16, 2015. (10 pages).
U.S. Office Action for U.S. Appl. No. 14/623,904 dated Feb. 4, 2016. (8 pages).
U.S. Office Action for U.S. Appl. No. 14/623,904 dated Jun. 7, 2016. (14 pages).
U.S. Office Action for U.S. Appl. No. 14/623,904 dated Sep. 16, 2016. (12 pages).
U.S. Office Action for U.S. Appl. No. 14/623,904 dated Dec. 9, 2016. (16 pages).
U.S. Office Action for U.S. Appl. No. 14/623,904 dated Apr. 28, 2017. (18 pages).
U.S. Office Action for U.S. Appl. No. 14/623,904 dated Nov. 3, 2017. (19 pages).
U.S. Office Action for U.S. Appl. No. 14/623,904 dated Mar. 26, 2018. (12 pages).
U.S. Office Action for U.S. Appl. No. 14/953,969 dated Feb. 24, 2017. (8 pages).
U.S. Office Action for U.S. Appl. No. 14/953,969 dated Oct. 2, 2017. (21 pages).
U.S. Notice of Allowance for U.S. Appl. No. 14/953,969 dated May 2, 2018. (10 pages).
U.S. Office Action for U.S. Appl. No. 15/114,367 dated Jan. 30, 2017. (7 pages).
U.S. Office Action for U.S. Appl. No. 15/114,367 dated Jun. 15, 2017. (12 pages).
U.S. Office Action for U.S. Appl. No. 15/114,367 dated Feb. 2, 2018. (21 pages).
Vaishnavi, A. et al., Oncogenic and drug sensitive NTRK1 rearrangements in lung cancer, Nat Med., Nov. 2013, 19(11):1469-1472.
Valent, A. et al. Mapping of the tyrosine kinase receptors trkA (NTRK1), trkB (NTRK2) and trkC(NTRK3) to human chromosomes 1q22, 9q22 and 15q25 by fluorescence in situ hybridization. Eur.J. Hum. Genet (1997), vol. 5(2), pp. 102-104.
Valentinis, B. et al., IGF-I receptor signaling in transformation and differentiation, 2001, Mol Pathol, 54:133-137.
Voskoglou-Nomikos, T. et al., Clinical predictive value of the in vitro cell line, human xenograft, and mouse allograft preclinical cancer models, Clinical Cancer Research, Sep. 15, 2003, 9:4227-4239.
Wang, Y. et al., Insulin-like growth factor receptor-1 as an anticancer target: blocking transformation and inducing apoptosis, Curr Cancer Drug Targets, 2002, 2:191-207.
Warner, S. et al., Targeting aurora-2 kinase in cancer, Molecular Cancer Therapeutics, Jun. 3, 2003, 2:589-595.
Weroha, S. J. et al., IFG-1 receptor inhibitors in clinical trials-early lessons, J. Mammary Gland Biol. Neoplasia, 2008, vol. 13, pp. 471-483.
Wolff, M.E., Burger's Medicinal Chemistry and Drug Discovery, 5th Ed. vol. 1, 1995, pp. 975-977, John Wiley & Sons, Inc., New York, NY.
Wood et al., "Somatic Mutations of GUCY2F, EPHA3, and NTRK3 in Human Cancers", Human Mutation in Brief #923, 2006. (9 pages).
Woolf, C. J. et al., Letter to Neuroscience: Nerve growth factor contributes to the generation of inflammatory sensory hypersensitivity, Neuroscience, 1994, vol. 62, No. 2, pp. 327-331.
Xalkori® (crizotinib) capsules, for oral use, Prescribing Information, Mar. 2016, 27 pp.
Zahn, P. et al., Effect of blockade of nerve growth factor and tumor necrosis factor on pain behaviors after plantar incision, J. Pain, vol. 5 No. 3, Apr. 2004, pp. 157-163.
Zhu, L., et al. Implications of tropomyosin-related kinase B (TrkB) in head and neck cancer. Anticancer Res. Sep.-Oct. 2007;27(5A):3121-6.
Zykadia™ (ceritinib) capsules, for oral use, Prescribing Information, Apr. 2014, 16 pp.
A. Greco et al, "Rearrangements of NTRK1 gene in papillary thyroid carcinoma," Molecular and Cellular Endocrinology, (May 2010), vol. 321, No. 1, ISSN 0303-7207, pp. 44-49.
Aveic et al., "Study of pan-Trk, ROS1, ALK inhibitor, RXDX-101, activity on human neuroblastoma cell lines", Brochure, SIOPEN Annual Meeting 2014, Apr. 23-25, 2014. (1 page).
Drilon et al., "Safety and Antitumor Activity of the Multitargeted Pan-TRK, ROS1, and ALK Inhibitor Entrectinib: Combined Results from Two Phase I Trials (ALKA-372-001 and STARTRK-1)", Published OnlineFirst Feb. 9, 2017, Downloaded from cancerdiscovery. aacrjournals.org on Apr. 7, 2017, pp. 401-409.

(56) References Cited

OTHER PUBLICATIONS

Estrada-Bernal et al., "TRK kinase domain mutations that induce resistance to a pan-TRK inhibitor", [abstract]. In: Proceedings of the AACR-NCI-EORTC International Conference: Molecular Targets and Cancer Therapeutics; Nov. 5-9, 2015; Boston, MA. Philadelphia (PA): AACR; Mol Cancer Ther 2015;14(12 Suppl 2):Abstract nr C65.

Gad et al., "Neurotrophic activities of trk receptors conserved over 600 million years of evolution", J. Neurobiol., 2004;60(1):12-20.

Iannone et al., "Increased expression of nerve growth factor (NGF) and high affinity NGF receptor (p140 TrkA) in human osteoarthritic chondrocytes", Rheumatology, 2002;41:1413-1418.

International Search Report and Written Opinion issued in PCT/IB2018/058031 dated Feb. 12, 2019.

Iyer et al., "Abstract 5390: The TRK Inhibitor RXDX-101 enhances the efficacy of temozolomide and irinotecan in a xenograft model of neuroblastoma," Cancer Research, Aug. 1, 2015, vol. 75, Iss. 15, Supplement, p. 5390.

Lee et al., "Mechanisms of Constitutive Activation of Janus Kinase 2-V617F Revealed at the Atomic Level Through Molecular Dynamics Simulations 1," Cancer, vol. 115, No. 8, pp. 1692-1700 (2009).

Lewis et al., "The Discovery and Optimization of a Novel Class of Potent, Selective, and Orally Bioavailable Anaplastic Lymphoma Kinase (ALK) Inhibitors with Potential Utility for the Treatment of Cancer", Journal of Medicinal Chemistry, 2012;55(14): 6523-6540.

Li et al., "Abstract A173: Potent anti-tumor activity of entrectinib in patient-derived models harboring oncogenic gene rearrangements of NTRKs," Molecular Cancer Therapeutics, (2015), 14(12):Supplement 2, p. A173.

Omura et al., "A New Alkaloid AM-2282 of Streptomyces Origin Taxonomy, Fermentation, Isolation and Preliminary Characterization", Journal of Antibiotics, 1977, 30(4):275-282.

Pardue et al., "Nucleic Acid Hybridization. A practical approach", IRL Press, Oxford Washington/DC. 1985:170-203.

PCT International Preliminary Report on Patentability (Chapter II) for Application No. PCT/US2016/066919, dated Dec. 7, 2017. (22 pages).

PCT International Search Report and Written Opinion dated Apr. 21, 2017 in PCT Patent Application No. PCT/US2016/066919.

Russo et al., "Acquired Resistance to the TRK Inhibitor Entrectinib in Colorectal Cancer," Cancer Discovery, (2016), 6:36-44.

Uniprot Accession P04629. "NTRK1_human", (Jun. 24, 2015), available on the internet: http://www.uniprot.org/uniprot/P04624.txt?version=204 (12 pages).

Vasconcelos et al., "Solid dispersions a strategy to improve oral bioavailability of poor water soluble drug," Drug Discovery Today, vol. 12, Jan. 2012, pp. 1068-1075.

Wei et al., "Abstract 2136: Entrectinib is effective against the gatekeeper and other emerging resistance mutations in NTRK-, ROS1- and ALK-rearranged cancers", [abstract], Proceedings: AACR 107th Annual Meeting 2016; Apr. 16-20, 2016: New Orleans, LA; 2016;76(14 Suppl):Abstract nr 2136.

Zhu et al., "Nerve Growth Factor Expression Correlates With Perineural Invasion and Pain in Human Pancreatic Cancer", Journal of Clinical Oncology, 1999;17:2419-2428.

Iyer, R., et al., "Entrectinib is a potent inhibitor of TRK-driven neuroblastomas in a xenograft mouse model," Cancer Letters 372 (2016) pp. 179-186, http://dx.doi.org/10.1016/j.canlet.2016.01.018.

Nakagawara, A., et al., "Expression and Function of TRK-B and BDNF In Human Neuroblastomas," Molecular and Cellular Biology, vol. 14, No. 1, Jan. 1994 p. 759-767.

* cited by examiner

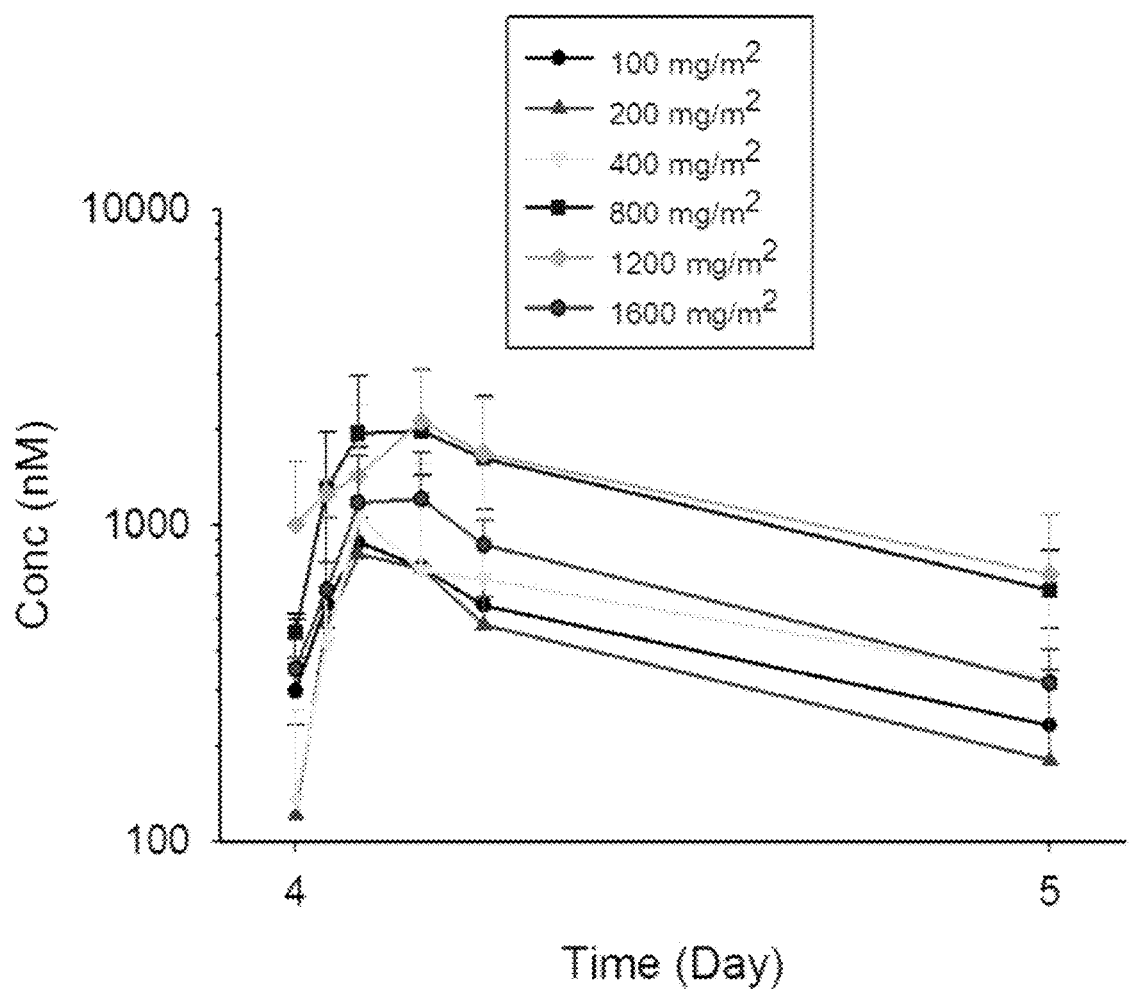

METHODS FOR TREATING NEUROBLASTOMA

CROSS-REFERENCE TO RELATED APPLICATIONS

This application is a continuation of U.S. patent application Ser. No. 15/114367, filed Jul. 26, 2016; which is a National Stage Entry of PCT International Application No. PCT/EP2015/053544, filed Feb. 19, 2015, which claims the benefit of U.S. Provisional Application Nos. 61/942287, filed on Feb. 20, 2014; 62/052994, filed on Sep. 19, 2014; 62/055450, filed on Sep. 25, 2014; and 62/069999, filed on Oct. 29, 2014; each of which is incorporated herein by reference in its entirety; including any drawings.

PARTIES OF JOINT RESEARCH AGREEMENT

The compositions and methods disclosed herein are subject to a joint research agreement between Ignyta, Inc. and Nerviano Medical Sciences s.r.l., executed Oct. 10, 2013.

FIELD OF THE INVENTION

The present invention relates to certain substituted indazole compounds, which modulate the activity of protein kinases. The compounds of this invention are therefore useful in treating diseases caused by deregulated protein kinase activity. The present invention also provides methods for preparing these compounds, pharmaceutical compositions comprising these compounds, and methods of treating diseases utilizing pharmaceutical compositions comprising these compounds.

BACKGROUND OF THE INVENTION

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3:459-465.

A subset of PK is a group of membrane receptors with intrinsic protein-tyrosine kinase activity (RPTK). Upon binding of grow factors, RPTKs become activated and phosphorylate themselves and a series of substrates in the cytoplasm. Through this mechanism, they can transduce intracellular signalings for proliferation, differentiation or other biological changes. Structural abnormalities, overexpression and activation of RTPKs are frequently observed in human tumors, suggesting that constitutive ignition of the signal transduction leading to cell proliferation can result in malignant transformation. Anaplastic lymphoma kinase (ALK) is a tyrosine kinase receptor belonging to the insulin receptor subfamily of RTKs: the ALK gene is located on chromosome 2 and is expressed mainly in neuronal cells, especially during development. The ALK gene is involved in a balanced chromosomal translocation with the Nucleophosmin (NPM) gene on chromosome 5 in a large subset of Anaplastic Large Cell Lymphomas (ALCL). In the ALK+ ALCL, as a result of the translocation, the NPM ubiquitous promoter drives an ectopic expression of the fusion protein in which the NPM moiety dimerizes and the ALK kinase domain undergoes auto-phosphorylation and becomes constitutively active.

Many data from the literature have demonstrated that the NPM-ALK fusion protein has a strong oncogenic potential and its ectopic expression is responsible for cellular transformation. Moreover, the constitutive expression of human NPM-ALK in mouse T-cell lymphocytes is sufficient for the development of lymphoid neoplasia in transgenic animals with a short period of latency.

ALCL is a defined disease characterized by the surface expression of the CD30 antigen (Ki-1), and accounts for 2% of adult and 13% of pediatric non -Hodgkin's lymphomas, affecting predominantly young male patients. ALK+ALCL accounts for 70% of all ALCLs and is an aggressive disease with systemic signs, and frequent extranodal involvement (bone marrow, skin, bone, soft tissues).

About 15-20% of ALK-expressing ALCLs were found to bear a different chromosomal translocation, involving the cytoplasmic portion of ALK, with different N-terminal moieties, all resulting in constitutive activation of the ALK kinase domain.

Moreover, cell lines established from solid tumors of ectodermal origin like melanomas, breast carcinomas, as well as neuroblastomas, glioblastomas, Ewings sarcomas, retinoblastomas, were found to express the ALK receptor.

ROS1 belongs to the insulin-receptor superfamily. Like other tyrosine kinase receptor molecules, it plays a role in relaying growth signals from the environment outside the cell into the cell's nucleus. It is 1 of 2 orphan receptor tyrosine kinase family members with no known binding ligand. Genetic changes in ROS1, such as gene rearrangements, mutations, or copy number increases, create oncogenes, which can lead to cancer (Stumpfova and Janne, 2012). ROS1 was discovered in NSCLC patients in the form of a fusion protein (6 different partners for ROS1) and is found in approximately 2% of patients with NSCLC (Bergethon et al., 2012; Davies et al, 2012). Two other ROS1 gene rearrangements have been detected in a variety of other cancers, including glioblastoma multiforme, cholangiocarcinoma, ovarian cancer, gastric adenocarcinoma, colorectal cancer, inflammatory myofibroblastic tumor, angiosarcoma, and epitheloid hemangioendothelioma (Lee et al., 2013; Davies and Doebele, 2013; Davies, et al., 2012; Shaw et al., 2013).

ROS1 gene rearrangements create fusion proteins with constitutively active kinase domains that activate downstream signaling pathways leading to oncogenic properties in cells, including uncontrolled proliferation and resistance to cell death with prolonged tumor cell survival. These pathways include Ras-ERK for cellular proliferation and the JAK-STAT and PI3K/AKT pathways, which regulate cell survival (anti-apoptosis) and proliferation. ROS1 fusion proteins may also activate the mTOR pathway, which is critical for the regulation of protein translation. Cancers that have these pathways activated tend to be more aggressive, with invasion and metastasis leading to poor survival of the patients (Davies and Doebele, 2013).

Trk's are the high affinity receptor tyrosine kinases activated by a group of soluble growth factors called neurotrophins (NT). The Trk receptor family has three members--TrkA, TrkB and TrkC. Among the neurotrophins are (i)

nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., Current Opinion in Neurobiology, 2001, 11, 272-280). NTRK1 encodes the TrkA receptor tyrosine kinase. TrkA activates the PI3K/AKT, PKC and ERKI/2 pathways which promote cell growth and survival.

Inhibitors of the Trk/neurotrophin pathway have been demonstrated to be effective in numerous pre-clinical animal models of pain. For example, antagonistic NGF and TrkA antibodies (for example, RN-624) have been shown to be efficacious in inflammatory and neuropathic pain animal models and in human clinical trials (Woolf, C. J. et al. (1994) Neuroscience 62, 327-331; Zahn, P. K. et al. (2004) J. Pain 5, 157-163; McMahon, S. B. et al., (1995) Nat. Med. 1, 774-780; Ma, Q. P. and Woolf, C. J. (1997) Neuroreport 8, 807-810; Shelton, D. L. et al. (2005) Pain 116, 8-16; Delafoy, L. et al. (2003) Pain 105, 489-497; Lamb, K. et al. (2003) Neurogastroenterol. Motil. 15, 355-361; Jaggar, S. 1. et al. (1999) Br. J. Anaesth. 83, 442-448). Additionally, recent literature indicates after inflammation, BDNF levels and TrkB signaling is increased in the dorsal root ganglion (Cho, L. et al. Brain Research 1997, 749, 358) and several studies have show antibodies that decrease signaling through the BDNF/TrkB pathway inhibit neuronal hypersensitization and the associated pain (Chang-Qi, L et al. Molecular Pain 2008, 4:27).

In addition, it has been shown that tumor cell sand tumor invading macrophages directly stimulates TrkA located on peripheral pain fibers. Using various tumor models in both mice and rats it was demonstrated that neutralizing NGF with a monoclonal antibody inhibits cancer related pain to a degree similar or superior to the highest tolerated dose of morphine. In addition, activation of the BDNF/TrkB pathway has been implicated in numerous studies as a modulator of various types of pain including inflammatory pain (Matayoshi, S., J. Physiol. 2005, 569:685-95), neuropathic pain (Thompson, S. W., Proc. Natl. Acad. Sci. USA 1999, 96:7714-18) and surgical pain (Li, C. -Q. et al., Molecular Pain, 2008, 4(28), 1-11). Because TrkA and TrkB kinases may serve as a mediator of NGF driven biological responses, inhibitors of TrkA and/or other Trk kinases may provide an effective treatment for chronic pain states.

Recent literature has also shown that overexpression, activation, amplification and/or mutation of Trk's are associated with many cancers including neuroblastoma (Brodeur, G. M., Nat. Rev. Cancer 2003, 3, 203-216), ovarian cancer (Davidson. B., et al., Clin. Cancer Res. 2003, 9, 2248-2259), breast cancer (Kruettgen et al, Brain Pathology 2006, 16: 304-310), prostate cancer (Dionne et al, Clin. Cancer Res. 1998, 4(8): 1887-1898), pancreatic cancer (Dang et al, Journal of Gastroenterology and Hepatology 2006, 21(5): 850-858), multiple myeloma (Hu et al, Cancer Genetics and Cytogenetics 2007, 178: 1-10), astrocytoma and medulloblastoma (Kruettgen et al, Brain Pathology 2006, 16: 304-310) glioma (Hansen et al, Journal of Neurochemistry 2007, 103: 259-275), melanoma (Truzzi et al, Journal of Investigative Dermatology 2008, 128(8): 2031-2040, thyroid carcinoma (Brzezianska et al, Neuroendocrinology Letters 2007, 28(3), 221-229.), lung adenocarcinoma (Perez-Pinera et al, Molecular and Cellular Biochemistry 2007, 295(1& 2), 19-26), large cell neuroendocrine tumors (Marchetti et al, Human Mutation 2008, 29(5), 609-616), and colorectal cancer (Bardelli, A., Science 2003, 300, 949). In preclinical models of cancer, Trk inhibitors are efficacious in both inhibiting tumor growth and stopping tumor metastasis. In particular, non-selective small molecule inhibitors of Trk A, B and C and Trk/Fc chimeras were efficacious in both inhibiting tumor growth and stopping tumor metastasis (Nakagawara, A. (2001) Cancer Letters 169:107-114; Meyer, J. et al. (2007) Leukemia, 1-10; Pierottia, M. A. and Greco A., (2006) Cancer Letters 232:90-98; Eric Adriaenssens, E. et al. Cancer Res (2008) 68:(2) 346-351) (Truzzi et al, Journal of Investigative Dermatology 2008, 128(8): 2031-2040. Therefore, an inhibitor of the Trk family of kinases is expected to have utility in the treatment of cancer.

Various gene rearrangements of the Trk gene have been implicated in human malignancies. For example, the MPRIP-NRTK1 and CD74-NRTK1 gene rearrangements have been implicated in the development of non-small cell lung cancer. Gene rearrangements TPM3-NRTK1, TGF-NTRKI and TPR-NTRK1 have been implicated in the development of papillary thyroid cancer. The TPM3-NTRK1 gene rearrangement has been implicated in the development of colorectal cancer. NTRKI, NTRK2 or NTRK3 gene rearrangements have also been identified in glioblastoma, AML and secretory breast cancer. In 2013, Vaishnavi et al. reported novel NTRK1 fusions in 3/91 pan-negative patients with lung adenocarcinoma using NGS and FISH (Vaishnavi et al. Nat Med. 2013 Nov:19(11):1469-72).

In addition, inhibition of the neurotrophin/Trk pathway has been shown to be effective in treatment of pre-clinical models of inflammatory diseases. For example, inhibition of the neurotrophin/Trk pathway has been implicated in pre-clinical models of inflammatory lung diseases including asthma (Freund-Michel, V; Frossard, N.; Pharmacology & Therapeutics (2008), 117(1), 52-76), interstitial cystitis (Hu Vivian Y; et. al. The Journal of Urology (2005), 173(3), 1016-21), inflammatory bowel diseases including ulcerative colitis and Crohn's disease (Di Mola, F. F, et. al., Gut (2000), 46(5), 670-678) and inflammatory skin diseases such as atopic dermatitis (Dou, Y. -C.; et. al. Archives of Dermatological Research (2006), 298(1), 31-37), eczema and psoriasis (Raychaudhuri, S. P.; et. al. Journal of Investigative Dermatology (2004), 122(3), 812-819).

The neurotrophin/Trk pathway, particularly BDNF/TrkB, has also been implicated in the etiology of neurodegenerative diseases including multiple sclerosis, Parkinson's disease and Alzheimer's disease (Sohrabji, Farida; Lewis, Danielle K. Frontiers in Neuroendocrinology (2006), 27(4), 404-414). Modulation of the neutrophin/Trk pathway may have utility in treatment of these and related diseases.

The TrkA receptor is also thought to be critical to the disease process in the infection of the parasitic infection of Typanosoma cruzi (Chagas disease) in human hosts (de Melo-Jorge, M. et al. Cell Host & Microbe (2007), 1(4), 251-261). Thus, TrkA inhibition my have utility in treating Chagas disease and related protozoan infections.

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer (1) and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA and TrkC receptors has been observed in the bone forming area in mouse models of bone fracture (K. Asaumi, et al., Bone (2000) 26(6) 625-633). In addition, localization of NGF was observed in almost all bone forming cells (K. Asaumi, et al.). Recently, it was demonstrated that a pan-Trk inhibitor inhibits the tyrosine signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

In conclusion, interfering with ALK or ROS1 signaling likely represents a specific and effective way to block tumor cell proliferation in ALCL and possibly other indications. The insulin-like growth factor 1 receptor (IGF-1R, IGF1R) is also a member of the insulin receptor subfamily of RTKs.

In addition, interfering with TrkA, TrkB and/or TrkC signaling, or a combination thereof, represents a specific and effective way to block tumor cell proliferation in various cancers, including, but not limited to, non-small cell lung cancer, papillary thyroid cancer, neuroblastoma, pancreatic cancer and colorectal cancer.

There exist several lines of evidence suggesting that IGF-1R signaling can contribute to tumorigenesis, and that interfering with IGF-1R function represents a valid therapeutic option in cancer. For an overview of IGFs and IGF-1R signaling, physiological function, and detailed description of the evidence supporting involvement of this system in human cancer that is summarized above, as well as in other pathologies, the reader is directed to the many reviews on the subject and references contained therein, for example Baserga R. et al, Biochim Biophys Acta vol. 1332, pages F105-F126, 1997; Khandwala H. M. et al, Endocr Rev vol. 21, pages 215-44, 2000; Le Roith D. et al, Endocr Rev vol. 22, pages 53-74, 2001; Valentinis B. et al, Mol Pathol vol. 54, pages 133-7, 2001; Wang Y. et al, Curr Cancer Drug Targets vol. 2, pages 191-207, 2002; Laron, Z. J Clin Endocrinol Metab vol. 89, pages 1031-1044, 2004; Hofmann F et al, Drug Discov Today vol. 10, pages 1041-7, 2005.

SUMMARY OF THE INVENTION

3-Amino and 3-acylamino indazole derivatives for the treatment of neurodegenerative diseases, cerebrovascular accidents, obesity, cardiovascular diseases and cancer are disclosed in WO2006003276, WO2004022544 and WO 2003078403 in the name of Aventis Pharma SA.

Indazolylamide derivatives for the treatment of diabetes, neurodegenerative conditions such as Alzheimer's disease and Parkinson's disease are disclosed in WO2003051847 in the name of SmithKline Beecham P.L.C.

Indazole derivatives for the treatment of tumor disease, viral disease, immunosuppression in transplantation, cystic fibrosis and diseases associated with angiogenesis are disclosed in WO2008003396 in the name of Merck GMBH.

Despite these developments, there is still a need for more effective agents for the treatment of such diseases.

We have now discovered that a series of indazoles are potent protein kinase inhibitors and are thus useful in anticancer therapy.

Accordingly, an object of the present invention is to provide a substituted indazole compound represented by formula (I), or formula 2.(I).

More particularly, a first object of the present invention is to provide a substituted indazole compound represented by formula (I),

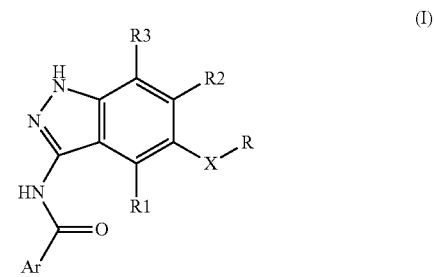

wherein: •X is p13 CH2—, —CH(OH)—, —CH(OR')— or —C(R'R")—, wherein: ○R' is an optionally further substituted straight or branched C1-C6 alkyl and R" is hydrogen or an optionally further substituted straight or branched C1-C6 alkyl; •Ar is aryl or heteroaryl optionally substituted with one or more substituents independently selected from halogen, C2-C6 alkenyl, C2-C6 alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted straight or branched C1-C6 alkyl, C3-C6 cycloalkyl, heterocyclyl, aryl and heteroaryl, wherein: ○R4 is hydrogen, C2-C6 alkenyl, C2-C6 alkynyl, NR5R6, OR7, SR7, R8R9N—C1-C6 alkyl, R8O—C1-C6 alkyl, an optionally further substituted straight or branched C1-C6 alkyl, C3-C6 cycloalkyl, heterocyclyl, aryl or heteroaryl; R5 and R6 are independently hydrogen, C2-C6 alkenyl, C2-C6 alkynyl, R8R9N—C2-C6 alkyl, R8O—C2-C6 alkyl, an optionally further substituted straight or branched C1-C6 alkyl, C3-C6 cycloalkyl, heterocyclyl, aryl or heteroaryl, or R5 and R6, taken together with the nitrogen atom to which they are bonded, may form an optionally substituted heterocyclyl group;

○R7 is hydrogen, C2-C6 alkenyl, C2-C6 alkynyl, COR4, SOR10, SO2R10, R8R9N—C2-C6 alkyl, R8O—C2-C6 alkyl, an optionally further substituted straight or branched C1-C6 alkyl, C3-C6 cycloalkyl, heterocyclyl, aryl or heteroaryl, wherein R4 is as defined above;

○R8 and R9 are independently hydrogen, C2-C6 alkenyl, C2-C6 alkynyl, COR4, an optionally further substituted straight or branched C1-C6 alkyl, C3-C6 cycloalkyl, heterocyclyl, aryl or heteroaryl, or R8 and R9, taken together with the nitrogen atom to which they are bonded, may form an optionally substituted heterocyclyl group, wherein R4 is as defined above;

○R10 is hydrogen, C2-C6 alkenyl, C2-C6 alkynyl, NR5R6, OR7, R8R9N—C1-C6 alkyl, R8O—C1-C6 alkyl, an optionally further substituted straight or branched C1-C6 alkyl, C3-C6 cycloalkyl, heterocyclyl, aryl or heteroaryl, wherein R5, R6, R7, R8 and R9 are as defined above;

•R is an optionally substituted straight or branched C1-C6 alkyl, C3-C6 cycloalkyl, heterocyclyl, aryl or heteroaryl;

•R1, R2 and R3 are independently hydrogen, halogen, nitro, an optionally substituted straight or branched C1-C6 alkyl, NR5R6, or OR7, wherein R5, R6 and R7 are as defined above; or isomers, tautomers, prodrugs or pharmaceutically acceptable salt thereof.

Several indazole derivatives useful for the therapy of a variety of diseases such as cancer, neurodegenerative, cardiovascular, metabolic and of the central nervous system, have been disclosed in WO2007075847 in the name of Takeda Pharmaceutical, in WO2006003276, WO2004062662, WO2004022544 and WO2003078403 all in the name of Aventis, in WO2006080450 in the name of Kyowa Hakko Kogyo and in WO2006003276 in the name of University of Connecticut.

Despite these developments, there is still need for effective agents for said diseases. The present inventors have now discovered that compounds of formula 2.(I), described below, are kinase inhibitors and are thus useful in therapy as antitumor agents.

More particularly, a second object of the present invention is to provide a substituted indazole compound represented by formula 2.(I),

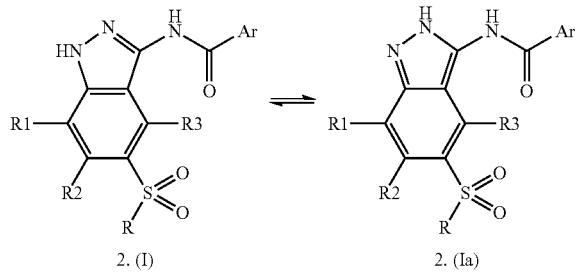

Wherein Ar is aryl optionally substituted with one or more substituents independently selected from halogen, alkenyl, alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted straight or branched C1-C6 alkyl, C3-C6 cycloalkyl, heterocyclyl and aryl, wherein:

R4 is hydrogen, alkenyl, alkynyl, NR5R6, OR7, SR7, R8R9N—C1-C6 alkyl, R8O—C1-C6 alkyl, an optionally further substituted straight or branched C1-C6 alkyl, C3-C6 cycloalkyl, heterocyclyl or aryl;

R5 and R6 are independently hydrogen, alkenyl, alkynyl, R8R9N—C2-C6 alkyl, R8O—C2-C6 alkyl, an optionally further substituted straight or branched C1-C6 alkyl, C3-C6 cycloalkyl, heterocyclyl or aryl, or R5 and R6, taken together with the nitrogen atom to which they are bonded, may form an optionally substituted heterocyclyl group;

R7 is hydrogen, alkenyl, alkynyl, COR4, SOR10, SO2R10, R8R9N—C2-C6 alkyl, R8O—C2-C6 alkyl, an optionally further substituted straight or branched C1-C6 alkyl, C3-C6 cycloalkyl, heterocyclyl or aryl, wherein R4 is as defined above;

R8 and R9 are independently hydrogen, alkenyl, alkynyl, COR4, an optionally further substituted straight or branched C1-C6 alkyl, C3-C6 cycloalkyl, heterocyclyl or aryl, or R8 and R9, taken together with the nitrogen atom to which they are bonded, may form an optionally substituted heterocyclyl group, wherein R4 is as defined above;

R10 is hydrogen, alkenyl, alkynyl, NR5R6, OR7, R8R9N—C1-C6 alkyl, R8O—C1-C6 alkyl, an optionally further substituted straight or branched C1-C6 alkyl, C3-C6 cycloalkyl, heterocyclyl or aryl, wherein R5, R6, R7, R8 and R9 are as defined above; R is an optionally further substituted straight or branched C1-C6 alkyl, C3-C6 cycloalkyl, heterocyclyl or aryl; R1, R2 and R3 are independently hydrogen, halogen, nitro, an optionally further substituted straight or branched C1-C6 alkyl, NR5R6 or OR7, wherein R5, R6 and R7 are as defined above; and pharmaceutically acceptable salt thereof.

The present invention also provides a method for treating diseases caused by and/or associated with deregulated protein kinase activity, particularly PLK family, protein kinase C in different isoforms, Met, PAK-4, PAK-5, ZC-1, STLK-2, DDR -2, Aurora 1, Aurora 2, Bub-1, Chk1, Chk2, HER2, raf1, MEK1, MAPK, EGF-R, PDGF-R, FGF-R, FLT3, JAK2, IGF-R, ALK, PI3K, weel kinase, Src, Abl, Akt, MAPK, ILK, MK-2, IKK-2, Cdc7, Nek, Cdk/cyclin kinase family, more particularly Aurora 2, IGF-1R and ALK activity, and ROS1 activity, and further more particularly ALK activity and/or ROS1 activity, which comprises administering to a mammal in need thereof an effective amount of a substituted indazole compound represented by formula (I) or formula 2.(I) as defined above.

Some embodiments of the present invention are to treat a disease caused by and/or associated with dysregulated protein kinase activity selected from the group consisting of cancer and cell proliferative disorders.

Some embodiments of the present invention, are to treat specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, angiosarcoma, glioblastoma, holangiocarcinoma, inflammatory myofibroblastic tumor, epitheloid hemangioendothelioma, astrocytoma, meningioma, angiosarcoma, epitheloid hemangiothelioma, keratocanthomas, thyroid follicular cancer, Kaposi's sarcoma, and Pancreatic cancer.

Some embodiments of the present invention, are to treat specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, Pancreatic cancer, and medulloblastoma.

Some embodiments of the present invention, are to treat ALK+ Anaplastic Large Cell Lymphomas (ALCL) and possibly other indications in which the ALK activity might play a role, like Neuroblastoma, Rhabdomyosarcoma, Glioblastoma, Inflammatory Myofibroblastic Tumor, and some kind of Melanomas, Breast Carcinomas, Ewings sarcomas, Retinoblastomas and Non Small Cell Lung Carcinomas (NSCLC).

Some embodiments of the present invention, are to treat, reduce the symptoms of, ameliorate the symptoms of, delay the onset of, or otherwise pharmaceutically address Pancreatic cancer and possibly other indications in which a defect in the modulation of ROS1 activity, or upregulation, misregulation or deletion thereof might play a role by administering a molecule of Formula (I) as disclosed herein, such as N-[5-(3,5-difluorobenzyl)-1H-indazol-3-yl]-4-(piperazin-1-yl)-2-(tetrahydro-2H -pyran-4-ylamino) benzamide or N-[5-(3,5-difluorobenzyl)-1H-indazol-3-yl]-4-(4-methyl -piperazin-1-yl)-2-(tetrahydro-2H-pyran-4-ylamino) benzamide.

Some embodiments of the present invention, are to treat, reduce the symptoms of, ameliorate the symptoms of, delay the onset of, or otherwise pharmaceutically address Pancreatic cancer and possibly other indications in which a defect in the modulation of ROS1 activity, or upregulation, misregulation or deletion thereof might play a role by administering a molecule disclosed in U.S. Pat. No. 8,299,057, such as N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methylpiperazin-1-yl)-2-(tetrahydro-2H-pyran-4-ylamino) benzamide, which patent issued Oct. 30, 2012, the entirety of which is hereby incorporated by reference. Some embodiments of the present invention, are to treat, reduce the symptoms of, ameliorate the symptoms of, delay the onset of, or otherwise pharmaceutically address Pancreatic cancer and possibly other indications in which a defect in the modulation of ROS1 activity, or upregulation, misregulation or deletion thereof might play a role by administering a molecule disclosed in U.S. Pat. No. 8,114,865, such as N-[5-(3,5-difluoro-benzenesulfonyl)-1H-indazol-3-yl]-2-((R)-2-methoxy-1-methyl-ethylamino)-4-(4-methyl-piperazin-1-yl) benzamide, which patent issued Feb. 14, 2012, the entirety of which is hereby incorporated by reference.

Some embodiments of the present invention, are to treat, reduce the symptoms of, ameliorate the symptoms of, delay the onset of, or otherwise pharmaceutically address Pancreatic cancer and possibly other indications in which a defect in the modulation of ALK, ROS1, TrkA, TrkB, or TrkC activity, or a combination thereof, or upregulation, misregulation or deletion thereof might play a role by administering a molecule disclosed in U.S. Pat. No. 8,299,057, such as N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H-pyran-4-ylamino) benzamide, which patent issued Oct. 30, 2012, the entirety of which is hereby incorporated by reference. Some embodiments of the present invention, are to treat, reduce the symptoms of, ameliorate the symptoms of, delay the onset of, or otherwise pharmaceutically address Pancreatic cancer and possibly other indications in which a defect in the modulation of ALK, ROS1, TrkA, TrkB, or TrkC activity, or a combination thereof, or upregulation, misregulation or deletion thereof might play a role by administering a molecule disclosed in U.S. Pat. No. 8,114,865, such as N-[5-(3,5-difluoro-benzenesulfonyl)-1H-indazol-3-yl]-2-(R)-2-methoxy-1-methyl-ethylamino)-4-(4-methyl-piperazin-1-yl) benzamide, which patent issued Feb. 14, 2012, the entirety of which is hereby incorporated by reference.

In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1 activity, or upregulation, misregulation or deletion thereof might play a role by administering a molecule which is N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H -pyran-4-ylamino) benzamide. In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1 activity, or upregulation, misregulation or deletion thereof might play a role by administering a molecule which is N-[5-(3,5-difluorobenzyl)-1H- indazol-3-yl]-4-(piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1 activity, or upregulation, misregulation or deletion thereof might play a role by administering a molecule which is N-[5-(3,5-difluorobenzyl)-1H-indazol-3-yl]-4-(4-methyl-piperazin-1-yl)-2-(tetrahydro-2H-pyran-4-ylamino) benzamide.

In some embodiments, methods of the present invention are to treat, reduce the symptoms of, ameliorate the symptoms of, delay the onset of, or otherwise pharmaceutically address Pancreatic cancer and possibly other indications in which a defect in the modulation of ALK, ROS1, TrkA, TrkB, or TrkC activity, or a combination thereof, or upregulation, misregulation or deletion thereof might play a role by administering a molecule of U.S. Pat. No. 8,299,057, issued Oct. 30, 2012, the entirety of which is hereby incorporated by reference. In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1, TrkA, TrkB, or TrkC activity, or a combination thereof, activity, or upregulation, misregulation or deletion thereof might play a role by administering a molecule of U.S. Pat. No. 8,114,865, issued Feb. 14, 2012, the entirety of which is hereby incorporated by reference.

In some embodiments, methods of the present invention are treat, reduce the symptoms of, ameliorate the symptoms of, delay the onset of, or otherwise pharmaceutically address Pancreatic cancer and possibly other indications in which a defect in the modulation of ROS1, TrkA, TrkB, or TrkC activity, or a combination thereof, activity, or upregulation, misregulation or deletion thereof might play a role by administering a molecule which is N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1, TrkA, TrkB, or TrkC activity, or a combination thereof, activity, or upregulation, misregulation or deletion thereof might play a role by administering a molecule which is N-[5-(3,5-difluorobenzyl)-1H-indazol-3-yl]-4-(piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1, TrkA, TrkB, or TrkC activity, or a combination thereof, activity, or upregulation, misregulation or deletion thereof might play a role by administering a molecule which is N-[5-(3,5-difluorobenzyl)-1H-indazol-3-yl]-4-(4-methyl-piperazin-1-yl)-2-(tetrahydro-2H-pyran-4-ylamino) benzamide.

In some embodiments, methods of the present invention are to treat, reduce the symptoms of, ameliorate the symptoms of, delay the onset of, or otherwise pharmaceutically address Pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an individual, and administering to the individual a molecule of Formula (I) as disclosed herein, such as N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-

(tetrahydro-2H-pyran-4-ylamino) benzamide. In some embodiments, methods of the present invention are to treat, reduce the symptoms of, ameliorate the symptoms of, delay the onset of, or otherwise pharmaceutically address Pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an individual, and administering to the individual a molecule which is N-[5-(3,5-difluorobenzyl)-1H-indazol-3-yl]-4-(piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address Pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an individual, and administering to the individual a molecule which is N-[5-(3,5-difluorobenzyl)-1H-indazol-3-yl]-4-(4-methyl-piperazin-1-yl)-2-(tetrahydro-2H-pyran-4-ylamino) benzamide.

In some embodiments, methods of the present invention are to treat, reduce the symptoms of, ameliorate the symptoms of, delay the onset of, or otherwise pharmaceutically address Pancreatic cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an individual, and administering to the individual a molecule of Formula (I) as disclosed herein, such as N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H-pyran-4-ylamino) benzamide.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an individual comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an individual comprises assaying for ROS1 transcript accumulation in an RNA population from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an individual comprises determining the nucleic acid sequence such as the genomic deoxyribonucleic acid sequence in a cell or cells or a cell population comprising a cell or cells from a pancreatic cancerous or precancerous cell population.

In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an individual comprises assaying for ALK, ROS1, TrkA, TrkB, or TrkC activity in a cell extract from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an individual comprises assaying for ALK, ROS1, TrkA, TrkB, or TrkC transcript accumulation in an RNA population from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an individual comprises determining the nucleic acid sequence such as the genomic deoxyribonucleic acid sequence in a cell or cells or a cell population comprising a cell or cells from a pancreatic cancerous or precancerous cell population.

In some embodiments, methods of the present invention are to treat, reduce the symptoms of, ameliorate the symptoms of, delay the onset of, or otherwise pharmaceutically address Pancreatic cancer and possibly other indications in which a defect in the modulation of ALK, ROS1, TrkA, TrkB, or TrkC activity, or a combination thereof, or upregulation, misregulation or deletion thereof might play a role by administering a molecule of U.S. Pat. No. 8,299,057, issued Oct. 30, 2012, the entirety of which is hereby incorporated by reference. In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1, TrkA, TrkB, or TrkC activity, or a combination thereof, activity, or upregulation, misregulation or deletion thereof might play a role by administering a molecule of U.S. Pat. No. 8,114,865, issued Feb. 14, 2012, the entirety of which is hereby incorporated by reference.

In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1, TrkA, TrkB, or TrkC activity, or a combination thereof, activity, or upregulation, misregulation or deletion thereof might play a role by administering a molecule which is N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1, TrkA, TrkB, or TrkC activity, or a combination thereof, activity, or upregulation, misregulation or deletion thereof might play a role by administering a molecule which is N-[5-(3,5-difluorobenzyl)-1H-indazol-3-yl]-4-(piperazin-1-yl)-2-(tetrahydro-2H-pyran-4-ylamino)

benzamide. In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1, TrkA, TrkB, or TrkC activity, or a combination thereof, activity, or upregulation, misregulation or deletion thereof might play a role by administering a molecule which is N-[5-(3,5-difluorobenzyl)-1H-indazol-3-yl]-4-(4-methyl-piperazin-1-yl)-2-(tetrahy dro-2H-pyran-4-ylamino) benzamide.

In some embodiments, methods of the present invention are to treat, reduce the symptoms of, ameliorate the symptoms of, delay the onset of, or otherwise pharmaceutically address Pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an individual, and administering to the individual a molecule of Formula (I) as disclosed herein, such as N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address Pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an individual, and administering to the individual a molecule which is N-[5-(3,5-difluorobenzyl)-1H-indazol-3-yl]-4-(piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address Pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an individual, and administering to the individual a molecule which is N-[5-(3,5-difluorobenzyl)-1H-indazol-3-yl]-4-(4-methyl-piperazin-1-yl)-2-(tetrahydro-2H-pyran-4-ylamino) benzamide.

In some embodiments, methods of the present invention are to treat, reduce the symptoms of, ameliorate the symptoms of, delay the onset of, or otherwise pharmaceutically address Pancreatic cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an individual, and administering to the individual a molecule of Formula (I) as disclosed herein, such as N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H-pyran-4-ylamino) benzamide.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an individual comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an individual comprises assaying for ROS1 transcript accumulation in an RNA population from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an individual comprises determining the nucleic acid sequence such as the genomic deoxyribonucleic acid sequence in a cell or cells or a cell population comprising a cell or cells from a pancreatic cancerous or precancerous cell population.

In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an individual comprises assaying for ALK, ROS1, TrkA, TrkB, or TrkC activity in a cell extract from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an individual comprises assaying for ALK, ROS1, TrkA, TrkB, or TrkC transcript accumulation in an RNA population from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an individual comprises determining the nucleic acid sequence such as the genomic deoxyribonucleic acid sequence in a cell or cells or a cell population comprising a cell or cells from a pancreatic cancerous or precancerous cell population.

In some embodiments, methods of the present invention are to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ALK, ROS1, TrkA, TrkB, or TrkC activity, or a combination thereof, or upregulation, misregulation or deletion thereof might play a role by administering a molecule of U.S. Pat. No. 8,299,057, issued Oct. 30, 2012, the entirety of which is hereby incorporated by reference. In some embodiments, methods of the present invention are to treat, reduce the symptoms of, ameliorate the symptoms of, delay the onset of, or otherwise pharmaceutically address Pancreatic cancer and possibly other indications in which a defect in the modulation of ROS1, TrkA, TrkB, or TrkC activity, or a combination thereof, activity, or upregulation, misregulation or deletion thereof might play a role by administering a molecule of U.S. Pat. No. 8,114,865, issued Feb. 14, 2012, the entirety of which is hereby incorporated by reference.

In some embodiments, methods of the present invention are to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a molecule which is N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a molecule which is N-[5-(3,5-difluorobenzyl)-1H-indazol-3-yl]-4-(piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a molecule which is N-[5-(3,5-difluorobenzyl)-1H-indazol-3-yl]-4-(4-methyl-piperazin-1-yl)-2-(tetrahydro-2H-pyran-4-ylamino) benzamide.

In some embodiments, methods of the present invention are to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an individual, and administering to the individual a molecule of Formula (I) as disclosed herein, such as N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H-pyran-4-ylamino) benzamide. In some embodiments, methods of the present invention are treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an individual, and administering to the individual a molecule which is N-[5-(3,5-difluorobenzyl)-1H-indazol -3-yl]-4-(piperazin-1-yl)-2-(tetrahydro-2H-pyran-4-ylamino) benzamide. In some embodiments, methods of the present invention are to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down -regulation defect, for example a null mutation such as a ROS1 deletion by identifying a ROS1 down-regulation defect, for example a null mutation such as a ROS1 deletion in a cancer or precancerous cell in an individual, and administering to the individual a molecule which is N-[5-(3,5-difluorobenzyl)-1H-indazol-3-yl]-4-(4-methyl-piperazin-1-yl)-2-(tetrahydro-2H-pyran-4-ylamino) benzamide.

In some embodiments, methods of the present invention are to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous cell in an individual, and administering to the individual a molecule of Formula (I) as disclosed herein, such as N -[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin -1-yl)-2-(tetrahydro-2H-pyran-4-ylamino) benzamide.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous cell in an individual comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous cell in an individual comprises assaying for ROS1 transcript accumulation in an RNA population from a cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous cell in an individual comprises determining the nucleic acid sequence such as the genomic deoxyribonucleic acid sequence in a cell or cells or a cell population comprising a cell or cells from a pancreatic cancerous or precancerous cell population.

In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous cell in an individual comprises assaying for ALK, ROS1, TrkA, TrkB, or TrkC activity in a cell extract from a cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous cell in an individual comprises assaying for ALK, ROS1, TrkA, TrkB, or TrkC transcript accumulation in an RNA population from a cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous cell in an individual comprises determining the nucleic acid sequence such as the genomic deoxyribonucleic acid sequence in a cell or cells or a cell population comprising a cell or cells from a cancerous or precancerous cell population.

In some embodiments, methods of the present invention are to treat cell proliferative disorders such as, but not restricted to, benign prostate hyperplasia, familial adenomatosis polyposis, neuro-fibromatosis, psoriasis, atherosclerosis and conditions involving vascular smooth muscle proliferation or neointimal formation such as restenosis following angioplasty or surgery, pulmonary fibrosis, arthritis, glomerulonephritis, retinopathies including diabetic and neonatal retinopathies and age related macular degeneration, graft vessel disease, such as can occur following vessel or organ transplantation, acromegaly and disorders secondary to acromegaly as well as other hypertrophic conditions in which IGF/IGF-1R signaling is implicated, such as fibrotic lung disease, pathologies related to chronic or acute oxidative stress or hyperoxia induced tissue damage, and metabolic disorders in which elevated IGF levels or IGF-1R activity are implicated, such as obesity.

In addition, the method of the present invention also provides tumor angiogenesis and metastasis inhibition.

In some embodiments, the method of the present invention further comprises subjecting the mammal in need thereof to a radiation therapy or chemotherapy regimen in combination with at least one cytostatic or cytotoxic agent. Moreover the invention provides a method for inhibiting the activity ALK protein which comprises contacting the said protein with an effective amount of a compound of formula (I) or formula 2.(I).

In some embodiments, methods of the present invention are for inhibiting at least one of ALK, ROS1, TrkA, TrkB, or TrkC kinase activity, or a combination thereof, in a cell, comprising contacting said cell with an effective amount of a compound disclosed herein. Some embodiments provide methods of inhibiting at least one of ALK, ROS1, TrkA, TrkB, or TrkC kinase activity, or a combination thereof, in a cell, comprising contacting said cell with an effective amount of a compound which is N-[5-(3,5-difluorobenzyl)-1H-indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H-pyran-4-ylamino) benzamide. Some embodiments provide methods of inhibiting at least one of ALK, ROS1, TrkA, TrkB, or TrkC kinase activity, or a combination thereof, in a cell, comprising contacting said cell with an effective amount of a compound which is N-[5-(3,5-difluorobenzyl)-1H-indazol-3-yl]-4-(piperazin-1-yl)-2-(tetrahydro-2H-pyran-4-ylamino) benzamide. Some embodiments provide methods of inhibiting at least one of ALK, ROS1, TrkA, TrkB, or TrkC kinase activity, or a combination thereof, in a cell, comprising contacting said cell with an effective amount of a compound which is N-[5-(3,5-difluorobenzyl)-1H-indazol-3-yl]-4-(4-methyl-piperazin-1-yl)-2-(tetrahydro-2H-pyran-4-ylamino) benzamide.

The present invention also provides a pharmaceutical composition comprising one or more compounds of formula (I) or formula 2.(I) or a pharmaceutically acceptable salt thereof and a pharmaceutically acceptable excipient, carrier or diluent. Some embodiments provide a pharmaceutical composition comprising one or more compounds selected from N-[5-(3,5-difluorobenzyl)-1H-indazol-3-yl]-4-(piperazin-1-yl)-2-(tetrahydro-2H-pyran-4-ylamino) benzamide and N-[5-(3,5-difluorobenzyl)-1H-indazol-3-yl]-4-(4-methyl-piperazin-1-yl)-2-(tetrahydro-2H-pyran-4-ylamino) benzamide or a pharmaceutically acceptable salt thereof and a pharmaceutically acceptable excipient, carrier or diluent. Some embodiments provide a pharmaceutical composition comprising N-[5-(3,5-difluorobenzyl)-1H-indazol-3-yl]-4-(piperazin-1-yl)-2-(tetrahydro-2H-pyran-4-ylamino) benzamide or a pharmaceutically acceptable salt thereof and a pharmaceutically acceptable excipient, carrier or diluent. Some embodiments provide a pharmaceutical composition comprising N-[5-(3,5-difluorobenzyl)-1H-indazol-3-yl]-4-(4-methyl-piperazin-1-yl)-2-(tetrahydro-2H-pyran-4-ylamino) benzamide or a pharmaceutically acceptable salt thereof and a pharmaceutically acceptable excipient, carrier or diluent.

Some embodiments provide methods of inhibiting ALK, ROS1, TrkA, TrkB, or TrkC activity, or a combination thereof, in a patient, comprising administering to said patient an effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide or a pharmaceutically acceptable salt thereof.

Some embodiments provide methods of inhibiting ALK, ROS1, TrkA, TrkB, or TrkC activity, or a combination thereof, in a patient, comprising administering to said patient an effective amount of a compound which is N-[5-(3,5-difluorobenzyl)-1H-indazol-3-yl]-4-(piperazin-1-yl)-2-(tetrahydro-2H-pyran-4-ylamino) benzamide or a pharmaceutically acceptable salt thereof.

Some embodiments provide methods of inhibiting ALK, ROS1, TrkA, TrkB, or TrkC activity, or a combination thereof, in a patient, comprising administering to said patient an effective amount of a compound which is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof.

Some embodiments provide methods of inhibiting ALK, ROS1, TrkA, TrkB, or TrkC activity, or a combination thereof, in a patient, comprising administering to said patient an effective amount of a compound which is N-[5-(3,5-difluoro-benzenesulfonyl)-1H-indazol-3-yl]-2-((R)-2-methoxy-1-methyl-ethylamino)-4-(4-methyl-piperazin-1-yl) benzamide or a pharmaceutically acceptable salt thereof.

Some embodiments provide methods of treating cancer in a patient in need thereof, the method comprising inhibiting ALK, ROS1, TrkA, TrkB, or TrkC activity, or a combination thereof, in said patient, by administering to said patient an effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H- indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide or a pharmaceutically acceptable salt thereof.

Some embodiments provide methods of treating cancer in a patient in need thereof, the method comprising inhibiting ALK, ROS1, TrkA, TrkB, or TrkC activity, or a combination thereof, in said patient, by administering to said patient an effective amount of a compound which is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof.

Some embodiments provide methods of treating cancer in a patient in need thereof, the method comprising inhibiting ALK, ROS1, TrkA, TrkB, or TrkC activity, or a combination thereof, in said patient, by administering to said patient an effective amount of a compound which is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof.

Some embodiments provide methods of treating cancer in a patient in need thereof, the method comprising inhibiting ALK, ROS1, TrkA, TrkB, or TrkC activity, or a combination thereof, in said patient, by administering to said patient an effective amount of a compound which is N-[5-(3,5-difluoro-benzenesulfonyl)-1H -indazol-3-yl]-2-((R)-2-methoxy-1-methyl-ethylamino)-4-(4-methyl-piperazin-1-yl) benzamide or a pharmaceutically acceptable salt thereof.

Some embodiments provide methods of treating non-small cell lung cancer, papillary thyroid cancer, neuroblastoma, pancreatic cancer or colorectal cancer in a patient, comprising administering to said patient an effective amount of a compound selected from N-[5-(3,5-difluorobenzyl)-1H-indazol-3-yl]-4-(piperazin-1-yl)-2-(tetrahydro -2H-pyran-4-ylamino) benzamide, N-[5-(3,5-difluorobenzyl)-1H-indazol-3-yl]-4-(4-methyl -piperazin-1-yl)-2-(tetrahydro-2H-pyran-4-ylamino) benzamide, and N-[5-(3,5-difluoro -benzenesulfonyl)-1H-indazol-3-yl]-2-((R)-2-methoxy-1-methyl-ethylamino)-4-(4-methyl -piperazin-1-yl) benzamide or a pharmaceutically acceptable salt thereof.

Some embodiments provide methods of treating tumors in a patient, said methods comprising administering to the patient an effective amount of a compound selected from N-[5-(3,5-difluorobenzyl)-1H-indazol-3-yl]-4-(piperazin-1-yl)-2-(tetrahydro -2H-pyran-4-ylamino) benzamide, N-[5-(3,5-difluorobenzyl)-1H-indazol-3-yl]-4-(4-methyl -piperazin-1-yl)-2-(tetrahydro-2H-pyran-4-ylamino) benzamide, and N-[5-(3,5-difluoro -benzenesulfonyl)-1H-indazol-3-yl]-2-((R)-2-methoxy-1-methyl-ethylamino)-4-(4-methyl -piperazin-1-yl) benzamide or a pharmaceutically acceptable salt thereof.

Some embodiments provide methods wherein the tumors are caused by the presence of non-small cell lung cancer, papillary thyroid cancer, neuroblastoma, pancreatic cancer or colorectal cancer in the patient. Some embodiments provide methods wherein one or more of the cells comprising the tumors in the patient test positive for the presence of a gene that expresses at least one of ALK, ROS 1, TrkA, TrkB, or TrkC kinase or one or more of the cells comprising the tumors in said patient demonstrates at least one of ALK, ROS1, TrkA, TrkB, or TrkC kinase activity.

Some embodiments provide methods wherein one or more of the cells comprising the tumors in the patient test positive for at least one gene rearrangement comprising the gene, or a fragment thereof, that expresses at least one of ALK, ROS1, TrkA, TrkB, or TrkC kinase. Some embodiments provide such methods wherein the cells test positive for at least one of ROS1, TrkA, TrkB, or TrkC kinases. Some embodiments provide methods wherein the cells test positive for ROS1 kinase. Some embodiments provide methods wherein the cells test positive for at least one of TrkA, TrkB and TrkC kinase. Some embodiments provide methods wherein the cells test positive for TrkA kinase. Some embodiments provide methods wherein the cells test positive for TrkB kinase. Some embodiments provide such methods wherein the cells test positive for TrkC kinase.

Some embodiments provide methods of treating cancer in a patient, the method comprising: (1) testing one or more cells comprising the tumors in the patient for the presence of at least one of ALK, ROS1, TrkA, TrkB, or TrkC kinase; and (2) administering to the patient an effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H- indazol-3-yl]-4-(4-methyl-piperazin-1-yl)-2-(tetrahydro-2H-pyran-4-ylamino) benzamide, and N-[5-(3,5-difluoro-benzenesulfonyl) -1H-indazol-3-yl]-2-((R)-2-methoxy-1-methyl-ethylamino)-4-(4-methyl-piperazin-1-yl) benzamide, or a pharmaceutically acceptable salt thereof, if said one or more cells tests positive for at least one of ALK, ROS1, TrkA, TrkB, or TrkC kinase.

Some embodiments provide methods of treating cancer in a patient, the method comprising: (1) testing one or more cells comprising the tumors in the patient for the presence of at least one of ROS1, TrkA, TrkB, or TrkC kinase; and (2) administering to the patient an effective amount of a compound selected from N-[5-(3,5-difluorobenzyl) -1H- indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H -pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, if said one or more cells tests positive for at least one of ROS1, TrkA, TrkB, or TrkC kinase.

Some embodiments provide methods wherein the patient is administered an effective amount of N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. Some embodiments provide methods wherein the patient is administered an effective amount of N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. Some embodiments provide methods wherein the patient is administered an effective amount of N-[5-(3,5-difluoro-benzenesulfonyl) -1H- indazol-3-yl]-2-((R)-2-methoxy-1-methyl-ethylamino)-4-(4-methyl- piperazin-1-yl) benzamide, or a pharmaceutically acceptable salt thereof.

Some embodiments provide methods of treating cancer in a patient, wherein one or more cancerous cells in said patient express at least one of ROS1, TrkA, TrkB, or TrkC kinase, the method comprising administering to the patient an effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. Some embodiments provide methods of treating cancer in a patient, wherein one or more cancerous cells in said patient express at least one of ROS1, TrkA, TrkB, or TrkC kinase, the method comprising administering to the patient an effective amount of a compound which is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof.

Some embodiments provide methods of treating cancer in a patient, wherein one or more cancerous cells in said patient express at least one of ROS1, TrkA, TrkB, or TrkC kinase, the method comprising administering to the patient an effective amount of a compound which is N-[5-(3,5-difluorobenzyl)-1H-indazol-3-yl]-4-(4-methyl -piperazin-1-yl)-2-(tetrahydro-2H-pyran-4-ylamino) benzamide, or a pharmaceutically acceptable salt thereof. Some embodiments provide methods of treating cancer in a patient, wherein one or more cancerous cells in said patient express at least one of ROS1, TrkA, TrkB, or TrkC kinase, the method comprising administering to the patient an effective amount of a compound which is N-[5-(3,5-difluoro-benzenesulfonyl)-1H -indazol-3-yl]-2-((R)-2-methoxy-1-methyl-ethylamino)-4-(4-methyl-piperazin-1-yl) benzamide, or a pharmaceutically acceptable salt thereof.

Some embodiments provide methods of treating cancer in a patient, wherein one or more cancerous cells in said patient express at least one of ROS1, TrkA, TrkB, or TrkC kinase, the method comprising administering to the patient an effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. Some embodiments provide methods of treating cancer in a patient, wherein one or more cancerous cells in said patient express at least one of ROS1, TrkA, TrkB, or TrkC kinase, the method comprising administering to the patient an effective amount of a compound which is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof.

Some embodiments provide methods of treating cancer in a patient, wherein one or more cancerous cells in said patient express at least one of ROS1, TrkA, TrkB, or TrkC kinase, the method comprising administering to the patient an effective amount of a compound which is N-[5-(3,5-difluorobenzyl)-1H-indazol-3-yl]-4-(4-methyl -piperazin-1-yl)-2-(tetrahydro-2H-pyran-4-ylamino) benzamide, or a pharmaceutically acceptable salt thereof. Some embodiments provide methods of treating cancer in a patient, wherein one or more cancerous cells in said patient express at least one of ROS1, TrkA, TrkB, or TrkC kinase, the method comprising administering to the patient an effective amount of a compound which is N-[5-(3,5-difluoro-benzenesulfonyl)-1H -indazol-3-yl]-2-((R)-2-methoxy-1-methyl-ethylamino)-4-(4-methyl-piperazin-1-yl) benzamide, or a pharmaceutically acceptable salt thereof.

Some embodiments provide methods of treating a patient in which one or more cancerous cells from said patient express at least one of ROS1, TrkA, TrkB, or TrkC kinase, the method comprising administering to the patient an effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof. Some embodiments provide methods of treating a patient in which one or more cancerous cells from said patient express at least one of ROS1, TrkA, TrkB, or TrkC kinase, the method comprising administering to the patient an effective amount of a compound which is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof. Some embodiments provide methods of treating a patient in which one or more cancerous cells from said patient express at least one of ROS1, TrkA, TrkB, or TrkC kinase, the method comprising administering to the patient an effective amount of a compound which is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof. Some embodiments provide methods of treating a patient in which one or more cancerous cells from said patient express at least one of ROS1, TrkA, TrkB, or TrkC kinase, the method comprising administering to the patient an effective amount of a compound which is N-[5-(3,5-difluoro-benzenesulfonyl)-1H-indazol-3-yl]-2-((R)-2-methoxy-1-methyl-ethylamino)-4-(4- methyl-piperazin-1-yl) benzamide, or a pharmaceutically acceptable salt thereof.

Some embodiments provide a method of treating cancer, comprising administering to a patient in which one or more cancerous cells from said patient express at least one of ROS1, TrkA, TrkB, or TrkC kinase an effective amount of a compound selected from N-[5-(3,5-difluorobenzyl)-1H-indazol-3-yl]-4-(piperazin-1-yl)-2-(tetrahydro -2H-pyran-4-ylamino) benzamide, N-[5-(3,5-difluorobenzyl)-1H-indazol-3-yl]-4-(4-methyl -piperazin-1-yl)-2-(tetrahydro-2H-pyran-4-ylamino) benzamide, and N-[5-(3,5-difluoro -benzenesulfonyl)-1H-indazol-3-yl]-2-((R)-2-methoxy-1-methyl-ethylamino)-4-(4-methyl -piperazin-1-yl) benzamide, or a pharmaceutically acceptable salt thereof. Some embodiments provide methods wherein said compound is N-[5-(3,5-difluorobenzyl)-1H -indazol-3-yl]-4-(4-methyl-piperazin-1-yl)-2-(tetrahydro-2H-pyran-4-ylamino) benzamide, or a pharmaceutically acceptable salt thereof. Some embodiments provide methods wherein said compound is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof.

Some emobodiments provide a method for treating a patient having cancer, wherein tumors from said patient are ROS1, TrkA, TrkB, or TrkC positive, a combination thereof, the method comprising administering to the patient an effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2- methoxy-1-methyl-ethylamino)-4-(4-methyl-piperazin-1-yl) benzam ide, or a pharmaceutically acceptable salt thereof.

Some embodiments provide a method for treating a patient having ROS1, TrkA, TrkB, or TrkC positive cancer, or a combination thereof, the method comprising administering to the patient an effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H- indazol-3-yl]-4-(4-methyl-piperazin-1-yl)-2-(tetrahydro-2H-pyran-4-ylamino) benzamide, and N-[5-(3,5-difluoro -benzenesulfonyl)-1H-indazol-3-yl]-2-((R)-2-methoxy-1-methyl-ethylamino)-4-(4-methyl -piperazin-1-yl) benzamide, or a pharmaceutically acceptable salt thereof.

Some embodiments provide a method of treating a cancer patient, comprising (a) acquiring knowledge of the presence of at least one genetic alteration in at least one target gene in the cancer patient, wherein the at least one target gene is selected from ALK1, BDNF, NGF, NGFR, NTF3, NTF4, ROS1, SORT1, NTRK1, NTRK2, and NTRK3; (b) selecting a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methy 1-ethylamino)-4-(4-methyl-piperazin-1-yl) benzamide, or a pharmaceutically acceptable salt thereof, as a treatment for the cancer patient, based on the recognition that said compound is effective in treating cancer patients having said at least one genetic alteration in said at least one target gene; and (c) administering a therapeutically effective amount of said compound to said cancer patient.

Some embodiments provide a method of treating a cancer patient, comprising administering to said cancer patient a therapeutically effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H- indazol-3-yl]-2-((R)-2-methoxy-1-methyl-ethylamino)-4-(4-methyl-piperazin-1-yl) benzamide, or a pharmaceutically acceptable salt thereof, wherein prior to said administration of said compound, said cancer patient is known to possess at least one genetic alteration in at least one target gene selected from ALK1, BDNF, NGF, NGFR, NTF3, NTF4, ROS1, SORT1, NTRK1, NTRK2, and NTRK3.

Some embodiments provide a method of treating cancer in a patient, comprising administering to said cancer patient known to possess at least one genetic alteration in at least one target gene selected from ALK1, BDNF, NGF, NGFR, NTF3, NTF4, ROS1, SORT1, NTRK1, NTRK2, and NTRK3 a therapeutically effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol -3-yl]-4-(4-methyl-piperazin-1-yl)-2-(tetrahydro-2H-pyran-4-ylamino) benzamide, and N -[5-(3,5-difluoro-benzenesulfonyl)-1H-indazol-3-yl]-2-((R)-2-methoxy-1-methyl -ethylamino)-4-(4-methyl-piperazin-1-yl) benzamide, or a pharmaceutically acceptable salt thereof.

Some embodiments provide a method of treating a cancer patient, wherein said cancer patient is known to possess at least one genetic alteration in at least one target gene, comprising administering to said cancer patient a therapeutically effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazo1-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, and wherein said target gene is selected from ALK1, BDNF, NGF, NGFR, NTF3, NTF4, ROS1, SORT1, NTRK1, NTRK2, and NTRK3.

Some embodiments provide a method of treating a cancer patient, wherein prior to said treatment said patient is known to possess at least one genetic alteration in at least one target gene, comprising administering to said cancer patient a therapeutically effective amount of a compound selected from N-[5-(3,5-difluorobenzyl) -1H-indazol-3-yl]-4-(piperazin-1-yl)-2-(tetrahydro-2H-pyran-4-ylamino) benzamide, N-[5-(3,5-difluorobenzy 1)-1H-indazol-3-yl]-4-(4-methyl-piperazin-1-yl)-2-(tetrahydro-2H -pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, and wherein said target gene is selected from ALK1, BDNF, NGF, NGFR, NTF3, NTF4, ROS1, SORT1, NTRK1, NTRK2, and NTRK3.

Some embodiments provide a method of treating a cancer patient, comprising administering to said cancer patient a therapeutically effective amount of a compound selected from N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, and wherein prior to said compound being admininstered to said patient, said patient is known to possess at least one genetic alteration in at least one target gene selected from ALK1, BDNF, NGF, NGFR, NTF3, NTF4, ROS1, SORT1, NTRK1, NTRK2, and NTRK3.

Some embodiments provide a method for treating a cancer patient, comprising (a) acquiring knowledge of the presence of at least one genetic alteration in at least one target gene selected from ALK1, BDNF, NGF, NGFR, NTF3, NTF4, ROS1, SORT1, NTRK1, NTRK2, and NTRK3; and (b) administering to said patient a therapeutically effective amount of a compound selected from N-[5-(3,5-difluorobenzyl) -1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H -pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof.

Some embodiments provide any of the methods described herein wherein the patient or subject is suffering from cancer and the cancer is selected from at least one of non-small cell lung cancer, papillary thyroid cancer, neuroblastoma, pancreatic cancer and colorectal cancer.

Some embodiments provide a pharmaceutical composition comprising a compound of formula (I) or formula 2.(I) in combination with one or more chemotherapeutic agents or radiotherapy, such as radiotherapy as commonly administered to treat, ameliorate the symptoms of, or prevent or delay the onset of cancer. Such agents can include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

Some embodiments provide a product or kit comprising a compound of formula (I) or formula 2.(I) or a pharmaceutically acceptable salt thereof, as defined above, or pharmaceutical compositions thereof and one or more chemotherapeutic agents, as a combined preparation for simultaneous, separate or sequential use in anticancer therapy. Some embodiments provide a product or kit comprising a compound selected from N-[5-(3,5-difluorobenzyl)-1H-indazol-3-yl]-4-(piperazin-1-yl)-2-(tetrahydro-2H-pyran-4-ylamino) benzamide and N-[5-(3,5-difluorobenzyl)-1H- indazol-3-yl]-4-(4-methyl -piperazin-1-yl)-2-(tetrahydro-2H-pyran-4-ylamino) benzamide, or a pharmaceutically acceptable salt thereof, or pharmaceutical compositions thereof and one or more chemotherapeutic agents, as a combined preparation for simultaneous, separate or sequential use in anticancer therapy.

Some embodiments provide a product or kit comprising a compound which is N-[5-(3,5-difluorobenzyl)-1H-indazol-3-yl]-4-(piperazin-1-yl)-2-(tetrahydro-2H -pyran-4-ylamino) benzamide, or a pharmaceutically acceptable salt thereof, or pharmaceutical compositions thereof and one or more chemotherapeutic agents, as a combined preparation for simultaneous, separate or sequential use in anticancer therapy. Some embodiments provide a product or kit comprising a compound which is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, or pharmaceutical compositions thereof and one or more chemotherapeutic agents, as a combined preparation for simultaneous, separate or sequential use in anticancer therapy.

Some embodiments provide a compound of formula (I) or formula 2.(I) or a pharmaceutically acceptable salt thereof, as defined above, for use as a medicament.

Some embodiments provide the use of a compound of formula (I) or formula 2.(I) or a pharmaceutically acceptable salt thereof, as defined above, in the manufacture of a medicament with antitumor activity.

Some embodiments provide a compound of formula (I) or formula 2.(1) or a pharmaceutically acceptable salt thereof, as defined above, for use in a method of treating cancer. Some embodiments may be further summarized by reference to the numerically listed embodiments recited below:

1. A method of treating, ameliorating the symptoms of, delaying the onset of or delaying the progression of cancer comprising the steps of
   determining whether modulation of ROS1 activity is defective in a cell population of an individual, and if said modulation of ROS1 activity is defective,
   administering a molecule of a selected from the list consisting of formula (I) and formula 2.(I) to said individual, thereby treating, ameliorating the symptoms of, delaying the onset of or delaying the progression of cancer.
2. The method of embodiment 1, wherein said determining whether modulation of ROS1 activity is defective comprises assaying for ROS1 kinase activity in an extract of a cell population of said individual.
3. The method of embodiment 1, wherein said determining whether modulation of ROS1 activity is defective comprises assaying for transcript accumulation in an extract comprising RNA of a cell population of said individual.
4. The method of embodiment 1, wherein said determining whether modulation of ROS1 activity is defective comprises sequencing a ROS1 locus in the genomic DNA of a cell population of said individual.
5. The method of embodiment 4, wherein said defective modulation of ROS1 activity comprises upregulation of ROS1 activity.
6. The method of embodiment 5, wherein a fusion of a coding region of a second protein at the ROS1 locus indicates upregulation of ROS1 kinase activity.
7. The method of embodiment 4, wherein said defective modulation of ROS1 activity comprises a reduction of ROS1 activity to a lower level.
8. The method of embodiment 7, wherein a null mutation of said ROS1 locus indicates that ROS1 activity is reduced.
9. The method of embodiment 7, wherein said null mutation comprises an insertion.
10. The method of embodiment 7, wherein said null mutation comprises a frame shift of a coding region encoding ROS1.
11. The method of embodiment 7, wherein said null mutation comprises a deletion within the locus encoding ROS1.
12. The method of embodiment 7, wherein said null mutation comprises a deletion of the nucleic acid sequence spanning the ROS1 locus.
13. The method of embodiment 7, wherein a mutation affecting accumulation of ROS1 mRNA indicates that ROS1 activity is reduced.
14. The method of any of embodiments 1-13, wherein said molecule is a molecule of formula (I).
15. The method of any of embodiments 1-13, wherein said molecule is a molecule of formula 2.(I).
16. The method of any of embodiments 1-13, wherein said molecule is N-[5-(3,5-difluorobenzyl)-1H-indazol-3-yl]-4-(piperazin-1-yl)-2-(tetrahydro-2H-pyran-4-ylamino) benzamide 17. The method of any of embodiments 1-13, wherein said molecule is N-[5-(3,5-difluorobenzyl)-1H-indazol-3-yl]-4-(4-methyl -piperazin-1-yl)-2-(tetrahydro-2H-pyran-4-ylamino) benzamide.
18. The method of any of embodiments 1-13, wherein said molecule is N-[5-(3,5-difluoro-benzenesulfonyl)-1H-indazol-3-yl]-2-((R)-2-methoxy-1-methyl-ethylamino)-4-(4-methyl-piperazin-1-yl) benzamide.
19. The method of any of embodiments 1-18, wherein said cancer comprises pancreatic cancer.
20. The method of any of embodiments 1-19, further comprising administering radiotherapy to said individual.

Some additional embodiments may be further summarized by reference to the numerically listed embodiments recited below:

1. The use of a compound selected from the group consisting of N-[5-(3,5-difluorobenzyl)-1H-indazol-3-yl]-4-(piperazin -1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro -benzenesulfonyl)-1H-indazol-3-yl]-2-((R)-2-methoxy-1-methyl -ethylamino)-4-(4-methyl-piperazin-1-yl) benzamide, or a pharmaceutically acceptable salt thereof, for preparing a medicament for treating cancer in a patient, wherein said cancer patient has at least one genetic alteration in at least one target gene selected from ROS1, NTRK1, NTRK2, and NTRK3.

2. Use according to embodiment 1, wherein said at least one target gene is ROS1.

3. Use according to embodiment 1, wherein said at least one target gene is selected from the group consisting of NTRK1, NTRK2, and NTRK3.

4. Use according to embodiment 1, wherein said compound is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof.

5. Use according to embodiment 4, wherein said at least one target gene is ROS1.

6. Use according to embodiment 4, wherein said at least one target gene is selected from the group consisting of NTRK1, NTRK2, and NTRK3.

7. Use according to embodiment 1, wherein said compound is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof.

8. Use according to embodiment 7, wherein said at least one target gene is ROS1.

9. Use according to embodiment 7, wherein said at least one target gene is selected from the group consisting of NTRK1, NTRK2, and NTRK3.

10. Use according to embodiment 1, wherein said compound is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof.

11. Use according to embodiment 10, wherein said at least one target gene is ROS1.

12. Use according to embodiment 10, wherein said at least one target gene is selected from the group consisting of NTRK1, NTRK2, and NTRK3.

13. Use according to embodiment 1, wherein said cancer is selected from the group consisting of non-small cell lung cancer, papillary thyroid cancer, neuroblastoma, pancreatic cancer and colorectal cancer.

14. Use according to embodiment 1, wherein said compound is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof, and said cancer is selected from the group consisting of non-small cell lung cancer, papillary thyroid cancer, neuroblastoma, pancreatic cancer and colorectal cancer.

15. Use according to embodiment 14, wherein said cancer is selected from the group consisting of non-small cell lung cancer, neuroblastoma and colorectal cancer.

16. Use according to embodiment 1, wherein said compound is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof, and said cancer is selected from the group consisting of non-small cell lung cancer, papillary thyroid cancer, neuroblastoma, pancreatic cancer and colorectal cancer.

17. Use according to embodiment 16, wherein said cancer is selected from the group consisting of non-small cell lung cancer, neuroblastoma and colorectal cancer.

18. Use according to embodiment 1, wherein said compound is N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, and said cancer is selected from the group consisting of non-small cell lung cancer, papillary thyroid cancer, neuroblastoma, pancreatic cancer and colorectal cancer.

19. Use according to embodiment 18, wherein said cancer is selected from the group consisting of non-small cell lung cancer, neuroblastoma and colorectal cancer.

20. A compound selected from the group consisting of N-[5-(3,5-difluorobenzyl)-1H-indazol-3-yl]-4-(piperazin-1-yl)-2-(tetrahydro-2H-pyran-4-ylam ino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof, for use in method of treating cancer in a patient having at least one genetic alteration in at least one target gene selected from the group consisting of ROS1, NTRK1, NTRK2, and NTRK3, wherein said method comprises the steps of:

a) determining whether said patient has at least one genetic alteration in at least one target gene selected from the group consisting of ROS1, NTRK1, NTRK2, and NTRK3; and b) administering a therapeutically effective amount of said compound to said cancer patient.

21. A compound for use according to embodiment 20, wherein said cancer is selected from the group consisting of non-small cell lung cancer, papillary thyroid cancer, neuroblastoma, pancreatic cancer and colorectal cancer.

22. A method of treating cancer in a patient, wherein said patient is known to possess at least one genetic alteration in at least one target gene selected from ROS1, NTRK1, NTRK2, and NTRK3, comprising administering to said cancer patient a therapeutically effective amount of a compound selected from N-[5-(3,5-difluorobenzy 1)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, and N-[5-(3,5-difluoro-benzenesulfonyl)-1H-indazol-3-yl]-2-((R)-2-methoxy-1-methyl-ethylamino)-4-(4-methyl-piperazin-1-yl) benzamide, or a pharmaceutically acceptable salt thereof.

Some embodiments include any of the methods described herein, wherein said cancer is selected from non-small cell lung cancer, papillary thyroid cancer, neuroblastoma, pancreatic cancer and colorectal cancer. Some embodiments are any of the methods described herein wherein said cancer is non-small cell lung cancer. Some embodiments include any of the methods described herein, wherein said cancer is said cancer is papillary thyroid cancer. Some embodiments include any of the methods described herein, wherein said cancer is wherein said cancer is neuroblastoma. Some embodiments include any of the methods described herein, wherein said cancer is wherein said cancer is pancreatic cancer. Some embodiments include any of the methods described herein, wherein said cancer is wherein said cancer is colorectal cancer.

Some embodiments include any of the methods described herein, wherein any of the compounds described herein are administered to said individual in an amount ranging from about 200 mg/m$^2$ to about 1600 mg/m$^2$, or from about 200 mg/m$^2$ to about 1200 mg/m$^2$, or from about 200 mg/m$^2$ to about 1000 mg/m$^2$, or from about 400 mg/m$^2$ to about 1200 mg/m$^2$, or from about 400 mg/m$^2$ to about 1000 mg/m$^2$, or from about 800 mg/m$^2$ to about 1000 mg/m$^2$, or from about 800 mg/m$^2$ to about 1200 mg/m$^2$, or from about 800 mg/m$^2$ to about 1200 mg/m$^2$, or from about 800 mg/m$^2$ to about 1600 mg/m$^2$. Some embodiments include any of the methods described herein, wherein any of the compounds described herein are administered to said individual in an amount of about 200 mg/m$^2$, about 300 mg/m$^2$, about 400 mg/m$^2$, about 500 mg/m$^2$, about 600 mg/m$^2$, about 700 mg/m$^2$, about 800 mg/m$^2$, about 900 mg/m$^2$, about 1000 mg/m$^2$, about 1100 mg/m$^2$, about 1200 mg/m$^2$, about 1300 mg/m$^2$, about 1400 mg/m$^2$, about 1500 mg/m$^2$, about 1600 mg/m$^2$, about 1700 mg/m$^2$, about 1800 mg/m$^2$, about 1900 mg/m$^2$, or about 2000 mg/m$^2$.

Some embodiments relate to the use of any of the compounds as described herein, or a pharmaceutically acceptable salt thereof, in the manufacture of a medicament for the treatment of abnormal cell growth in a mammal. The present invention further relates to the use of any of the compounds as described herein, or a pharmaceutically acceptable salt thereof, in the manufacture of a medicament for the treatment of abnormal cell growth in a mammal wherein the abnormal cell growth is cancerous or non-cancerous. In some embodiments, the abnormal cell growth is cancerous. In another embodiment, the abnormal cell growth is non-cancerous.

Some embodiments relate to any of the compounds described herein, or pharmaceutically acceptable salts thereof, for use as a medicament. Some embodiments relate to the use of any of the compounds described above, or pharmaceutically acceptable salts thereof, for the manufacture of a medicament for the treatment of abnormal cell growth.

As used herein "cancer" refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but are not limited to sarcomas and carcinomas. Examples of cancers of the blood include but are not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one.

Some embodiments relate to compositions comprising a compound of Formula I or a pharmaceutically acceptable salt thereof (e.g., pharmaceutical compositions). Accordingly, in some embodiments, the invention relates to a pharmaceutical composition comprising a compound of Formula I, or a pharmaceutically acceptable salt, a pharmaceutically acceptable carrier and, optionally, at least one additional medicinal or pharmaceutical agent. In some embodiments, the at least one additional medicinal or pharmaceutical agent is an anti-cancer agent as described below.

The pharmaceutically acceptable carrier may comprise a conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non- limiting examples of materials, therefore, include lactose or milk sugar and high molecular weight polyethylene glycols.

When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

In some embodiments, the composition comprises a therapeutically effective amount of a compound as disclosed herein and a pharmaceutically acceptable carrier.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound disclosed herein and an inert, pharmaceutically acceptable carrier or diluent.

To treat or prevent diseases or conditions mediated by ALK, ROS1, TrkA, TrkB, or TrkC, or a combination thereof, a pharmaceutical composition of the invention is administered in a suitable formulation prepared by combining a therapeutically effective amount (i.e., a ALK, ROS1, TrkA, TrkB, or TrkC modulating, regulating, or inhibiting amount effective to achieve therapeutic efficacy) of at least one compound of the present invention (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time- release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of a compound of the present invention may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g. sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a co-solvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5 W) contains VPD diluted 1:1 with a 5% dextrose in water solution. This co-solvent system dissolves hydrophobic compounds well, and itself produces low toxicity upon systemic administration. The proportions of a co-solvent system may be suitably varied without destroying its solubility and toxicity characteristics. Furthermore, the identity of the co-solvent components may be varied: for example, other low-toxicity non-polar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol®, Transcutol® and the like may be used.

Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage-determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg. Furthermore, the pharmaceutically acceptable formulations of the present invention may contain a compound of the present invention, or a salt or solvate thereof, in an amount of about 50 mg, about 100 mg, about 150 mg, about 200 mg, about 250 mg, about 300 mg, about 350 mg, about 400 mg, about 450 mg, or about 500 mg.

Additionally, the pharmaceutically acceptable formulations of the present invention may contain a compound of the present invention, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds of the present invention, or salts or solvates thereof, may be administered to a mammal suffering from abnormal cell growth, such as a human, either alone or as part of a pharmaceutically acceptable formulation, once a day, twice a day, three times a day, or four times a day, or even more frequently.

Those of ordinary skill in the art will understand that with respect to the compounds of the present invention, the particular pharmaceutical formulation, the dosage, and the number of doses given per day to a mammal requiring such treatment, are all choices within the knowledge of one of ordinary skill in the art and can be determined without undue experimentation.

Administration of the compounds disclosed herein may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra- patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The compounds, compositions and methods provided herein are useful for the treatment of cancers including but not limited to cancers of the: circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue; respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, for example, neoplasms of the central nervous system (CNS), primary CNS lymphoma, skull cancer (osteoma, hemangioma, granuloma, xanthoma, osteitis deformans), meninges (meningioma, men ingiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; skin, for example, malignant melanoma, cutaneous melanoma, basal cell carcinoma, squamous cell carcinoma, Karposi's sarcoma, moles dysplastic nevi, lipoma, angioma, dermatofibroma, and keloids; adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of "cancer" when used herein in connection with the present invention include cancer selected from lung cancer (NSCLC and SCLC), cancer of the head or neck, ovarian cancer, colon cancer, rectal cancer, prostate cancer, cancer of the anal region, stomachcancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

In some embodiments, the compounds and the compositions disclosed herein are useful for the treatment of cancers, including Spitz melanoma, perineural invasion, pulmonary large cell neuroendocrine carcinoma, uterine carcinoma, juvenile breast cancer, nasopharyngeal carcinoma, adenoid cystic cancer, meduallary thyroid cancer, salivary cancer, congenital infantile fibrosarcoma, mesoblastic nephroma, esophageal cancer (squamous), diffuse large B-cell lymphoma, papillary thyroid cancer, and mammary analogue secretory carcinoma.

In some embodiments, the compounds disclosed herein may be used in combination with one or more additional anti-cancer agents which are described below. When a combination therapy is used, the one or more additional anti-cancer agents may be administered sequentially or simultaneously with the compound of the invention. In some embodiments, the additional anti-cancer agent is administered to a mammal (e.g., a human) prior to administration of the compound of the invention. In some embodiments, the additional anti-cancer agent is administered to the mammal after administration of the compound of the invention. In some embodiments, the additional anti-cancer agent is administered to the mammal (e.g., a human) simultaneously with the administration of the compound disclosed herein.

Some embodiments also relate to a pharmaceutical composition for the treatment of abnormal cell growth in a mammal, including a human, which comprises an amount of a compound disclosed herein, as defined above (including hydrates, solvates and polymorphs of said compound or pharmaceutically acceptable salts thereof), in combination with one or more (preferably one to three) anti-cancer agents selected from the group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

In some embodiments, the anti-cancer agent used in conjunction with a compound disclosed herein and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKC.beta. inhibitors, COX-2 (cyclooxygenase II) inhibitors, integrins (alpha-v/beta-3), MMP-2 (matrix-metalloprotienase 2) inhibitors, and MMP-9 (matrix-metalloprotienase 9) inhibitors. Preferred anti-angiogenesis agents include sunitinib (Sutent®), bevacizumab (Avastin®), axitinib (AG 13736), SU 14813 (Pfizer), and AG 13958 (Pfizer).

Additional anti-angiogenesis agents include vatalanib (CGP 79787), Sorafenib (Nexavar®), pegaptanib octasodium (Macugen®), vandetanib (Zactima®), PF -0337210 (Pfizer), SU 14843 (Pfizer), AZD 2171 (AstraZeneca), ranibizumab (Lucentis®), Neovastat® (AE 941), tetrathiomolybdata (Coprexa®), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex®) and UCN 01 (Kyowa Hakko).

Other examples of anti-angiogenesis agents which can be used in conjunction with a compound of Disclosed herein and pharmaceutical compositions described herein include celecoxib (Celebrex®), parecoxib (Dynastat®), deracoxib (SC 59046), lumiracoxib (Preige®), valdecoxib (Bextra®), rofecoxib (Vioxx®), iguratimod (Careram®), IP 751 (Invedus), SC-58125 (Pharmacia) and etoricoxib (Arcoxia®).

Other anti-angiogenesis agents include exisulind (Aptosyn®), salsalate (Amigesic®), diflunisal (Dolobid®), ibuprofen (Motrin®), ketoprofen (Orudis®) nabumetone (Relafen®), piroxicam (Feldene®), naproxen (Aleve®, Naprosyn®) diclofenac (Voltaren®), indomethacin (Indocin®), sulindac (Clinoril®), tolmetin (Tolectin®), etodolac (Lodine®), ketorolac (Toradol®), and oxaprozin (Daypro®).

Other anti-angiogenesis agents include ABT 510 (Abbott), apratastat (TMI 005), AZD 8955 (AstraZeneca), incyclinide (Metastat®), and PCK 3145 (Procyon).

Other anti-angiogenesis agents include acitretin (Neotigason®), plitidepsin (Aplidine®), cilengtide (EMD 121974), combretastatin A4 (CA4P), fenretinide (4 HPR), halofuginone (Tempostatin®), Panzem® (2-methoxyestradiol), PF-03446962 (Pfizer), rebimastat (BMS 275291), catumaxomab (Removab®), lenalidomide (Revlimid®) squalamine (EVIZON®), thalidomide (Thalomid®), Ukrain® (NSC 631570), Vitaxin® (MEDI 522), and zoledronic acid (Zometa®).

In some embodiments, the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, ALK inhibitors, ROS1 inhibitors, TrkA inhibitors, TrkB inhibitors, TrkC inhibitors, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi -targeted kinase inhibitors.

Preferred signal transduction inhibitors include gefitinib (Iressa®), cetuximab (Erbitux®), erlotinib (Tarceva®), trastuzumab (Herceptin®), sunitinib (Sutent®) imatinib (Gleevec®), and PD325901 (Pfizer).

Additional examples of signal transduction inhibitors which may be used in conjunction with a compound of Disclosed herein and pharmaceutical compositions described herein include BMS 214662 (Bristol-Myers Squibb), lonafarnib (Sarasar®), pelitrexol (AG 2037), matuzumab (EMD 7200), nimotuzumab (TheraCIM h -R3®), panitumumab (Vectibix®), Vandetanib (Zactima®), pazopanib (SB 786034), ALT 110 (Alteris Therapeutics), BIBW 2992 (Boehringer Ingelheim), and Cervene® (TP 38).

Other examples of signal transduction inhibitor include PF-2341066 (Pfizer), PF-299804 (Pfizer), canertinib (CI 1033), pertuzumab (Omnitarg®), Lapatinib (Tycerb®), pelitinib (EKB 569), miltefosine (Miltefosin®), BMS 599626 (Bristol-Myers Squibb), Lapuleucel-T (Neuvenge®), NeuVax® (E75 cancer vaccine), Osidem® (IDM 1), mubritinib (TAK-165), CP-724,714 (Pfizer), panitumumab (Vectibix®), lapatinib (Tycerb®), PF-299804 (Pfizer), pelitinib (EKB 569), and pertuzumab (Omnitarg®).

Other examples of signal transduction inhibitors include ARRY 142886 (Array Biopharm), everolimus (Certican®), zotarolimus (Endeavor®), temsirolimus (Torisel®), AP 23573 (ARIAD), and VX 680 (Vertex).

Additionally, other signal transduction inhibitors include XL 647 (Exelixis), sorafenib (Nexavar®), LE-AON (Georgetown University), and GI-4000 (Globelmmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PD 0332991 (Pfizer), AG 024322 (Pfizer), LOX0-101 (Loxo Oncology), crizotinib, and ceritinib.

In some embodiments, the compounds of disclosed herein are used together with classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins.

Examples of classical antineoplastic agents used in combination therapy with a compound of disclosed herein, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, ospemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, episteride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with compounds of disclosed herein include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubic in, pixantrone, procarbazine, rebeccamycin, sobuzoxane, tafluposide, valrubic in, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In some embodiments, the compounds of disclosed herein are used together with dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda®), cytosine arabinoside, Gemzar® (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]—2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with a compound of disclosed herein, optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paciltaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta®), DMXAA (Antisoma), ibandronic acid, L-asparaginase, pegaspargase (Oncaspar®), Efaproxiral (Efaproxyn®—radiation therapy)), bexarotene (Targretin®), Tesmilifene (DPPE—enhances efficacy of cytotoxics)), Theratope® (Biomira), Tretinoin (Vesanoid®), tirapazamine (Trizaone®), motexafin gadolinium (Xcytrin®) Cotara® (mAb), and NBI-3001 (Protox Therapeutics), polyglutamate-paclitaxel (Xyotax®) and combinations thereof.

Further examples of classical antineoplastic agents used in combination therapy with a compound of disclosed herein, optionally with one or more other agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

Some embodiments relate to a method for the treatment of breast cancer in a human in need of such treatment, comprising administering to said human an amount of a compound of disclosed herein, in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

Some embodiments provide a method of treating colorectal cancer in a mammal, such as a human, in need of such treatment, by administering an amount of a compound of disclosed herein, in combination with one or more (preferably one to three) anti-cancer agents. Examples of particular anti-cancer agents include those typically used in adjuvant chemotherapy, such as FOLFOX, a combination of 5-fluorouracil (5-FU) or capecitabine (Xeloda), leucovorin and oxaliplatin (Eloxatin). Further examples of particular anti-cancer agents include those typically used in chemotherapy for metastatic disease, such as FOLFOX or FOLFOX in combination with bevacizumab (Avastin); and FOLFIRI, a combination of 5-FU or capecitabine, leucovorin and irinotecan (Camptosar). Further examples include 17-DMAG, ABX-EFR, AMG-706, AMT-2003, ANX-510 (CoFactor), aplidine (plitidepsin, Aplidin), Aroplatin, axitinib (AG-13736), AZD-0530, AZD-2171, bacillus Calmette-Guerin (BCG), bevacizumab (Avastin), BIO-117, BIO-145, BMS-184476, BMS-275183, BMS-528664, bortezomib (Velcade), C-1311 (Symadex), cantuzumab mertansine, capecitabine (Xeloda), cetuximab (Erbitux), clofarabine (Clofarex), CMD-193, combretastatin, Cotara, CT-2106, CV-247, decitabine (Dacogen), E-7070, E-7820, edotecarin, EMD-273066, enzastaurin (LY-317615) epothilone B (EPO -906), erlotinib (Tarceva), flavopyridol, GCAN-101, gefitinib (Iressa), huA33, huC242-DM4, imatinib (Gleevec), indisulam, ING-1, irinotecan (CPT-11, Camptosar) ISIS 2503, ixabepilone, lapatinib (Tykerb), mapatumumab (HGS-ETR1), MBT-0206, MEDI-522 (Abregrin), Mitomycin, MK-0457 (VX-680), MLN-8054, NB-1011, NGR-TNF, NV-1020, oblimersen (Genasense, G3139), OncoVex, ONYX 015 (CI-1042), oxaliplatin (Eloxatin), panitumumab (ABX-EGF, Vectibix), pelitinib (EKB-569), pemetrexed (Alimta), PD -325901, PF-0337210, PF-2341066, RAD-001 (Everolimus), RAV-12, Resveratrol, Rexin -G, S-1 (TS-1), seliciclib, SN-38 liposome, Sodium stibogluconate (SSG), sorafenib (Nexavar), SU-14813, sunitinib (Sutent), temsirolimus (CCI 779), tetrathiomolybdate, thalomide, TLK-286 (Telcyta), topotecan (Hycamtin), trabectedin (Yondelis), vatalanib (PTK-787), vorinostat (SAHA, Zolinza), WX-UK1, and ZYC300, wherein the amounts of the active agent together with the amounts of the combination anticancer agents are effective in treating colorectal cancer.

Some embodiments provide methods for the treatment of renal cell carcinoma in a human in need of such treatment, comprising administering to said human an amount of a compound of disclosed herein, in combination with one or more (preferably one to three) anti-cancer agents selected from the group consisting of capecitabine (Xeloda), interferon alpha, interleukin-2, bevacizumab (Avastin), gemcitabine (Gemzar), thalidomide, cetuximab (Erbitux), vatalanib (PTK-787), Sutent, AG-13736, SU-11248, Tarceva, Iressa, Lapatinib and Gleevec, wherein the amounts of the active agent together with the amounts of the combination anticancer agents is effective in treating renal cell carcinoma.

Some embodiments provide methods for the treatment of melanoma in a human in need of such treatment, comprising administering to said human an amount of a compound of disclosed herein, in combination with one or more (preferably one to three) anti-cancer agents selected from the group consisting of interferon alpha, interleukin-2, temozolomide (Temodar), docetaxel (Taxotere), paclitaxel, Dacarbazine (DTIC), carmustine (also known as BCNU), Cisplatin, vinblastine, tamoxifen, PD-325,901, Axitinib, bevacizumab (Avastin), thalidomide, sorafanib, vatalanib (PTK-787), Sutent, CpG-7909, AG-13736, Iressa, Lapatinib and Gleevec, wherein the amounts of the active agent together with the amounts of the combination anticancer agents is effective in treating melanoma.

Some embodiments provide methods for the treatment of lung cancer in a human in need of such treatment, comprising administering to said human an amount of a compound disclosed herein, in combination with one or more (preferably one to three) anti-cancer agents selected from the group consisting of capecitabine (Xeloda), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, and Paraplatin (carboplatin), wherein the amounts of the active agent together with the amounts of the combination anticancer agents is effective in treating lung cancer.

BRIEF DESCRIPTION OF THE DRAWING

The FIGURE depicts steady state pK profile of N-[5-(3, 5-difluorobenzyl)-1H-indazol-3-yl]-4-(4-methyl-piperazin-1-yl)-2-(tetrahydro-2H-pyran-4-ylamino) benzamide in patients on dosing Schedule A.

DETAILED DESCRIPTION

Methods for treating, ameliorating the symptoms of, delaying the progression of, delaying the onset of or otherwise addressing diseases caused by and/or associated with deregulated protein kinase activity, particularly ROS family, PLK family, protein kinase C in different isoforms, Met, PAK-4, PAK-5, ZC-1, STLK-2, DDR-2, Aurora 1, Aurora 2, Bub-1, Chkl, Chk2, HER2, rafl , MEKI, MAPK, EGF-R, PDGF-R, FGF-R, FLT3, JAK2, IGF-R, ALK, PI3K, weel kinase, Src, Abl, Akt, MAPK, ILK, MK-2, IKK-2, Cdc7, Nek, Cdk/cyclin kinase family, more particularly Aurora 2, IGF-1R and ALK activity, and ROS1 activity, and further more particularly ALK activity and/or ROS1 activity, which comprises administering to a mammal in need thereof an effective amount of a substituted indazole compound represented by formula (I) or formula 2.(I) as defined below, are disclosed herein.

Some embodiments provide methods for treating a disease caused by and/or associated with dysregulated protein kinase activity selected from the group consisting of cancer and cell proliferative disorders.

Some embodiments provide methods for treating specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, angiosarcoma, glioblastoma, holangiocarcinoma, inflammatory myofibroblastic tumor, epithelioid hemangioendothelioma, astrocytoma, meningioma, angiosarcoma, epithelioid hemangiothelioma, keratocanthomas, thyroid follicular cancer, Kaposi's sarcoma, and Pancreatic cancer.

Some embodiments provide methods for treating specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, Pancreatic cancer, and medulloblastoma.

Some embodiments provide methods for treating ALK+ Anaplastic Large Cell Lymphomas (ALCL) and possibly other indications in which the ALK activity might play a role, like Neuroblastoma, Rhabdomyosarcoma, Glioblastoma, Inflammatory Myofibroblastic Tumor, and some kind of Melanomas, Breast Carcinomas, Ewings sarcomas, Retinoblastomas and Non Small Cell Lung Carcinomas (NSCLC).

Some embodiments provide methods for treating, reducing the symptoms of, ameliorating the symptoms of, delaying the onset of, or otherwise pharmaceutically addressing Pancreatic cancer and possibly other indications in which a defect in the modulation of ROS1 activity, or upregulation, misregulation or deletion thereof might play a role by administering a molecule of Formula (I) as disclosed herein, such as N-[5-(3,5-difluorobenzyl)-1H-indazol-3-yl]-4-(piperazin-1-yl)-2-(tetrahydro-2H -pyran-4-ylamino) benzamide or N-[5-(3,5-difluorobenzyl)-1H-indazol-3-yl]-4-(4-methyl -piperazin-1-yl)-2-(tetrahydro-2H-pyran-4-ylamino) benzamide.

Some embodiments provide methods for treating, reducing the symptoms of, ameliorating the symptoms of, delaying the onset of, or otherwise pharmaceutically addressing Pancreatic cancer and possibly other indications in which a defect in the modulation of ROS1 activity, or upregulation, misregulation or deletion thereof might play a role by administering a molecule of U.S. Pat. No. 8,299,057, issued Oct. 30, 2012, the entirety of which is hereby incorporated by reference. Some embodiments provide methods for treating, reducing the symptoms of, ameliorating the symptoms of, delaying the onset of, or otherwise pharmaceutically addressing Pancreatic cancer and possibly other indications in which a defect in the modulation of ROS1 activity, or upregulation, misregulation or deletion thereof might play a role by administering a molecule of U.S. Pat. No. 8,114,865, issued Feb. 14, 2012, the entirety of which is hereby incorporated by reference.

Some embodiments provide methods for treating, reducing the symptoms of, ameliorating the symptoms of, delaying the onset of, or otherwise pharmaceutically addressing Pancreatic cancer associated with a ROS1 down-regulation defect, for example a null mutation such as a ROS1 deletion by identifying a ROS1 down -regulation defect, for example a null mutation such as a ROS1 deletion in a cancer or precancerous pancreatic cell in an individual, and administering to the individual a molecule of Formula (I) as disclosed herein, such as N-[5-(3,5-difluorobenzyl)-1H -indazol-3-yl]-4-(piperazin-1-yl)-2-(tetrahydro-2H-pyran-4-ylamino) benzamide or N-[5-(3,5-difluorobenzyl)-1H-indazol-3-yl]-4-(4-methyl-piperazin-1-yl)-2-(tetrahydro-2H -pyran-4-ylamino) benzamide.

Some embodiments provide for identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an individual comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an individual comprises assaying for ROS1 transcript accumulation in an RNA population from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an individual comprises determining the nucleic acid sequence such as the genomic deoxyribonucleic acid sequence in a cell or cells or a cell population comprising a cell or cells from a pancreatic cancerous or precancerous cell population.

Some embodiments provide methods to treat cell proliferative disorders such as, but not restricted to, benign prostate hyperplasia, familial adenomatosis polyposis, neuro-fibromatosis, psoriasis, atherosclerosis and conditions involving vascular smooth muscle proliferation or neointimal formation such as restenosis following angioplasty or surgery, pulmonary fibrosis, arthritis, glomerulonephritis, retinopathies including diabetic and neonatal retinopathies and age related macular degeneration, graft vessel disease, such as can occur following vessel or organ transplantation, acromegaly and disorders secondary to acromegaly as well as other hypertrophic conditions in which IGF/IGF-1R signaling is implicated, such as fibrotic lung disease, pathologies related to chronic or acute oxidative stress or hyperoxia induced tissue damage, and metabolic disorders in which elevated IGF levels or IGF-1R activity are implicated, such as obesity.

In addition, the method of the present invention also provides tumor angiogenesis and metastasis inhibition.

Some embodiments further comprise subjecting the mammal in need thereof to a radiation therapy or chemotherapy regimen in combination with at least one cytostatic or cytotoxic agent. Moreover the invention provides a method for inhibiting the activity ALK protein which comprises contacting the said protein with an effective amount of a compound of formula (I) or formula 2.(I). Formula I The compounds of formula (I) may have one or more asymmetric centers, and may therefore exist as individual optical isomers or racemic mixtures. Accordingly, all the possible isomers, and their mixtures, of the compounds of formula (I) are within the scope of the present invention.

Derivatives of compounds of formula (I) originating from metabolism in a mammal, and the pharmaceutically acceptable bio-precursors (otherwise referred to as pro-drugs) of the compounds of formula (I) are also within the scope of the present invention.

In addition to the above, as known to those skilled in the art, the unsubstituted nitrogen on the pyrazole ring of the compounds of formula (I) rapidly equilibrates in solution to form a mixture of tautomers, as depicted below:

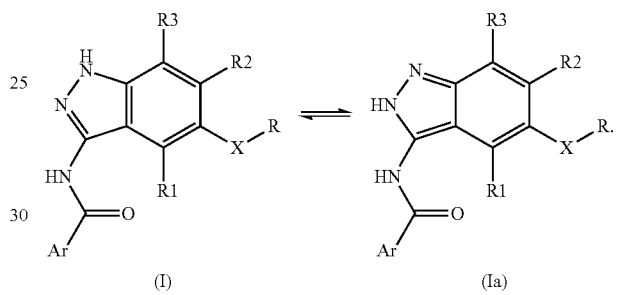

X, Ar, R, R1, R2 and R3 are as defined above.

Accordingly, in the present invention, where only one tautomer is indicated for the compounds of formula (I), the other tautomer (Ia) is also within the scope of the present invention, unless specifically noted otherwise.

The general terms as used herein, unless otherwise specified, have the meaning reported below as applied to formula (I).

The term "straight or branched C1-C6 alkyl" refers to a saturated aliphatic hydrocarbon radical, including straight chain and branched chain groups of from 1 to 6 carbon atoms, e.g. methyl, ethyl, propyl, 2-propyl, n-butyl, isobutyl, tert-butyl, pentyl and the like. The alkyl group may be substituted or unsubstituted. When substituted, the substituent groups are preferably one to three, independently selected from the group consisting of halogen, C2-C6 alkenyl, C2-C6 alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted C3-C6 cycloalkyl, heterocyclyl and aryl, wherein R4, R5, R6, R7, R8, R9 and R10 are as defined above.

The term "C3-C6 cycloalkyl" refers to a 3- to 6-membered all-carbon monocyclic ring, which may contain one or more double bonds but does not have a completely conjugated π-electron system. Examples of cycloalkyl groups, without limitation, are cyclopropyl, cyclobutyl, cyclopentyl, cyclopentenyl, cyclohexyl, cyclohexenyl and cyclohexadienyl. A cycloalkyl group may be substituted or unsubstituted. When substituted, the substituent groups are preferably one or two substituents, independently selected from the group consisting of halogen, C2-C6 alkenyl, C2-C6 alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted straight or branched C1-C6 alkyl, C3-C6 cycloalkyl, heterocyclyl and aryl, wherein R4, R5, R6, R7, R8, R9 and R10 are as defined above.

The term "heterocyclyl" refers to a 3- to 7-membered, saturated or partially unsaturated carbocyclic ring where one or more carbon atoms are replaced by heteroatoms such as nitrogen, oxygen and sulfur. Not limiting examples of heterocyclyl groups are, for instance, oxiranyl, aziridinyl, oxetanyl, azetidinyl, tetrahydrofuranyl, dihydrofuranyl, tetrahydrothiophenyl, dihydrothiophenyl, pyrrolidinyl, dihydropyrrolyl, pyranyl, dihydropyranyl, tetrahydropyranyl, tetrahydrothiopyranyl, piperidinyl, pyrazolinyl, isoxazolidinyl, isoxazolinyl, thiazolidinyl, thiazolinyl, isothiazolinyl, dioxanyl, piperazinyl, morpholinyl, thiomorpholinyl, examethyleneiminyl, homopiperazinyl and the like. A heterocyclyl group may be substituted or unsubstituted. When substituted, the substituent groups are preferably one or two substituents, independently selected from the group consisting of halogen, C2-C6 alkenyl, C2-C6 alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted straight or branched C1-C6 alkyl, C3-C6 cycloalkyl, heterocyclyl and aryl, wherein R4, R5, R6, R7, R8, R9 and R10 are as defined above.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated pi-electron bond system. Non limiting examples of such aryl groups are phenyl, α- or β-naphthyl or biphenyl groups.

The term "heteroaryl" refers to aromatic heterocyclic rings, typically 5-to 7-membered heterocycles with from I to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

The aryl and heteroaryl groups can be optionally substituted by one or more, preferably one, two or three substituents independently selected from halogen, C2-C6 alkenyl, C2-C6 alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted straight or branched C1-C6 alkyl, C3-C6 cycloalkyl, heterocyclyl and aryl, wherein R4, R5, R6, R7, R8, R9 and R10 are as defined above.

The term "halogen" indicates fluorine, chlorine, bromine or iodine.

The term "C2-C6 alkenyl" indicates an aliphatic C2-C6 hydrocarbon chain containing at least one carbon-carbon double bond and which can be straight or branched.

Representative examples include, but are not limited to, ethenyl, 1-propenyl, 2-propenyl, 1- or 2-butenyl, and the like.

The term "C2-C6 alkynyl" indicates an aliphatic C2-C6 hydrocarbon chain containing at least one carbon-carbon double bond and which can be straight or branched.

Representative examples include, but are not limited to, ethynyl, 1-propynyl, 2-propynyl, 1- or 2-butynyl, and the like.

The term "cyano" indicates a —CN residue.

The term "nitro" indicates a —NO2 group.

The term "pharmaceutically acceptable salt" of compounds of formula (I) refers to those salts that retain the biological effectiveness and properties of the parent compound.

Such salts include acid addition salts with inorganic acids such as hydrochloric, hydrobromic, nitric, phosphoric, sulfuric, perchloric acid and the like, or with organic acids such as acetic, trifluoroacetic, propionic, glycolic, lactic, (D) or (L) malic, maleic, methanesulfonic, ethanesulfonic, benzoic, p-toluenesulfonic, salicylic, cinnamic, mandelic, tartaric, citric, succinic, malonic acid and the like; salts formed when an acidic proton present in a compound of formula (I) is either replaced by a metal ion, e.g., an alkali metal ion such as sodium or potassium, or an alkaline earth ion such as calcium or magnesium, or coordinates with an organic base such as ethanolamine, diethanolamine, triethanolamine, tromethamine, N-methylglucamine, and the like.

Compounds of formula (I) wherein X is —CH2—, are represented by the general formula (IA):

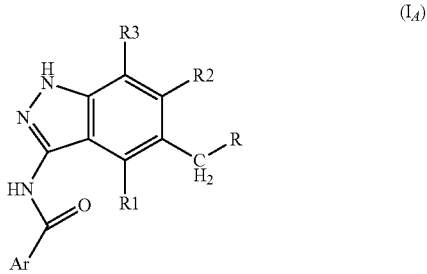

(I_A)

Compounds of formula (I) wherein X is —CH(OH)—, are represented by the general formula (IB):

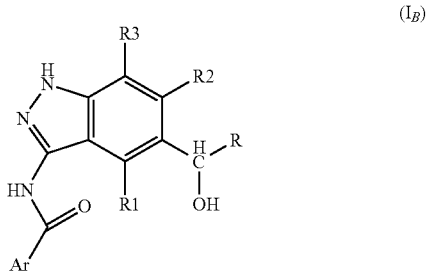

(I_B)

Compounds of formula (I) wherein X is —CH(OR')—, are represented by the general formula (IC):

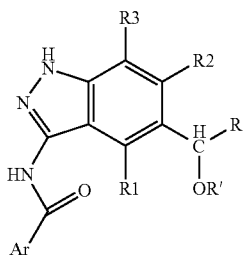

Compounds of formula (I) wherein X is —C(R'R")—, are represented by the general formula (ID):

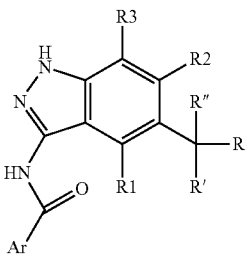

In some embodiments, the class of compounds of formula (I) are the compounds wherein: X is —CH2—, —CH(OH)—, —CH(OR')— or —C(R'R")—, wherein R' is C1-C3 alkyl and R" is hydrogen or C1-C3 alkyl; R is an optionally substituted C3-C6 cycloalkyl, heterocyclyl, aryl or heteroaryl, and R1, R2 and R3 are independently hydrogen, halogen or hydroxy.

In some embodiments, the class of compounds of formula (I) are the compounds wherein: X is —CH2—, —CH(OH)—, —CH(OR')— or —C(R'R")—, wherein R' is methyl and R" is hydrogen or methyl, and R1, R2 and R3 are hydrogen.

In some embodiments, the class of compounds of formula (I) are the compounds wherein R is an optionally substituted aryl or heteroaryl.

In some embodiments, the class of compounds of formula (I) are the compounds wherein Ar is a group of formula:

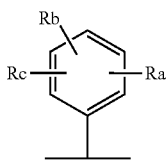

Ra, Rb and Rc are independently hydrogen, halogen, C2-C6 alkenyl, C2-C6 alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted straight or branched C1-C6 alkyl, C3-C6 cycloalkyl, heterocyclyl, aryl or heteroaryl, wherein R4, R5, R6, R7, R8, R9 and R10 are as defined above and R is an optionally substituted aryl.

In some embodiments, the class of compounds of formula (I) are the compounds wherein: Ar is a group of formula:

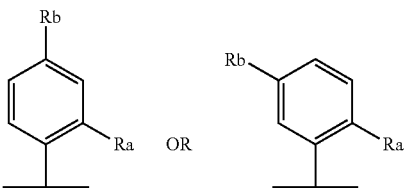

Ra and Rb are as defined above.

In some embodiments, the class of compounds of formula (I) are the compounds wherein: •Ar is a group of formula:

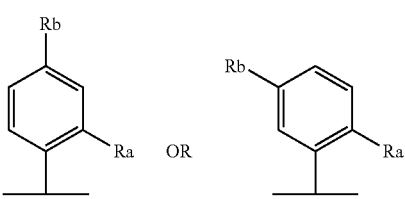

Ra is hydrogen, halogen, nitro, NHCOR4 or NR5R6 and Rb is hydrogen, nitro, NR5R6, OR7 or R8R9N—C1-C6 alkyl wherein R4, R5, R6, R7, R8 and R9 are as defined above.

Specific compounds (cpd.) of the invention are listed below:
1. N-(5-benzyl-1H-indazol-3-yl)-4-(4-methyl-piperazin-1-yl)-benzamide;
2. N-[5-(3-fluoro-benzyl)-1H-indazol-3-yl]-4-(4-methyl-piperazin-1-yl) -benzamide;
3. N-[5-(2,5-difluoro-benzyl)-1H-indazol-3-yl]-4-(4-methyl-piperazin-1-yl)benzamide;
4. N-[5-(3,5-difluoro-benzyl)-1H-indazol-3-yl]-4-(4-methyl-piperazin-1-yl)benzamide;
5. N-[5-(3-fluoro-benzyl)-1H-indazol-3-yl]-4-(4-methyl-piperazin-1-yl)-2-nitrobenzamide;
6. N-[5-(3,5-difluoro-benzyl)-1H-indazol-3-yl]-4-(4-methyl-piperazin-1-yl)-2-nitro-benzamide;
7. 2-Amino-N-[5-(3-fluoro-benzyl)-1H- indazol-3-yl]-4-(4-methyl-piperazin-1-yl) -benzamide;
8. 2-Amino-N-[5-(3,5-difluoro-benzyl)-1H- indazol-3-yl]-4-(4-methyl-piperazin-1-yl)-benzamide;
9. N-[5-(3-fluoro-benzyl)-1H-indazol-3-yl]-4-(4-methyl-piperazin-1-yl)-2-(tetrahydro-pyran-4-ylamino)-benzamide;
10. N-[5-(2,5-difluoro-benzyl)-1H-indazol-3-yl]-4-(4-methyl-piperazin-1-yl)-2-(tetrahydro-pyran-4-ylamino)-benzamide;
11. N-[5-(3,5-difluoro-benzyl)-1H-indazol-3-yl]-4-(4-methyl-piperazin-1-yl)-2-(tetrahydro-pyran-4-ylamino)-benzamide;
12. N-[5-(3-fluoro-benzyl)-1H-indazol-3-yl]-4-(4-methyl-piperazin-1-yl)-2-(1-methyl-piperidin-4-ylamino)-benzamide;
13. N-[5-(3,5-difluoro-benzyl)-1H-indazol-3-yl]-4-(4-methyl-piperazin-1-yl)-2-(1-methyl-piperidin-4-ylamino)-benzamide;
14. N-[5-(3-fluoro-benzyl)-1H-indazol-3-yl]-2-(2-methoxy-1-methoxymethyl -ethylamino)-4-(4-methyl-piperazin-1-yl)-benzamide:
15. N-[5-(2,5-difluoro-benzyl)-1H-indazol-3-yl]-2-(2-methoxy-1-methoxymethyl -ethylamino)-4-(4-methyl-piperazin-1-yl)-benzamide;
16. N-[5-(3,5-difluoro-benzyl)-1H-indazol-3-yl]-2-(2-methoxy-1-methoxymethyl -ethylamino)-4-(4-methyl-piperazin-1-yl)-benzamide;

17. 2-cyclohexylamino-N-[5-(3-fluoro-benzyl)-1H-indazol-3-yl]-4-(4-methyl-piperazin-1-yl)-benzamide;
18. 2-cyclohexylamino-N-[5-(3,5-difluoro-benzyl)-1H-indazol-3-yl]-4-(4-methyl-piperazin-1-yl)-benzamide;
19. N-[5-(3-fluoro-benzyl)-1H-indazol-3-yl]-2-(4-hydroxy-cyclohexylamino)-4-(4-methyl-piperazin-1-yl)-benzamide;
20. N-[5-(3,5-difluoro-benzyl)-1H-indazol-3-yl]-2-(4-hydroxy-cyclohexylamino)-4-(4-methyl-piperazin-1-yl)-benzamide;
21. N-[5-(3-fluoro-benzyl)-1H-indazol-3-yl]-2-isobutylamino-4-(4-methyl-piperazin-1-yl)-benzamide;
22. N-[5-(3,5-difluoro-benzyl)-1H-indazol-3-yl]-2-isobutylamino-4-(4-methyl-piperazin-1-yl)-benzamide;
23. 2-benzylamino-N-[5-(3-fluoro-benzyl)-1H-indazol-3-yl]-4-(4-methyl-piperazin-1-yl)-benzamide;
24. 2-benzylamino-N-[5-(3,5-difluoro-benzyl)-1H-indazol-3-yl]-4-(4-methyl-piperazin-1-yl)-benzamide;
25. N-[5-(3-fluoro-benzyl)-1H-indazol-3-yl]-2-(2-methoxy-ethylamino)-4-(4-methyl-piperazin-1-yl)-benzamide;
26. N-[5-(3,5-difluoro-benzyl)-1H-indazol-3-yl]-2-(2-methoxy-ethylamino)-4-(4-methyl-piperazin-1-yl)-benzamide;
27. N-[5-(3-fluoro-benzyl)-1H-indazol-3-yl]-2-(2-methoxy-1-methyl-ethylamino)-4-(4-methyl-piperazin-1-yl)-benzamide;
28. N-[5-(3,5-difluoro-benzyl)-1H-indazol-3-yl]-2-(2-methoxy-1-methyl-ethylamino)-4-(4-methyl-piperazin-1-yl)-benzamide;
29. N-[5-(3-fluoro-benzyl)-1H-indazol-3-yl]-2-((S)-2-methoxy-1-methyl-ethylamino)-4-(4-methyl-piperazin-1-yl)-benzamide;
30. N-[5-(3,5-difluoro-benzyl)-1H-indazol-3-yl]-2-((S)-2-methoxy-1-methyl-ethylamino)-4-(4-methyl-piperazin-1-yl)-benzamide;
31. N-[5-(3-fluoro-benzyl)-1H-indazol-3-yl]-2-((R)-2-methoxy-1-methyl-ethylamino)-4-(4-methyl-piperazin-1-yl)-benzamide;
32. N-[5-(3,5-difluoro-benzyl)-1H-indazol-3-yl]-2-((R)-2-methoxy-1-methyl-ethylamino)-4-(4-methyl-piperazin-1-yl)-benzamide;
33. N-[5-(3-fluoro-benzyl)-1H-indazol-3-yl]-2-(2-methoxy-1,1-dimethyl-ethylamino)-4-(4-methyl-piperazin-1-yl)-benzamide;
34. N-[5-(3,5-difluoro-benzyl)-1H-indazol-3-yl]-2-(2-methoxy-1,1-dimethyl-ethylamino)-4-(4-methyl-piperazin-1-yl)-benzamide;
35. N-[5-(3-fluoro-benzyl)-1H-indazol-3-yl]-2-(3-methoxy-propylamino)-4-(4-methyl-piperazin-1-yl)-benzamide;
36. N-[5-(3,5-difluoro-benzyl)-1H-indazol-3-yl]-2-(3-methoxy-propylamino)-4-(4-methyl-piperazin-1-yl)-benzamide;
37. N-[5-(3-fluoro-benzyl)-1H-indazol-3-yl]-2-(2-fluoro-ethylamino)-4-(4-methyl-piperazin-1-yl)-benzamide;
38. N-[5-(3,5-difluoro-benzyl)-1H-indazol-3-yl]-2-(2-fluoro-ethylamino)-4-(4-methyl-piperazin-1-yl)-benzamide;
39. N-[5-(3-fluoro-benzyl)-1H-indazol-3-yl]-2-(3-fluoro-propylamino)-4-(4-methyl-piperazin-1-yl)-benzamide;
40. N-[5-(3,5-difluoro-benzyl)-1H-indazol-3-yl]-2-(3-fluoro-propylamino)-4-(4-methyl-piperazin-1-yl)-benzamide;
41. N-[5-(3-fluoro-benzyl)-1H-indazol-3-yl]-4-(4-methyl-piperazin-1-yl)-2-phenylamino-benzamide;
42. N-[5-(3,5-difluoro-benzyl)-1H-indazol-3-yl]-4-(4-methyl-piperazin-1-yl)-2-phenylamino-benzamide;
43. 1H-pyrrole-2-carboxylic acid [2-[5-(3-fluoro-benzyl)-1H-indazol-3-ylcarbamoyl]-5-(4-methyl-piperazin-1-yl)-phenyl]-amide;
44. 1H-pyrrole-2-carboxylic acid [2-[5-(3,5-difluoro-benzyl)-1H-indazol-3-ylcarbamoyl]-5-(4-methyl-piperazin-1-yl)-phenyl]-amide;
45. 1H-pyrrole-3-carboxylic acid [2-[5-(3-fluoro-benzyl)-1H-indazol-3-ylcarbamoyl]-5-(4-methyl-piperazin-1-yl)-phenyl]-amide;
46. 1H-pyrrole-3-carboxylic acid [2-[5-(3,5-difluoro-benzyl)-1H-indazol-3-ylcarbamoyl]-5-(4-methyl-piperazin-1-yl)-phenyl]-amide;
47. N-[5-(3-fluoro-benzyl)-1H-indazol-3-yl]-2-methanesulfonylamino-4-(4-methyl-piperazin-1-yl)-benzamide;
48. N-[5-(3,5-difluoro-benzyl)-1H-indazol-3-yl]-2-methanesulfonylamino-4-(4-methyl-piperazin-1-yl)-benzamide;
49. 2-fluoro-N-[5-(3-fluoro-benzyl)-1H-indazol-3-yl]-5-(tetrahydro-pyran-4-ylamino)-benzamide;
50. N-[5-(3,5-difluoro-benzyl)-1H-indazol-3-yl]-2-fluoro-5-(tetrahydro-pyran-4-ylamino)-benzamide;
51. 2-fluoro-N-[5-(3-fluoro-benzyl)-1H-indazol-3-yl]-5-(2-methoxy-ethylamino)-benzamide;
52. N-[5-(3,5-difluoro-benzyl)-1H-indazol-3-yl]-2-fluoro-5-(2-methoxy-ethylamino)-benzamide;
53. 4-[(3-dimethylamino-propyl)-methyl-amino]-N-[5-(3-ethoxy-benzyl)-1H-indazol-3-yl]-2-nitro-benzamide;
54. 2-amino-4-[(3-dimethylamino-propyl)-methyl-amino]-N-[5-(3-ethoxy-benzyl)-1H-indazol-3-yl]-benzamide;
55. N-[5-(3,5-difluoro-benzyl)-1H-indazol-3-yl]-4-[(3-dimethylamino-propyl)-methyl-amino]-2-(tetrahydro-pyran-4-ylamino)-benzamide;
56. N-[5-(3,5-difluoro-benzyl)-1H-indazol-3-yl]-4-[(3-dimethylamino-propyl)-methyl-amino]-2-(2-methoxy-1-methoxymethyl-ethylamino)-benzamide;
2-amino-N-[5-(3,5-difluoro-benzyl)-1H-indazol-3-yl]-4-[(3-dimethylamino-propyl)-methyl-amino]-benzamide;
58. N-[5-(3,5-difluoro-benzyl)-1H-indazol-3-yl]-4-[(3-dimethylamino-propyl)-methyl-amino]-benzamide;
59. N-[5-(3,5-difluoro-benzyl)-1H-indazol-3-yl]-4-[(3-dimethylamino-propyl)-methyl-amino]-2-nitro-benzamide;
60. N-{5-[(3,5-difluoro-phenyl)-hydroxy-methyl]-1H-indazol-3-yl}-4-(4-methyl-piperazin-1-yl)-2-(tetrahydro-pyran-4-ylamino)-benzamide;
61. N-{5-[(3,5-difluoro-phenyl)-hydroxy-methyl]-1H-indazol-3-yl}-2-(2-methoxy-1-methoxymethyl-ethylamino)-4-(4-methyl-piperazin-1-yl)-benzamide;
62. N-{5-[(3,5-difluoro-phenyl)-hydroxy-methyl]-1H-indazol-3-yl}-4-(4-methyl-piperazin-1-yl)-benzamide;
63. N-{5-[(3,5-difluoro-phenyl)-hydroxy-methyl]-1H-indazol-3-yl}-2-(2-methoxy-ethylamino)-4-(4-methyl-piperazin-1-yl)-benzamide;
64. N-{5-[(3,5-difluoro-phenyl)-hydroxy-methyl]-1H-indazol-3-yl}-2-(3-methoxy-propylamino)-4-(4-methyl-piperazin-1-yl)-benzamide;
65. N-{5-[(3,5-difluoro-phenyl)-hydroxy-methyl]-1H-indazol-3-yl}-2-(2-methoxy-1,1-dimethyl-ethylamino)-4-(4-methyl-piperazin-1-yl)-benzamide;
66. N-{5-[(3,5-difluoro-phenyl)-hydroxy-methyl]-1H-indazol-3-yl}-2-(2-fluoro-ethylamino)-4-(4-methyl-piperazin-1-yl)-benzamide;
67. N-{5-[(3-ethoxy-phenyl)-hydroxy-methyl]-1H-indazol-3-yl}-4-(4-methyl-piperazin-1-yl)-2-nitro-benzamide;
68. N-{5-[(3,5-difluoro-phenyl)-methoxy-methyl]-1H-indazol-3-yl}-4-(4-methyl-piperazin-1-yl)-2-(tetrahydro-pyran-4-ylamino)-benzamide;

69. N-{5-[(3,5-difluoro-phenyl)-methoxy-methyl]-1H-indazol-3-yl}-2-(2-methoxy-1-methoxymethyl-ethylamino)-4-(4-methyl-piperazin-1-yl)-benzamide;

70. N-{5-[(3,5-difluoro-phenyl)-methoxy-methyl]-1H-indazol-3-yl}-4-(4-methyl-piperazin-1-yl)-benzamide;

71. N-{5-[(3,5-difluoro-phenyl)-methoxy-methyl]-1H-indazol-3-yl}-2-(2-methoxy-ethylamino)-4-(4-methyl-piperazin-1-yl)-benzamide;

72. N-{5-[(3,5-difluoro-phenyl)-methoxy-methyl]-1H-indazol-3-yl}-2-(3-methoxy-propylamino)-4-(4-methyl-piperazin-1-yl)-benzamide;

73. N-{5-[(3,5-difluoro-phenyl)-methoxy-methyl]-1H-indazol-3-yl}-2-(2-methoxy-1,1-dimethyl-ethylamino)-4-(4-methyl-piperazin-1-yl)-benzamide;

74. N-{5-[(3,5-difluoro-phenyl)-methoxy-methyl]-1H-indazol-3-yl}-2-(2-fluoro-ethylamino)-4-(4-methyl-piperazin-1-yl)-benzamide;

75. N-{5-[(3,5-difluoro-phenyl)-ethyl]-1H-indazol-3-yl}-4-(4-methyl-piperazin-1-yl)-2-(tetrahydro-pyran-4-ylamino)-benzamide;

76. N-{5- [1-(3,5-difluoro-phenyl)-ethyl]-1H-indazol-3-yl}-2-(2-methoxy-1-methoxymethyl-ethylamino)-4-(4-methyl-piperazin-1-yl)-benzamide;

77. N-{5-[(3,5-difluoro-phenyl)-ethyl]-1H-indazol-3-yl}-4-(4-methyl-piperazin-1-yl)-benzamide;

78. N-{5-[(3,5-difluoro-phenyl)-ethyl]-1H-indazol-3-yl}-2-(2-methoxy-ethylamino)-4-(4-methyl-piperazin-1-yl)-benzamide;

79. N-{5-[(3,5-difluoro-phenyl)-ethyl]-1H-indazol-3-yl}-2-(3-methoxy-propylamino)-4-(4-methyl-piperazin-1-yl)-benzamide;

80. N-{5-[(3,5-difluoro-phenyl)-ethyl]-1H-indazol-3-yl}-2-(2-methoxy-1,1-dimethyl-ethylamino)-4-(4-methyl-piperazin-1-yl)-benzamide;

81. N-{5-[(3,5-difluoro-phenyl)-ethyl]-1H-indazol-3-yl}-2-(2-fluoro-ethylamino)-4-(4-methyl-piperazin-1-yl)-benzamide;

82. N-{5-[1-(3,5-difluoro-phenyl)-1-methyl-ethyl]-1H-indazol-3-yl}-4-(4-methyl-piperazin-1-yl)-2-(tetrahydro-pyran-4-ylamino)-benzamide;

83. N-{5-[1-(3,5-difluoro-phenyl)-1-methyl-ethyl]-1H-indazol-3-yl}-2-(2-methoxy-1-methoxymethyl-ethylamino)-4-(4-methyl-piperazin-1-yl)-benzamide;

84. N-{5-[1-(3,5-difluoro-phenyl)-1-methyl-ethyl]-1H-indazol-3-yl}-4-(4-methyl-piperazin-1-yl)-benzamide;

85. N-{5-[1-(3,5-difluoro-phenyl)-1-methyl-ethyl]-1H-indazol-3-yl}-2-(2-methoxy-ethylamino)-4-(4-methyl-piperazin-1-yl)-benzamide;

86. N-{5-[1-(3,5-difluoro-phenyl)-1-methyl-ethyl]-1H-indazol-3-yl}-2-(3-methoxy-propylamino)-4-(4-methyl-piperazin-1-yl)-benzamide;

87. N-{5-[1-(3,5-difluoro-phenyl)-1-methyl-ethyl]-1H-indazol-3-yl}-2-(2-methoxy-1,1-dimethyl-ethylamino)-4-(4-methyl-piperazin-1-yl)-benzamide;

88. N-{5-[1-(3,5-difluoro-phenyl)-1-methyl-ethyl]-1H-indazol-3-yl}-2-(2-fluoro-ethylamino)-4-(4-methyl-piperazin-1-yl)-benzamide;

89. N-[5-(3,5-difluorobenzyl)-1H-indazol-3-yl]-4-(4-methyl-1,4-diazepan-1-yl)-2-(tetrahydro-2H-pyran-4-ylamino)benzamide;

90. N-[5-(3,5-Difluoro-benzyl)-1H-indazol-3-yl]-4-[(2-dimethylamino-ethyl)-methyl-amino]-2-(tetrahydro-pyran-4-ylamino)-benzamide;

91. N-[5-(3,5-difluorobenzyl)-1H-indazol-3-yl]-4-[4-(dimethylamino)piperidin-1-yl]-2-(tetrahydro-2H-pyran-4-ylamino)benzamide;

92. N-[5-(3,5-difluorobenzyl)-1H-indazol-3-yl]-4-[(2S)-2-(pyrrolidin-1-ylmethyl)pyrrolidin-1-yl]-2-(tetrahydro-2H-pyran-4-ylamino)benzamide;

93. N-[5-(3,5-difluorobenzyl)-1H-indazol-3-yl]-3-(4-methylpiperazin-1-yl)benzamide;

94. N-[5-(3,5-difluorobenzyl)-1H-indazol-3-yl]-4-{[(2S)-1-methylpyrrolidin-2-yl]methoxy}-2-(tetrahydro-2H-pyran-4-ylamino)benzamide;

95. N-[5-(3,5-difluorobenzyl)-1H-indazol-3-yl]-4-[(1-methylpiperidin-4-yl)oxy]-2-(tetrahydro-2H-pyran-4-ylamino)benzamide;

96. N-[5-(3,5-difluorobenzyl)-1H-indazol-3-yl]-4-[2-(dimethylamino)ethoxy]-2-(tetrahydro-2H-pyran-4-ylamino)benzamide;

97. N-[5-(3,5-difluorobenzyl)-1H-indazol-3-yl]-4-{[(3S)-1-methylpyrrolidin-3-yl]oxy}-2-(tetrahydro-2H-pyran-4-ylamino)benzamide;

98. N-[5-(3,5-difluorobenzyl)-1H-indazol-3-yl]-4-(piperazin-1-yl)-2-(tetrahydro-2H-pyran-4-ylamino)benzamide;

99. N-[5-(3,5-difluorobenzyl)-1H-indazol-3-yl]-4-(4-methylpiperazin-1-yl)-2-{[cis-4-(trifluoromethyl)cyclohexyl]amino}benzamide;

100. N-[5-(3,5-difluorobenzyl)-1H-indazol-3-yl]-4-(4-methylpiperazin-1-yl)-2-{[trans-4-(trifluoromethyl)cyclohexyl]amino}benzamide;

101. N-[5-(3,5-difluorobenzyl)-1H-indazol-3-yl]-2-fluoro-4-(4-methylpiperazin-1-yl)benzamide;

102. N-[5-(3,5-difluorobenzyl)-1H-indazol-3-yl]-1-(piperidin-4-yl)-1H-pyrazole-4-carboxamide;

103. N-[5-(3,5-difluorobenzyl)-1H-indazol-3-yl]-2-[(cis-4-hydroxycyclohexyl)amino]-4-(4-methylpiperazin-1-yl)benzamide;

104. N-[5-(3,5-difluorobenzyl)-1H-indazol-3-yl]-2-[(trans-4-hydroxycyclohexyl)amino]-4-(4-methylpiperazin-1-yl)benzamide;

105. N-[5-(3,5-difluorobenzyl)-1H-indazol-3-yl]-2-[(2-hydroxyethyl)amino]-4-(4-methylpiperazin-1-yl)benzamide;

106. 2-[(azetidin-3-ylmethyl)amino]-N-[5-(3,5-difluorobenzyl)-1H-indazol-3-yl]-4-(4-methylpiperazin-1-yl)benzamide;

107. N-[5-(3,5-difluorobenzyl)-1H-indazol-3-yl]-2-{[(1-methylazetidin-3-yl)methyl]amino}-4-(4-methylpiperazin-1-yl)benzamide;

108. N-[5-(3,5-difluorobenzyl)-1H-indazol-3-yl]-4-[(1-methylpiperidin-4-yl)amino]-2-[tetrahydro-2H-pyran-4-ylamino]benzamide;

109. 4-[(azetidin-3-ylmethyl)amino]-N-[5-(3,5-difluorobenzyl)-1H-indazol-3-yl]-2-(tetrahydro-2H-pyran-4-ylamino)benzamide;

110. N-[5-(3,5-difluorobenzyl)-1H-indazol-3-yl]-2-[(1-methylpiperidin-4-yl)amino]benzamide;

111. N-[5-(3,5-difluorobenzyl)-1H-indazol-3-yl]-2-[(1-methylpiperidin-4-yl)amino]-4-(morpholin-4-yl)benzamide;

112. N-[5-(3,5-difluorobenzyl)-1H-indazol-3-yl]-2-methoxy-4-(4-methylpiperazin-1-yl)benzamide;

113. N-[5-(3,5-difluorobenzyl)-1H-indazol-3-yl]-5-(4-methylpiperazin-1-yl)-3-(tetrahydro-2H-pyran-4-ylamino)pyridine-2-carboxamide;

114. N-[5-(3,5-difluorobenzyl)-1H-indazol-3-yl]-6-(4-methylpiperazin-1-yl)-2-(tetrahydro-2H-pyran-4-ylamino)pyridine-3-carboxamide;

115. 1-[4-{[5-(3,5-difluorobenzyl)-1H-indazol-3-yl]carbamoyl}-3-(tetrahydro-2H-pyran-4-ylamino)benzyl]piperidine;

116. N-[5-(3,5-difluorobenzyl)-1H-indazol-3-yl]-4-{[(2-methoxyethyl)(methyl)amino]methyl}-2-(tetrahydro-2H-pyran-4-ylamino)benzamide;
117. N-[5-(3,5-difluorobenzyl)-1H-indazol-3-yl]-4-(pyrrolidin-1-ylmethyl)-2-(tetrahydro-2H-pyran-4-ylamino)benzamide;
118. N-[5-(3,5-difluorobenzyl)-1H-indazol-3-yl]-4-(morpholin-4-ylmethyl)-2-(tetrahydro-2H-pyran-4-ylamino)benzamide;
119. 4-(azetidin-1-ylmethyl)-N-[5-(3,5-difluorobenzyl)-1H-indazol-3-yl]-2-(tetrahydro-2H-pyran-4-ylamino)benzamide;
120. N-[5-(3,5-Difluoro-benzyl)-1H-indazol-3-yl]-2-fluoro-5-(4-methyl-piperazin-1-ylmethyl)-benzamide;
121. N-[5-(3,5-difluorobenzyl)-1H-indazol-3-yl]-2-fluoro-5-{[(2S)-2-(pyrrolidin-1-ylmethyl)pyrrolidin-1-yl]methyl}benzamide;
122. N-[5-(3,5-difluorobenzyl)-1H-indazol-3-yl]-2-fluoro-5-(morpholin-4-ylmethyl)benzamide;
123. N-[5-(3,5-Difluoro-benzyl)-1H-indazol-3-yl]-2-fluoro-5-((S)-2-pyrrolidin-1-ylmethyl-pyrrolidine-1-carbonyl)-benzamide;
124. N-[5-(3,5-difluorobenzyl)-1H-indazol-3-yl]-4-{[(2R)-2-(pyrrolidin-1-ylmethyl)pyrrolidin-1-yl]carbonyl}benzamide;
125. N-[5-(3,5-difluorobenzyl)-1H-indazol-3-yl]-4-{[(2S)-2-(pyrrolidin-1-ylmethyl)pyrrolidin-1-yl]carbonyl}benzamide;
126. N-[5-(3,5-difluorobenzyl)-1H-indazol-3-yl]-4-{[4-(pyrrolidin-1-yl)piperidin-1-yl]carbonyl}benzamide;
127. N-[5-(3,5-difluorobenzyl)-1H-indazol-3-yl]-4-{[(2S)-2-(pyrrolidin-1-ylmethyl)pyrrolidin-1-yl]carbonyl}-2-(tetrahydro-2H-pyran-4-ylamino)benzamide;
128. N-[5-(3,5-difluorobenzyl)-1H-indazol-3-yl]-4-{[(2R)-2-(pyrrolidin-1-ylmethyl)pyrrolidin-1-yl]carbonyl}-2-(tetrahydro-2H-pyran-4-ylamino)benzamide;
129. N1-[5-(3,5-difluorobenzyl)-1H-indazol-3-yl]-N4-[2-(dimethylamino)ethyl]-N4-methyl-2-(tetrahydro-2H-pyran-4-ylamino)benzene-1,4-dicarboxamide;
130. N-[5-(3,5-difluorobenzyl)-1H-indazol-3-yl]-4-{[4-(propan-2-yl)piperazin-1-yl]carbonyl}-2-(tetrahydro-2H-pyran-4-ylamino)benzamide;
131. N1-[5-(3,5-difluorobenzyl)-1H-indazol-3-yl]-N4-[2-(dimethylamino)ethyl]-2-(tetrahydro-2H-pyran-4-ylamino)benzene-1,4-dicarboxamide;
132. N-[5-(3,5-difluorobenzyl)-1H-indazol-3-yl]-4-[(4-methylpiperazin-1-yl)carbonyl]-2-(tetrahydro-2H-pyran-4-ylamino)benzamide;
133. N-[5-(3,5-difluorobenzyl)-1H-indazol-3-yl]-4-{[4-(dimethylamino)piperidin-1-yl]carbonyl}-2-(tetrahydro-2H-pyran-4-ylamino)benzamide;
134. N1-[5-(3,5-difluorobenzyl)-1H-indazol-3-yl]-N4-(1-methylpiperidin-4-yl)-2-(tetrahydro-2H-pyran-4-ylamino)benzene-1,4-dicarboxamide;
135. N-[5-(2-methyl-5-fluoro-benzyl)-1H-indazol-3-yl]-4-(4-methyl-piperazin-1-yl)-2-(tetrahydro-pyran-4-ylamino)-benzamide;
136. 4-(4-methylpiperazin-1-yl)-N-[5-(pyridin-3-ylmethyl)-1H-indazol-3-yl]-2-(tetrahydro-2H-pyran-4-ylamino)benzamide;
137. N-[5-benzyl-1H-indazol-3-yl]-4-(4-methyl-piperazin-1-yl)-2-(tetrahydro-pyran-4-ylamino)-benzamide;
138. ethyl 4-{[2-{[5-(3,5-difluorobenzyl)-1H-indazol-3-yl]carbamoyl}-5-(4-methylpiperazin-1-yl)phenyl]amino}piperidine-1-carboxylate;
139. N-[5-(3,5-difluorobenzyl)-1H-indazol-3-yl]-4-(4-methylpiperazin-1-yl)-2-(piperidin-4-ylamino)benzamide;
140. ethyl 5-(3,5-difluorobenzyl)-3-({[4-(4-methylpiperazin-1-yl)-2-(tetrahydro-2H-pyran-4-ylamino)phenyl]carbonyl}amino)-1H-indazole-1-carboxylate;
141. N-[5-(3,5-difluoro-benzyl)-1H-indazol-3-yl]-2-((S)-2-methoxy-1-methyl-ethylamino)-4-(4-methyl-piperazin-1-yl)-benzamide;
142. N-[5-(3,5-difluorobenzyl)-1H-indazol-3-yl]-4-[(2R)-2-(pyrrolidin-1-ylmethyl)pyrrolidin-1-yl]-2-(tetrahydro-2H-pyran-4-ylamino)benzamide;
143. N-[5-(3,5-difluorobenzyl)-1H-indazol-3-yl]-4-{[(2R)-1-methylpyrrolidin-2-yl]methoxy}-2-(tetrahydro-2H-pyran-4-ylamino)benzamide;
144. N-[5-(3,5-difluorobenzyl)-1H-indazol-3-yl]-4-{[(3R)-1-methylpyrrolidin-3-yl]oxy}-2-(tetrahydro-2H-pyran-4-ylamino)benzamide;
145. N-[5-(3,5-difluorobenzyl)-1H-indazol-3-yl]-2-fluoro-5-{[(2R)-2-(pyrrolidin-1-ylmethyl)pyrrolidin-1-yl]methyl}benzamide, and
146. N-[5-(3,5-difluoro-benzyl)-1H-indazol-3-yl]-2-fluoro-5-((R)-2-pyrrolidin-1-ylmethyl-pyrrolidine-1-carbonyl)-benzamide.

In some embodiments, the compound of the invention is: N-[5-(3,5-difluoro-benzyl)-1H-indazol-3-yl]-4-(4-methyl-piperazin-1-yl)-2-(tetrahydro-pyran-4-ylamino)-benzamide.

The synthesis of the compounds of formula (I), is described in U.S. Pat. No. 8,299,057, issued Oct. 30, 2012, which is hereby incorporated by reference in its entirety. Formula 2.(I).

The compounds of formula 2.(I) may have one or more asymmetric centers, and may therefore exist as individual optical isomers or racemic mixtures. Accordingly, all the possible isomers, and their mixtures, of the compounds of formula 2.(I) are within the scope of the present invention.

Derivatives of compounds of formula 2.(I) originating from metabolism in a mammal, and the pharmaceutically acceptable bio-precursors (otherwise referred to as prodrugs) of the compounds of formula 2.(I) are also within the scope of the present invention.

In addition to the above, as known to those skilled in the art, the pyrazole ring of the compounds of formula 2.(I) rapidly equilibrates in solution to form a mixture of tautomers, as depicted below:

wherein Ar, R, R1, R2 and R3 are as defined above.

Accordingly, in the present invention, where only one tautomer is indicated for the compounds of formula 2.(I), the other tautomer 2.(Ia) is also within the scope of the present invention, unless specifically noted otherwise.

The general terms as used herein, unless otherwise specified, have the meaning reported below as applied to formula 2.(I).

The term "straight or branched C1-C6 alkyl" refers to a saturated aliphatic hydrocarbon radical, including straight chain and branched chain groups of from 1 to 6 carbon atoms, e.g. methyl, ethyl, propyl, 2-propyl, n-butyl, isobutyl, tert-butyl, pentyl and the like. The alkyl group may be substituted or unsubstituted. When substituted, the substituent groups are preferably one to three, independently selected from the group consisting of halogen, alkenyl, alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted C3-C6 cycloalkyl, heterocyclyl and aryl, wherein R4, R5, R6, R7, R8, R9 and R10 are as defined above.

The term "C3-C6 cycloalkyl" refers to a 3- to 6-membered all-carbon monocyclic ring, which may contain one or more double bonds but does not have a completely conjugated π-electron system. Examples of cycloalkyl groups, without limitation, are cyclopropyl, cyclobutyl, cyclopentyl, cyclopentenyl, cyclohexyl, cyclohexenyl and cyclohexadienyl. A cycloalkyl group may be substituted or unsubstituted. When substituted, the substituent groups are preferably one or two substituents, independently selected from the group consisting of halogen, alkenyl, alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted straight or branched C1-C6 alkyl, C3-C6 cycloalkyl, heterocyclyl and aryl, wherein R4, R5, R6, R7, R8, R9 and R10 are as defined above.

The term "heterocyclyl" refers to a 3- to 7-membered, saturated or partially unsaturated carbocyclic ring where one or more carbon atoms are replaced by heteroatoms. These heteroatoms can include, but are not limited to, nitrogen, oxygen and sulfur. Not limiting examples of heterocyclyl groups are, for instance, oxiranyl, aziridinyl, oxetanyl, azetidinyl, tetrahydrofuranyl, dihydrofuranyl, tetrahydrothiophenyl, dihydrothiophenyl, pyrrolidinyl, dihydropyrrolyl, pyranyl, dihydropyranyl, tetrahydropyranyl, tetrahydrothiopyranyl, piperidinyl, pyrazolinyl, isoxazolidinyl, isoxazolinyl, thiazolidinyl, thiazolinyl, isothiazolinyl, dioxanyl, piperazinyl, morpholinyl, thiomorpholinyl, hexamethyleneiminyl, homopiperazinyl and the like. A heterocyclyl group may be substituted or unsubstituted. When substituted, the substituent groups are preferably one or two substituents, independently selected from the group consisting of halogen, alkenyl, alkynyl, cyano, nitro, NHCOR4, COR4, NR5R6, NR5COR4, OR7, SR7, SOR10, SO2R10, NHSOR10, NHS2R10, R8R9N—C1-C6 alkyl, R8O—C1-C6 alkyl, an optionally further substituted straight or branched C1-C6 alkyl, C3-C6 cycloalkyl, heterocyclyl and aryl, wherein R4, R5, R6, R7, R8, R9 and R10 are as defined above.

The term "aryl" refers to a mono-, bi- or poly-carbocyclic as well as a heterocyclic system with from 1 to 4 rings, either fused or linked to each other by single bonds, wherein at least one of the carbocyclic or heterocyclic rings is aromatic. Not limiting examples of aryl groups are, for instance, phenyl, α- or β-naphthyl, 9,10-dihydroanthracenyl, indanyl, fluorenyl, biphenyl, pyrrolyl, furoyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzo isoxazolyl, benzothiazolyl, benzo isothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl and the like.

The term "aryl" may also refer to aromatic carbocyclic or heterocyclic rings further fused or linked to non-aromatic heterocyclic rings, typically 5- to 7-membered heterocycles. Not limiting examples of such aryl groups are, for instance, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl and the like.

The aryl group can be optionally substituted by one or more, preferably one, two, or three substituents independently selected from halogen, alkenyl, alkynyl, cyano, nitro, NHCOR4, COR4, NR5R6, NR5COR4, OR7, SR7, SOR10, SO2R10, NHSORIO, NHSO2R10, R8R9N—C1-C6 alkyl, R8O—C1-C6 alkyl, an optionally further substituted straight or branched C1-C6 alkyl, C3-C6 cycloalkyl, heterocyclyl and aryl, wherein R4, R5, R6, R7, R8, R9 and R10 are as defined above.

The term "halogen" indicates fluorine, chlorine, bromine or iodine.

The term "alkenyl" indicates straight or branched C2-C6 alkyl groups bearing a double bond. Representative examples include, but are not limited to, ethenyl, 1-propenyl, 2-propenyl, 1- or 2-butenyl, and the like.

The term "alkynyl" indicates straight or branched C2-C6 alkyl groups bearing a triple bond. Representative examples include, but are not limited to, ethynyl, 1-propynyl, 2-propynyl, 1- or 2-butynyl, and the like.

The term "cyano" indicates a —CN residue.

The term "nitro" indicates a —NO2 group.

References herein to "compounds" are meant to encompass, alternatively, pharmaceutically acceptable salts of such compounds.

The term "pharmaceutically acceptable salt" of compounds of formula 2.(I) or any other compounds referenced herein refers to those salts that retain the biological effectiveness and properties of the parent compound. Such salts include:

Acid addition salts with inorganic acids such as hydrochloric, hydrobromic, nitric, phosphoric, sulfuric, perchloric acid and the like, or with organic acids such as acetic, trifluoroacetic, propionic, glycolic, lactic, (D) or (L) malic, maleic, methanesulfonic, ethanesulfonic, benzoic, p-toluenesulfonic, salicylic, cinnamic, mandelic, tartaric, citric, succinic, malonic acid and the like; salts formed when an acidic proton present in a compound of formula 2.(I) is either replaced by a metal ion, e.g., an alkali metal ion such as sodium or potassium, or an alkaline earth ion such as calcium or magnesium, or coordinates with an organic base such as ethanolamine, diethanolamine, triethanolamine, tromethamine, N-methylglucamine, and the like.

In some embodiments, the class of compounds of formula 2.(I) are the compounds wherein: R is an optionally further substituted C3-C6 cycloalkyl, heterocyclyl or aryl and R1, R2 and R3 are independently hydrogen, halogen or hydroxy.

In some embodiments, the class of compounds of formula 2.(I) are the compounds wherein: Ar is an optionally further substituted phenyl, pyridinyl, pyrimidinyl or pyrazinyl.

In some embodiments, the compounds of formula 2.(I) are the compounds wherein: R1, R2 and R3 are hydrogen.

In some embodiments, the class of compounds of formula 2.(I) are the compounds wherein: Ar is an optionally further substituted phenyl or pyridinyl and R is an optionally further substituted aryl.

In some embodiments, the class of compounds of formula 2.(I) are the compounds wherein:

Ar is a group of formula:

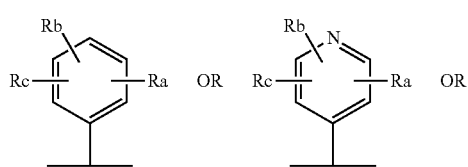

-continued

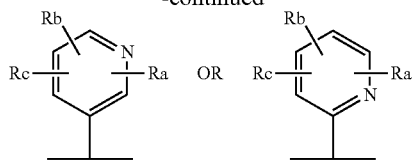

wherein Ra, Rb and Rc are independently hydrogen, halogen, alkenyl, alkynyl, cyano, nitro, NHCOR4, COR4, NR5R6, NR5COR4, OR7, SR7, SOR10, SO2R10, NHSOR10, NHSO2R10, R8R9N—C1-C6 alkyl, R8O—C1-C6 alkyl, an optionally further substituted straight or branched C1-C6 alkyl, C3-C6 cycloalkyl, heterocyclyl or aryl, wherein R4, R5, R6, R7, R8, R9 and R10 are as defined above and R is an optionally further substituted aryl.

In some embodiments, the class of compounds of formula 2.(I) are the compounds wherein: Ar is a group of formula:

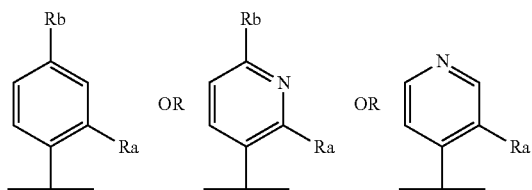

Ra and Rb are as defined above and R is an optionally further substituted aryl.

In some embodiments, the class of compounds of formula 2.(I) are the compounds wherein: Ar is a group of formula:

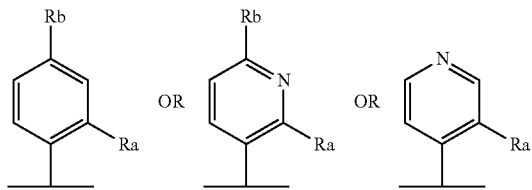

Ra is hydrogen, halogen, nitro, NHCOR4 or NR5R6 and Rb is hydrogen, nitro, NR5R6, OR7 or R8R9N—C1-C6 alkyl wherein R4, R5, R6, R7, R8 and R9 are as defined above and R is an optionally further substituted phenyl.

Some compounds (cpd.) of the invention are listed below:
1. N-(5-Benzenesulfonyl-1H-indazol-3-yl)-4-(4-methyl-piperazin-1-yl)-benzamide; 2. N-[5-(3-Fluoro-benzenesulfonyl)-1H-indazol-3-yl]-4-(4-methyl-piperazin-1-yl) -benzamide;
3. N-[5-(3,5-Difluoro-benzenesulfonyl)-1H-indazol-3-yl]-4-(4-methyl-piperazin-1-yl)-benzamide;
4. N-(5-Benzenesulfonyl-1H-indazol-3-yl)-4-(4-methyl-piperazin-1-yl)-2-nitro -benzamide;
5. N- [5-(3-Fluoro-benzenesulfonyl)-1H-indazol-3-yl]-4-(4-methyl-piperazin-1-yl) -2-nitro-benzamide;
6. N-[5-(3,5-difluoro-benzyl)-1H-indazol-3-yl]-4-(4-methyl-piperazin-1-yl)-2-nitro-benzamide;
7. 2-Amino-N-[5-(3-fluoro-benzyl)-1H- indazol-3-yl]-4-(4-methyl-piperazin-1-yl) -benzamide;
8. 2-Amino-N-[5-(3,5-difluoro-benzyl)-1H- indazol-3-yl]-4-(4-methyl -piperazin-1-yl)-benzamide;
9. 2-Amino-N-[5-(3,5-difluoro-benzyl)-1H- indazol-3-yl]-4-(4-methyl -piperazin-1-yl)-benzamide;
10. N-(5-Benzenesulfonyl-1H-indazol-3-yl)-4-(4-methyl-piperazin-1-yl)-2-(tetrahydro-pyran-4-ylamino)-benzamide;
11. N-[5-(3-Fluoro-benzenesulfonyl)-1H-indazol-3-yl]-4-(4-methyl-piperazin-1-yl)-2-(tetrahydro-pyran-4-ylamino)-benzamide;
12. N-[5-(3,5-Difluoro-benzenesulfonyl)-1H-indazol-3-yl]-4-(4-methyl-piperazin -1-yl)-2-(tetrahydro-pyran-4-ylamino)-benzamide;
13. N-[5-(3-Fluoro-benzenesulfonyl)-1H-indazol-3-yl]-2-isobutylamino-4-(4-methyl-piperazin-1-yl)-benzamide;
14. N-[5-(3,5-Difluoro-benzenesulfonyl)-1H-indazol-3-yl]-2-isobutylamino-4-(4-methyl-piperazin-1-yl)-benzamide;
15. 2-Cyclohexylamino-N-[5-(3-fluoro-benzenesulfonyl)-1H-indazol-3-yl]-4-(4-methyl-piperazin-1-yl)-benzamide;
16. 2-Cyclohexylamino-N-[5-(3,5-difluoro-benzenesulfonyl)-1H-indazol-3-yl]-4-(4-methyl-piperazin-1-yl)-benzamide;
17. N-[5-(3-Fluoro-benzenesulfonyl)-1H-indazol-3-yl]-2-(4-hydroxy -cyclohexylamino)-4-(4-methyl-piperazin-1-yl)-benzamide;
18. N-[5-(3,5-Diluoro-benzenesulfonyl)-1H-indazol-3-yl]-2-(4-hydroxy -cyclohexylamino)-4-(4-methyl-piperazin-1-ylbenzamide;
19. N-[5-(3,5-Fluoro-benzenesulfonyl)-1H-indazol-3-yl]-4-(4-methyl-piperazin-1-yl)-2-[(pyrrolidin-2-ylmethyl)-amino]-benzamide;
20. N-[5-(3,5-Difluoro-benzenesulfonyl)-1H-indazol-3-yl]-4-(4-methyl-piperazin -1-yl)-2-[(pyrrolidin-2-ylmethyl)-amino]-benzamide;
21. N-[5-(3-Fluoro-benzenesulfonyl)-1H-indazol-3-yl]-4-(4-methyl-piperazin-1-yl)-2-[(piperidin-3-ylmethyl)-amino]-benzamide;
22. N-[5-(3,5-Difluoro-benzenesulfonyl)-1H-indazol-3-yl]-4-(4-methyl-piperazin -1-yl)-2-[(piperidin-3-ylmethyl)-amino]-benzamide;
23. N-[5-(3-Fluoro-benzenesulfonyl)-1H-indazo1-3-yl]-4-(4-methyl-piperazin-1-yl)-2-[(1-methyl-pyrrolidin-2-ylmethyl)-amino]-benzamide;
24. N-[5-(3,5-Difluoro-benzenesulfonyl)-1H-indazol-3-yl]-4-(4-methyl-piperazin -1-yl)-2- [(1-methy 1-pyrrolidin-2-ylmethyl)-amino]-benzamide;
25. N-[5-(3-Fluoro-benzenesulfonyl)-1H-indazol-3-yl]-4-(4-methyl-piperazin-1-yl)-2-(piperidin-4-ylamino)-benzamide;
26. N-[5-(3,5-Difluoro-benzenesulfonyl)-1H-indazol-3-yl]-4-(4-methyl-piperazin -1-yl)-2-(piperidin-4-ylamino)-benzamide;
27. N-[5-(3-Fluoro-benzenesulfonyl)-1H-indazol-3-yl]-4-(4-methyl-piperazin-1-yl)-2-(piperidin-3-ylamino)-benzamide;
28. N-[5-(3,5-Difluoro-benzenesulfonyl)-1H-indazol-3-yl]-4-(4-methyl-piperazin -1-yl)-2-(piperidin-3-ylamino)-benzamide;
29. N-[5-(3-Fluoro-benzenesulfonyl)-1H-indazol-3-yl]-4-(4-methyl-piperazin-1-yl)-2-(tetrahydro-thiopyran-4-ylamino)-benzamide;
30. N-[5-(3,5-Difluoro-benzenesulfonyl)-1H-indazol-3-yl]-4-(4-methyl-piperazin -1-yl)-2-(tetrahydro-thiopyran-4-ylamino)-benzamide;
31. N-[5-(3-Fluoro-benzenesulfonyl)-1H-indazol-3-yl]-2-[(furan-2-ylmethyl) -amino]-4-(4-methyl-piperazin-1-yl)-benzamide;
32. N-[5-(3,5-Difluoro-benzenesulfonyl)-1H-indazol-3-yl]-2-[(furan-2-ylmethyl) -amino]-4-(4-methyl-piperazin-1-yl)-benzamide;

33. 1H-Pyrrole-2-carboxylic acid [2-(5-benzenesulfonyl-1H-indazol-3-ylcarbamoyl)-5-(4-methyl-piperazin-1-yl)-phenyl]-amide;

34. 1H-Pyrrole-2-carboxylic acid [2-[5-(3-fluoro-benzenesulfonyl)-1H-indazol-3-ylcarbamoyl]-5-(4-methyl-piperazin-1-yl)-phenyl]-amide;

35. 1H-Pyrrole-2-carboxylic acid [2-[5-(3,5-difluoro-benzenesulfonyl)-1H-indazol -3-ylcarbamoyl]-5-(4-methyl-piperazin-1-yl)-phenyl]-amide;

36. (S)-Tetrahydro-furan-2-carboxylic acid [2-(5-benzenesulfonyl-1H-indazol-3-ylcarbamoyl)-5-(4-methyl-piperazin-1-yl)-phenyl]-amide;

37. (S)-Tetrahydro-furan-2-carboxylic acid [2-[5-(3-fluoro-benzenesulfonyl)-1H -indazol-3-ylcarbamoyl]-5-(4-methyl-piperazin-1-yl)-phenyl]-amide;

38. (S)-Tetrahydro-furan-2-carboxylic acid [2-[5-(3,5-difluoro-benzenesulfonyl) -1H-indazol-3-ylcarbamoyl]-5-(4-methyl-piperazin-1-yl)-phenyl]-amide;

39. 1H-Pyrrole-3-carboxylic acid [2-(5-benzenesulfonyl-1H-indazol-3-ylcarbamoyl)-5-(4-methyl-piperazin-1-yl)-phenyl]-amide;

40. 1H-Pyrrole-3-carboxylic acid (2-[5-(3-fluoro-benzenesulfonyl)-1H-indazol-3-ylcarbamoyl]-5-(4-methyl-piperazin-1-yl)-phenylFamide;

41. 1H-Pyrrole-3-carboxylic acid [2-[5-(3,5-difluoro-benzenesulfonyl)-1H-indazol -3-ylcarbamoyl]-5-(4-methyl-piperazin-1-yl)-phenyl]-amide;

42. N-[5-(3-Fluoro-benzenesulfonyl)-1H-indazol-3-yl]-2-isobutyrylamino-4-(4-methyl-piperazin-1-yl)-benzamide;

43. N-[5-(3,5-Difluoro-benzenesulfonyl)-1H-indazol-3-yl]-2-isobutyrylamino-4-(4-methyl-piperazin-1-yl)-benzamide;

44. 2-(Cyclobutanecarbonyl-amino)-N-[5-(3-fluoro-benzenesulfonyl)-1H-indazol -3-yl]-4-(4-methyl-piperazin-1-yl)-benzamide;

45. 2-(Cyclobutanecarbonyl-amino)-N-[5-(3,5-difluoro-benzenesulfonyl)-1H -indazol-3-yl]-4-(4-methyl-piperazin-1-yl)-benzamide;

46. 2-(2-Amino-acetylamino)-N-[5-(3-fluoro-benzenesulfonyl)-1H-indazol-3-yl]-4-(4-methyl-piperazin-1-yl)-benzamide;

47. 2-(2-Amino-acetylamino)-N-[5-(3,5-difluoro-benzenesulfonyl)-1H-indazol-3-yl]-4-(4-methyl-piperazin-1-yl)-benzamide;

48. N-[5-(3-Fluoro-benzenesulfonyl)-1H-indazol-3-yl]-2-(2-methylamino -acetylamino)-4-(4-methyl-piperazin-1-yl)-benzamide;

49. N-[5-(3,5-Difluoro-benzenesulfonyl)-1H-indazol-3-yl]-2-(2-methylamino -acetylamino)-4-(4-methyl-piperazin-1-yl)-benzamide;

50. 2-(2-Dimethylamino-acetylamino)-N-[5-(3-fluoro-benzenesulfonyl)-1H -indazol-3-yl]-4-(4-methyl-piperazin-1-yl)-benzamide;

51. N-[5-(3,5-Difluoro-benzenesulfonyl)-1H-indazol-3-yl]-2-(2-dimethylamino -acetylamino)-4-(4-methyl-piperazin-1-yl)-benzamide;

52. 2-((S)-2-Amino-propionylamino)-N-[5-(3-fluoro-benzenesulfonyl)-1H-indazol -3-yl]-4-(4-methyl-piperazin-1-yl)-benzamide;

53. 2-((S)-2-Amino-propionylamino)-N-[5-(3,5-difluoro-benzenesulfonyl)-1H -indazol-3-yl]-4-(4-methyl-piperazin-1-yl)-benzamide;

54. (S)-Pyrrolidine-2-carboxylic acid [2-[5-(3-fluoro-benzenesulfonyl)-1H-indazol -3-ylcarbamoyl]-5-(4-methyl-piperazin-1-yl)-phenyl]-amide;

55. (S)-Pyrrolidine-2-carboxylic acid [2-[5-(3,5-difluoro-benzenesulfonyl)-1H -indazol-3-ylcarbamoyl]-5-(4-methyl-piperazin-1-yl)-phenyl]-amide;

56. Piperidine-2-carboxylic acid [2-[5-(3-fluoro-benzenesulfonyl)-1H-indazol-3-ylcarbamoyl]-5-(4-methyl-piperazin-1-yl)-phenyl]-amide;

57. Piperidine-2-carboxylic acid [2-[5-(3,5-difluoro-benzenesulfonyl)-1H-indazol -3-ylcarbamoyl]-5-(4-methyl-piperazin-1-yl)-phenyl]-amide;

58. Piperidine-3-carboxylic acid [2-[5-(3-fluoro-benzenesulfonyl)-1H-indazol-3-ylcarbamoyl]-5-(4-methyl-piperazin-1-yl)-phenyl]-amide;

59. Piperidine-3-carboxylic acid [2-[5-(3,5-difluoro-benzenesulfonyl)-1H-indazol -3-ylcarbamoyl]-5-(4-methyl-piperazin-1-yl)-phenyl]-amide;

60. Piperidine-4-carboxylic acid [2-[5-(3-fluoro-benzenesulfonyl)-1H-indazol-3-ylcarbamoyl]-5-(4-methyl-piperazin-1-yl)-phenyl]-amide;

61. Piperidine-4-carboxylic acid [2-[5-(3,5-difluoro-benzenesulfonyl)-1H-indazol -3-ylcarbamoyl]-5-(4-methyl-piperazin-1-yl)-phenyl]-amide;

62. (R)-Tetrahydro-furan-2-carboxylic acid [2-[5-(3,5-difluoro-benzenesulfonyl) -1H-indazol-3-ylcarbamoyl]-5-(4-methyl-piperazin-1-yl)-phenyl]-amide;

63. Tetrahydro-furan-3-carboxylic acid [2-[5-(3,5-difluoro-benzenesulfonyl)-1H -indazol-3-ylcarbamoyl]-5-(4-methyl-piperazin-1-yl)-phenyl]-amide;

64. Tetrahydro-pyran-4-carboxylic acid [2-[5-(3,5-difluoro-benzenesulfonyl)-1H -indazol-3-ylcarbamoyl]-5-(4-methyl-piperazin-1-yl)-phenyl]-amide;

65. Pyridine-2-carboxylic acid [2-(5-benzenesulfonyl-1H-indazol-3-ylcarbamoyl) -5-(4-methyl-piperazin-1-yl)-phenyl]-amide;

66. Pyridine-2-carboxylic acid [2-[5-(3-fluoro-benzenesulfonyl)-1H-indazol-3-ylcarbamoyl]-5-(4-methyl-piperazin-1-yl)-phenyl]-amide;

67. Pyridine-2-carboxylic acid [2-[5-(3,5-difluoro-benzenesulfonyl)-1H-indazol-3-ylcarbamoyl]-5-(4-methyl-piperazin-1-yl)-phenyl]-amide; 68. 3H-Imidazole-4-carboxylic acid [2-(5-benzenesulfonyl-1H-indazol-3-ylcarbamoyl)-5-(4-methyl-piperazin-1-yl)-phenyl]-amide;

69. 3H-Imidazole-4-carboxylic acid [2-[5-(3-fluoro-benzenesulfonyl)-1H-indazol -3-ylcarbamoyl]-5-(4-methyl-piperazin-1-yl)-phenyl]-amide;

70. 3H-Imidazole-4-carboxylic acid [2-[5-(3,5-difluoro-benzenesulfonyl)-1H -indazol-3-ylcarbamoyl]-5-(4-methyl-piperazin-1-yl)-phenyl]-amide;

71. 1-Methyl-1H-pyrrole-2-carboxylic acid [2-(5-benzenesulfonyl-1H-indazol-3-ylcarbamoyl)-5-(4-methyl-piperazin-1-yl)-phenyl]-amide;

72. 1-Methyl-IH-pyrrole-2-carboxylic acid [2-[5-(3-fluoro-benzenesulfonyl)-1H -indazol-3-ylcarbamoyl]-5-(4-methyl-piperazin-1-yl)-phenyl]-amide;

73. 1-Methyl-1H-pyrrole-2-carboxylic acid [2-[5-(3,5-difluoro-benzenesulfonyl) -1H-indazol-3-ylcarbamoyl]-5-(4-methyl-piperazin-1-yl)-phenyl]-amide;

74. Furan-2-carboxylic acid [2-[5-(3-fluoro-benzenesulfonyl)-1H-indazol-3-ylcarbamoyl]-5-(4-methyl-piperazin-1-yl)-phenyl]-amide;

75. Furan-2-carboxylic acid [2-[5-(3,5-difluoro-benzenesulfonyl)-1H-indazol-3-ylcarbamoyl]-5-(4-methyl-piperazin-1-yl)-phenyl]-amide;

76. 5-Methyl- isoxazole-4-carboxylic acid [2-(5-benzenesulfonyl-1H-indazol-3-ylcarbamoyl)-5-(4-methyl-piperazin-1-yl)-phenyl]-amide;

77. 5-Methyl-isoxazole-4-carboxylic acid [2-[5-(3-fluoro-benzenesulfonyl)-1H-indazol-3-ylcarbamoyl]-5-(4-methyl-piperazin-1-yl)-phenyl]-amide;

78. 5-Methyl-isoxazole-4-carboxylic acid [2-[5-(3,5-difluoro-benzenesulfonyl)-1H-indazol-3-ylcarbamoyl]-5-(4-methyl-piperazin-1-yl)-phenyl]-amide;

79. N-(5-Benzenesulfonyl-1H-indazol-3-yl)-2-benzoylamino-4-(4-methyl-piperazin-1-yl)-benzamide;

80. 2-Benzoylamino-N-[5-(3-fluoro-benzenesulfonyl)-1H-indazol-3-yl]-4-(4-methyl-piperazin-1-yl)-benzamide;

81. 2-Benzoylamino-N-[5-(3,5-difluoro-benzenesulfonyl)-1H-indazol-3-yl]-4-(4-methyl-piperazin-1-yl)-benzamide;

82. N-[5-(3-Chloro-benzenesulfonyl)-1H-indazol-3-yl]-4-(4-methyl-piperazin-1-yl)-2-(tetrahydro-pyran-4-ylamino)-benzamide;

83. N-[5-(3-Methoxy-benzenesulfonyl)-1H-indazol-3-yl]-4-(4-methyl-piperazin-1-yl)-2-(tetrahydro-pyran-4-ylamino)-benzamide;

84. N-[5-(3,5-Dichloro-benzenesulfonyl)-1H-indazol-3-yl]-4-(4-methyl-piperazin-1-yl)-2-(tetrahydro-pyran-4-ylamino)-benzamide;

85. N-[5-(3-Fluoro-5-methoxy-benzenesulfonyl)-1H-indazol-3-yl]-4-(4-methyl-piperazin-1-yl)-2-(tetrahydro-pyran-4-ylamino)-benzamide;

86. N-[5-(3-Fluoro-benzenesulfonyl)-1H-indazol-3-yl]-2-(tetrahydro-pyran-4-ylamino)-benzamide;

87. N-[5-(3,5-Difluoro-benzenesulfonyl)-1H-indazol-3-yl]-2-(tetrahydro-pyran-4-ylamino)-benzamide;

88. 4-Fluoro-N-[5-(3-fluoro-benzenesulfonyl)-1H-indazol-3-yl]-2-(tetrahydro-pyran-4-ylamino)-benzamide;

89. N-[5-(3,5-Difluoro-benzenesulfonyl)-1H-indazol-3-yl]-4-fluoro-2-(tetrahydro-pyran-4-ylamino)-benzamide;

90. N-[5-(3-Fluoro-benzenesulfonyl)-1H-indazol-3-yl]-4-methoxy-2-(tetrahydro-pyran-4-ylamino)-benzamide;

91. N-[5-(3,5-Difluoro-benzenesulfonyl)-1H-indazol-3-yl]-4-methoxy-2-(tetrahydro-pyran-4-ylamino)-benzamide;

92. 4-Dimethylamino-N-[5-(3-fluoro-benzenesulfonyl)-1H-indazol-3-yl]-2-(tetrahydro-pyran-4-ylamino)-benzamide;

93. N-[5-(3,5-Difluoro-benzenesulfonyl)-1H-indazol-3-yl]-4-dimethylamino-2-(tetrahydro-pyran-4-ylamino)-benzamide;

94. N-[5-(3-Fluoro-benzenesulfonyl)-1H-indazol-3-yl]-4-morpholin-4-yl-2-(tetrahydro-pyran-4-ylamino)-benzamide;

95. N-[5-(3,5-Difluoro-benzenesulfonyl)-1H-indazol-3-yl]-4-morpholin-4-yl-2-(tetrahydro-pyran-4-ylamino)-benzamide;

96. N-[5-(3-Fluoro-benzenesulfonyl)-1H-indazol-3-yl]-4-piperazin-1-yl-2-(tetrahydro-pyran-4-ylamino)-benzamide;

97. N-[5-(3,5-Difluoro-benzenesulfonyl)-1H-indazol-3-yl]-4-piperazin-1-yl-2-(tetrahydro-pyran-4-ylamino)-benzamide;

98. 4-(4-Ethyl-piperazin-1-yl)-N-[5-(3-fluoro-benzenesulfonyl)-1H-indazol-3-yl]-2-(tetrahydro-pyran-4-ylamino)-benzamide;

99. N-[5-(3,5-Difluoro-benzenesulfonyl)-1H-indazol-3-yl]-4-(4-ethyl-piperazin-1-yl)-2-(tetrahydro-pyran-4-ylamino)-benzamide;

100. N-[5-(3-Fluoro-benzenesulfonyl)-1H-indazol-3-yl]-4-(4-propyl-piperazin-1-yl)-2-(tetrahydro-pyran-4-ylamino)-benzamide;

101. N-[5-(3,5-Difluoro-benzenesulfonyl)-1H-indazol-3-yl]-4-(4-propyl-piperazin-1-yl)-2-(tetrahydro-pyran-4-ylamino)-benzamide;

102. N-[5-(3-Fluoro-benzenesulfonyl)-1H-indazol-3-yl]-4-(4-isopropyl-piperazin-1-yl)-2-(tetrahydro-pyran-4-ylamino)-benzamide;

103. N-[5-(3,5-Difluoro-benzenesulfonyl)-1H-indazol-3-yl]-4-(4-isopropyl-piperazin-1-yl)-2-(tetrahydro-pyran-4-ylamino)-benzamide;

104. N-[5-(3-Fluoro-benzenesulfonyl)-1H-indazol-3-yl]-4-(4-methyl-[1,4]diazepan-1-yl)-2-(tetrahydro-pyran-4-ylamino)-benzamide;

105. N-[5-(3,5-Difluoro-benzenesulfonyl)-1H-indazol-3-yl]-4-(4-methyl-[1,4]diazepan-1-yl)-2-(tetrahydro-pyran-4-ylamino)-benzamide;

106. 4-(4-Ethyl-[1,4]diazepan-1-yl)-N-[5-(3-fluoro-benzenesulfonyl)-1H-indazol-3-yl]-2-(tetrahydro-pyran-4-ylamino)-benzamide;

107. N-[5-(3,5-Difluoro-benzenesulfonyl)-1H-indazol-3-yl]-4-(4-ethyl-[1,4]diazepan-1-yl)-2-(tetrahydro-pyran-4-ylamino)-benzamide;

108. 4-(2-Dimethylamino-ethoxy)-N-[5-(3-fluoro-benzenesulfonyl)-1H-indazol-3-yl]-2-(tetrahydro-pyran-4-ylamino)-benzamide;

109. N-[5-(3,5-Difluoro-benzenesulfonyl)-1H-indazol-3-yl]-4-(2-dimethylamino-ethoxy)-2-(tetrahydro-pyran-4-ylamino)-benzamide;

110. N-[5-(3-Fluoro-benzenesulfonyl)-1H-indazol-3-yl]-4-(2-pyrrolidin-1-yl-ethoxy)-2-(tetrahydro-pyran-4-ylamino)-benzamide;

111. N-[5-(3,5-Difluoro-benzenesulfonyl)-1H-indazol-3-yl]-4-(2-pyrrolidin-1-yl-ethoxy)-2-(tetrahydro-pyran-4-ylamino)-benzamide;

112. N-[5-(3-Fluoro-benzenesulfonyl)-1H-indazol-3-yl]-4-(1-methyl-piperidin-4-yloxy)-2-(tetrahydro-pyran-4-ylamino)-benzamide;

113. N-[5-(3,5-Difluoro-benzenesulfonyl)-1H-indazol-3-yl]-4-(1-methyl-piperidin-4-yloxy)-2-(tetrahydro-pyran-4-ylamino)-benzamide;

114. 4-Dimethylaminomethyl-N-[5-(3-fluoro-benzenesulfonyl)-1H-indazol-3-yl]-2-(tetrahydro-pyran-4-ylamino)-benzamide;

115. N-[5-(3,5-Difluoro-benzenesulfonyl)-1H-indazol-3-yl]-4-dimethylaminomethyl-2-(tetrahydro-pyran-4-ylamino)-benzamide;

116. N-[5-(3-Fluoro-benzenesulfonyl)-1H-indazol-3-yl]-4-pyrrolidin-1-ylmethyl-2-(tetrahydro-pyran-4-ylamino)-benzamide;

117. N-[5-(3,5-Difluoro-benzenesulfonyl)-1H-indazol-3-yl]-4-pyrrolidin-1-ylmethyl-2-(tetrahydro-pyran-4-ylamino)-benzamide;

118. N-[5-(3-Fluoro-benzenesulfonyl)-1H-indazol-3-yl]-4-piperidin-1-ylmethyl-2-(tetrahydro-pyran-4-ylamino)-benzamide;

119. N-[5-(3,5-Difluoro-benzenesulfonyl)-1H-indazol-3-yl]-4-piperidin-1-ylmethyl-2-(tetrahydro-pyran-4-ylamino)-benzamide;

120. N-[5-(3-Fluoro-benzenesulfonyl)-1H-indazol-3-yl]-4-morpholin-4-ylmethyl-2-(tetrahydro-pyran-4-ylamino)-benzamide;

121. N-[5-(3,5-Difluoro-benzenesulfonyl)-1H-indazol-3-yl]-4-morpholin-4-ylmethyl-2-(tetrahydro-pyran-4-ylamino)-benzamide;

122. N-[5-(3-Fluoro-benzenesulfonyl)-1H-indazol-3-yl]-4-(1-methyl-piperidin-4-ylamino)-2-(tetrahydro-pyran-4-ylamino)-benzamide;

123. N-[5-(3,5-Difluoro-benzenesulfonyl)-1H-indazol-3-yl]-4-(1-methyl-piperidin-4-ylamino)-2-(tetrahydro-pyran-4-ylamino)-benzamide;

124. N-[5-(3-Fluoro-benzenesulfonyl)-1H-indazol-3-yl]-2,4-bis-(tetrahydro-pyran -4-ylamino)-benzamide;
125. N-[5-(3,5-Difluoro-benzenesulfonyl)-1H-indazol-3-yl]-2,4-bis-(tetrahydro -pyran-4-ylamino)-benzamide;
126. 4-(2-Dimethylamino-1-methyl-ethylamino)-N-[5-(3-fluoro-benzenesulfonyl) -1H-indazol-3-yl]-2-(tetrahydro-pyran-4-ylamino)-benzamide;
127. N-[5-(3,5-Difluoro-benzenesulfonyl)-1H-indazol-3-yl]-4-(2-dimethylamino-1-methyl-ethylamino)-2-(tetrahydro-pyran-4-ylamino)-benzamide;
128. 4-(2-Diethylamino-1-methyl-ethylamino)-N-[5-(3-fluoro-benzenesulfonyl) -1H-indazol-3-yl]-2-(tetrahydro-pyran-4-ylamino)-benzamide;
129. 4-(2-Diethylamino-1-methyl-ethylamino)-N-[5-(3,5-difluoro -benzenesulfonyl)-1H-indazol-3-yl]-2-(tetrahydro-pyran-4-ylamino)-benzamide;
130. 4-(2-Dimethylamino-ethylamino)-N-[5-(3-fluoro-benzenesulfonyl)-1H -indazol-3-yl]-2-(tetrahydro-pyran-4-ylamino)-benzamide;
131. N-[5-(3,5-Difluoro-benzenesulfonyl)-1H-indazol-3-yl]-4-(2-dimethylamino -ethylamino)-2-(tetrahydro-pyran-4-ylamino)-benzamide;
132. 4-[(2-Dimethylamino-ethyl)-methyl-amino]-N-[5-(3-fluoro-benzenesulfonyl) -1H-indazol-3-yl]-2-(tetrahydro-pyran-4-ylamino)-benzamide;
133. N-[5-(3,5-Difluoro-benzenesulfonyl)-1H-indazol-3-yl]-4-[(2-dimethylamino -ethyl)-methyl-amino]-2-(tetrahydro-pyran-4-ylamino)-benzamide;
134. N-[5-(3-Fluoro-benzenesulfonyl)-1H-indazol-3-yl]-4-{[2-(isopropyl-methyl -amino)-ethyl]-methyl-amino}-2-(tetrahydro-pyran-4-ylamino)-benzamide;
135. N-[5-(3,5-Difluoro-benzenesulfonyl)-1H-indazol-3-yl]-4-{[2-(isopropyl -methyl-amino)-ethyl]-methyl-amino}-2-(tetrahydro-pyran-4-ylamino)-benzamide;
136. N-[5-(3-Fluoro-benzenesulfonyl)-1H-indazol-3-yl]-4-[methyl-(2-piperidin-1-yl-ethyl)-amino]-2-(tetrahydro-pyran-4-ylamino)-benzamide;
137. N-[5-(3,5-Difluoro-benzenesulfonyl)-1H-indazol-3-yl]-4-[methyl-(2-piperidin-1-yl-ethyl)-amino]-2-(tetrahydro-pyran-4-ylamino)-benzamide;
138. N-[5-(3-Fluoro-benzenesulfonyl)-1H-indazol-3-yl]-4-[methyl-(2-morpholin-4-yl-ethyl)-amino]-2-(tetrahydro-pyran-4-ylamino)-benzamide;
139. N-[5-(3,5-Difluoro-benzenesulfonyl)-1H-indazol-3-yl]-4-[methyl-(2-morpholin-4-yl-ethyl)-amino]-2-(tetrahydro-pyran-4-ylamino)-benzamide;
140. 4-[(2-Dimethylamino-ethyl)-ethyl-amino]-N-[5-(3-fluoro-benzenesulfonyl) -1H-indazol-3-yl]-2-(tetrahydro-pyran-4-ylamino)-benzamide;
141. N-[5-(3,5-Difluoro-benzenesulfonyl)-1H-indazol-3-yl]-4-[(2-dimethylamino -ethyl)-ethyl-amino]-2-(tetrahydro-pyran-4-ylamino)-benzamide;
142. 4-[(3-Dimethylamino-propyl)-methyl-amino]-N-[5-(3-fluoro -benzenesulfonyl)-1H-indazol-3-yl]-2-(tetrahydro-pyran-4-ylamino)-benzamide;
143. N-[5-(3,5-Difluoro-benzenesulfonyl)-1H-indazol-3-yl]-4-[(3-dimethylamino -propyl)-methyl-amino]-2-(tetrahydro-pyran-4-ylamino)-benzamide;
144. 4-(4-Dimethylamino-piperidin-1-yl)-N-[5-(3-fluoro-benzenesulfonyl)-1H -indazol-3-yl]-2-(tetrahydro-pyran-4-ylamino)-benzamide;
145. N-[5-(3,5-Difluoro-benzenesulfonyl)-1H-indazol-3-yl]-4-(4-dimethylamino -piperidin-1-yl)-2-(tetrahydro-pyran-4-ylamino)-benzamide;
146. N-[5-(3-Fluoro-benzenesulfonyl)-1H-indazol-3-yl]-4-pyrrolidin-1-yl -piperidin-1-yl)-2-(tetrahydro-pyran-4-ylamino)-benzamide;
147. N-[5-(3,5-Difluoro-benzenesulfonyl)-1H-indazol-3-yl]-4-(4-pyrrolidin-1-yl -piperidin-1-yl)-2-(tetrahydro-pyran-4-ylamino)-benzamide;
148. N-[5-(3-Fluoro-benzenesulfonyl)-1H-indazol-3-yl]-4-[methyl-(1-methyl -pyrrolidin-3-yl)-amino]-2-(tetrahydro-pyran-4-ylamino)-benzamide;
149. N-[5-(3,5-Difluoro-benzenesulfonyl)-1H-indazol-3-yl]-4-[methyl-(1-methyl -pyrrolidin-3-yl)-amino]-2-(tetrahydro-pyran-4-ylamino)-benzamide;
150. N-[5-(3,5-Difluoro-benzenesulfonyl)-1H-indazol-3-yl]-2-(2-methoxy -ethylamino)-4-(4-methyl-piperazin-1-yl)-benzamide;
151. N-[5-(3-Fluoro-benzenesulfonyl)-1H-indazol-3-yl]-2-(2-methoxy -ethylamino)-4-(4-methyl-piperazin-1-yl)-benzamide;
152. N-[5-(3,5-Difluoro-benzenesulfonyl)-1H-indazol-3-yl]-4-[(2-dimethylamino -ethyl)-methyl-amino]-2-(2-methoxy-ethylamino)-benzamide;
153. 4-[(2-Dimethylamino-ethyl)-methyl-amino]-N-[5-(3-fluoro-benzenesulfonyl) -1H-indazol-3-yl]-2-(2-methoxy-ethylamino)-benzamide;
154. N-[5-(3,5-Difluoro-benzenesulfonyl)-1H-indazol-3-yl]-4-[(3-dimethylamino -propyl)-methyl-amino]-2-(2-methoxy-ethylamino)-benzamide;
155. 4-[(3-Dimethylamino-propyl)-methyl-amino]-N-[5-(3-fluoro -benzenesulfonyl)-1H-indazol-3-yl]-2-(2-methoxy-ethylamino)-benzamide;
156. N-[5-(3,5-Difluoro-benzenesulfonyl)-1H-indazol-3-yl]-4-[(2-dimethylamino -1-methyl-ethyl)-methyl-amino]-2-(2-methoxy-ethylamino)-benzamide;
157. 4-[(2-Dimethylamino-1-methyl-ethyl)-methyl-amino]-N-[5-(3-fluoro -benzenesulfonyl)-1H-indazol-3-yl]-2-(2-methoxy-ethylamino)-benzamide;
158. N-[5-(3,5-Difluoro-benzenesulfonyl)-1H-indazol-3-yl]-2-(2-methoxy-1-methyl-ethylamino)-4-(4-methyl-piperazin-1-yl)-benzamide;
159. N-[5-(3-Fluoro-benzenesulfonyl)-1H-indazol-3-yl]-2-(2-methoxy-1-methyl -ethylamino)-4-(4-methyl-piperazin-1-yl)-benzamide;
160. N-[5-(3,5-Difluoro-benzenesulfonyl)-1H-indazol-3-yl]-4-[(2-dimethylamino -ethyl)-methyl-amino]-2-(2-methoxy-1-methyl-ethylamino)-benzamide;
161. 4-[(2-Dimethylamino-ethyl)-methyl-amino]-N-[5-(3-fluoro-benzenesulfonyl) -1H- indazol-3-yl]-2-(2-methoxy-1-methyl-ethylamino)-benzamide;
162. N-[5-(3,5-Difluoro-benzenesulfonyl)-1H-indazol-3-yl]-4-[(3-dimethylamino -propyl)-methyl-amino]-2-(2-methoxy-1-methyl-ethylamino)-benzamide;
163. 4-[(3-Dimethylamino-propyl)-methyl-amino]-N-[5-(3-fluoro -benzenesulfonyl)-1H-indazol-3-yl]-2-(2-methoxy-1-methyl-ethylamino)-benzamide;
164. N-[5-(3,5-Difluoro-benzenesulfonyl)-1H-indazol-3-yl]-4-[(2-dimethylamino -1-methyl-ethyl)-methyl-amino]-2-(2-methoxy-1-methyl-ethylamino)-benzam ide;
165. 4-[(2-Dimethylamino-1-methyl-ethyl)-methyl-amino]-N-[5-(3-fluoro -benzenesulfonyl)-1H-indazol-3-yl]-2-(2-methoxy-1-methyl-ethylamino)-benzamide;
166. N-[5-(3,5-Difluoro-benzenesulfonyl)-1H-indazol-3-yl]-4-dimethylaminomethyl-2-(2-methoxy-1-methyl-ethyl-amino)-benzamide;
167. N-[5-(3,5-Difluoro-benzenesulfonyl)-1H-indazol-3-yl]-2-((S)-2-methoxy-1-methyl-ethylamino)-4-(4-methyl-piperazin-1-yl)-benzamide;
168. N-[5-(3-Fluoro-benzenesulfonyl)-1H-indazol-3-yl]-2-((S)-2-methoxy-1-methyl-ethylamino)-4-(4-methyl-piperazin-1-yl)-benzamide;

169. N-[5-(3,5-Difluoro-benzenesulfonyl)-1H-indazol-3-yl]-4-[(2-dimethylamino -ethyl)-methyl-amino]-2-((S)-2-methoxy-1-methyl-ethylamino)-benzamide;

170. 4-[(2-Dimethylamino-ethyl)-methyl-amino]-N-[5-(3-fluoro-benzenesulfonyl) -1H-indazol-3-yl]-2-((S)-2-methoxy-1-methyl-ethylamino)-benzamide;

171. N-[5-(3,5-Difluoro-benzenesulfonyl)-1H-indazol-3-yl]-4-[(3-dimethylamino -propyl)-methyl-amino]-2-((S)-2-methoxy-1-methyl-ethylamino)-benzamide;

172. 4-[(3-Dimethylamino-propyl)-methyl-amino]-N-[5-(3-fluoro -benzenesulfonyl)-1H-indazol-3-yl]-2-(S)-2-methoxy-1-methyl-ethylamino)-benzamide;

173. N-[5-(3,5-Difluoro-benzenesulfonyl)-1H-indazol-3-yl]-4-[(2-dimethylamino -1-methyl-ethyl)-methyl-amino]-2-(S)-2-methoxy-1-methyl-ethylamino)-benzamide;

174. 4-[(2-Dimethylamino-1-methyl-ethyl)-methyl-amino]-N-[5-(3-fluoro -benzenesulfonyl)-1H-indazol-3-yl]-2-((S)-2-methoxy-1-methyl-ethylamino)-benzamide;

175. N-[5-(3,5-Difluoro-benzenesulfonyl)-1H-indazol-3-yl]-2-((R)-2-methoxy-1-methyl-ethylamino)-4-(4-methyl-piperazin-1-yl)-benzamide;

176. N-[5-(3-Fluoro-benzenesulfonyl)-1H-indazol-3-yl]-2-((R)-2-methoxy-1-methyl-ethylamino)-4-(4-methyl-piperazin-1-yl)-benzamide;

177. N-[5-(3,5-Difluoro-benzenesulfonyl)-1H-indazol-3-yl]-4-[(2-dimethylamino -ethyl)-methyl-amino]-2-((R)-2-methoxy-1-methyl-ethylamino)-benzamide;

178. 4-[(2-Dimethylamino-ethyl)-methyl-amino]-N-[5-(3-fluoro-benzenesulfonyl) -1H-indazol-3-yl]-2-((R)-2-methoxy-1-methyl-ethylamino)-benzamide;

179. N-[5-(3,5-Difluoro-benzenesulfonyl)-1H-indazol-3-yl]-4-[(3-dimethylamino -propyl)-methyl-amino]-2-((R)-2-methoxy-1-methyl-ethylamino)-benzamide;

180. 4-[(3-Dimethylamino-propyl)-methyl-amino]-N-[5-(3-fluoro -benzenesulfonyl)-1H-indazol-3-yl]-2-((R)-2-methoxy-1-methyl-ethylamino)-benzamide;

181. N-[5-(3,5-Difluoro-benzenesulfonyl)-1H-indazol-3-yl]-4-[(2-dimethylamino -1-methyl-ethyl)-methyl-amino]-2-((R)-2-methoxy-1-methyl-ethylamino)-benzamide;

182. 4-[(2-Dimethylamino-1-methyl-ethyl)-methyl-amino]-N-[5-(3-fluoro -benzenesulfonyl)-1H-indazol-3-yl]-2-((R)-2-methoxy-1-methyl-ethylamino)-benzamide;

183. N-[5-(3,5-Difluoro-benzenesulfonyl)-1H-indazol-3-yl]-2-(2-methoxy-1-methoxymethyl-ethylamino)-4-(4-methyl-piperazin-1-yl)-benzamide;

184. N-[5-(3-Fluoro-benzenesulfonyl)-1H-indazol-3-yl]-2-(2-methoxy-1-methoxymethyl-ethylamino)-4-(4-methyl-piperazin-1-yl)-benzamide;

185. N-[5-(3,5-Difluoro-benzenesulfonyl)-1H-indazol-3-yl]-4-[(2-dimethylamino -ethyl)-methyl-amino]-2-(2-methoxy-1-methoxymethyl-ethylamino)-benzamide;

186. 4-[(2-Dimethylamino-ethyl)-methyl-amino]-N-[5-(3-fluoro-benzenesulfonyl) -1H-indazol-3-yl]-2-(2-methoxy-1-methoxymethyl-ethylamino)-benzamide;

187. N-[5-(3,5-Difluoro-benzenesulfonyl)-1H-indazol-3-yl]-4-[(3-dimethylamino -propyl)-methyl-amino]-2-(2-methoxy-1-methoxymethyl-ethylamino)-benzamide;

188. 4-[(3-Dimethylamino-propyl)-methyl-amino]-N-[5-(3-fluoro -benzenesulfonyl)-1H-indazol-3-yl]-2-(2-methoxy-1-methoxymethyl-ethylamino) -benzamide;

189. N-[5-(3,5-Difluoro-benzenesulfonyl)-1H-indazol-3-yl]-4-[(2-dimethylamino -1-methyl-ethyl)-methyl-amino]-2-(2-methoxy-1-methoxymethyl-ethylamino)-benzamide;

190. 4-[(2-Dimethylamino-1-methyl-ethyl)-methyl-amino]-N-[5-(3-fluoro -benzenesulfonyl)-1H-indazol-3-yl]-2-(2-methoxy-1-methoxymethyl-ethylamino) -benzamide;

191. N-[5-(3-Fluoro-benzenesulfonyl)-1H-indazol-3-yl]-2-(2-methoxy-1,1-dimethyl-ethylamino)-4-(4-methyl-piperazin-1-yl)-benzamide;

192. N-[5-(3,5-Difluoro-benzenesulfonyl)-1H- indazol-3-yl]-2-(2-methoxy-1,1-dimethyl-ethylamino)-4-(4-methyl-piperazin-1-yl)-benzamide;

193. N-[5-(3-Fluoro-benzenesulfonyl)-1H-indazol-3-yl]-2-((R)-3-methoxy-1-methyl-propylamino)-4-(4-methyl-piperazin-1-yl)-benzamide;

194. N-[5-(3,5-Difluoro-benzenesulfonyl)-1H-indazol-3-yl]-2-((R)-3-methoxy-1-methyl-propylamino)-4-(4-methyl-piperazin-1-yl)-benzamide;

195. N-[5-(3-Fluoro-benzenesulfonyl)-1H-indazol-3-yl]-2-((R)-1-methoxymethyl -propylamino)-4-(4-methyl-piperazin-1-yl)-benzamide;

196. N-[5-(3,5-Difluoro-benzenesulfonyl)-1H-indazol-3-yl]-2-((R)-1-methoxymethyl-propylamino)-4-(4-methyl-piperazin-1-yl)-benzamide;

197. 2-Fluoro-N-[5-(3-fluoro-benzenesulfonyl)-1H-indazol-3-yl]-6-(tetrahydro -pyran-4-ylamino)-benzamide;

198. N-[5-(3,5-Difluoro-benzenesulfonyl)-1H-indazol-3-yl]-2-fluoro-6-(tetrahydro -pyran-4-ylamino)-benzamide;

199. 2-Fluoro-N-[5-(3-fluoro-benzenesulfonyl)-1H-indazol-3-yl]-4-(4-methyl -piperazin-1-yl)-6-(tetrahydro-pyran-4-ylamino)-benzamide;

200. N-[5-(3,5-Difluoro-benzenesulfonyl)-1H-indazol-3-yl]-2-fluoro-4-(4-methyl -piperazin-1-yl)-6-(tetrahydro-pyran-4-ylamino)-benzamide;

201. N-[5-(3-Fluoro-benzenesulfonyl)-1H-indazol-3-yl]-3-(tetrahydro-pyran-4-ylamino)-isonicotinamide;

202. N-[5-(3,5-Difluoro-benzenesulfonyl)-1H-indazol-3-yl]-3-(tetrahydro-pyran-4-ylamino)-isonicotinamide;

203. N-[5-(3-Fluoro-benzenesulfonyl)-1H-indazol-3-yl]-3-(2-methoxy-1-methyl -ethylamino)-isonicotinamide;

204. N-[5-(3,5-Difluoro-benzenesulfonyl)-1H-indazol-3-yl]-3-(2-methoxy-1-methyl-ethylamino)-isonicotinamide;

205. N-[5-(3-Fluoro-benzenesulfonyl)-1H-indazol-3-yl]-2-(tetrahydro-pyran-4-ylamino)-nicotinamide;

206. N-[5-(3,5-Difluoro-benzenesulfonyl)-1H-indazol-3-yl]-2-(tetrahydro-pyran-4-ylamino)-nicotinamide;

207. N-[5-(3-Fluoro-benzenesulfonyl)-1H-indazol-3-yl]-6-(4-methyl-piperazin-1-yl)-2-(tetrahydro-pyran-4-ylamino)-nicotinamide;

208. N-[5-(3,5-Difluoro-benzenesulfonyl)-1H-indazol-3-yl]-6-(4-methyl-piperazin -1-yl)-2-(tetrahydro-pyran-4-ylamino)-nicotinamide;

209. N-[5-(3-Fluoro-benzenesulfonyl)-1H-indazol-3-yl]-3-[(1H-pyrrole-2-carbonyl)-amino]-isonicotinamide;

210. N-[5-(3,5-Difluoro-benzenesulfonyl)-1H-indazol-3-yl]-3-[(1H-pyrrole-2-carbonyl)-amino]-isonicotinamide;

211. N-[5-(3-Fluoro-benzenesulfonyl)-1H-indazol-3-yl]-2-[(1H-pyrrole-2-carbonyl)-amino]-nicotinamide;

212. N-[5-(3,5-Difluoro-benzenesulfonyl)-1H-indazol-3-yl]-2-[(1H-pyrrole-2-carbonyl)-amino]-nicotinamide;

213. 3-Amino-N-[5-(3,5-difluoro-benzenesulfonyl)-1H-indazol-3-yl]-isonicotinamide;

214. N-[5-(3,5-Difluoro-benzenesulfonyl)-1H-indazol-3-yl]-4-fluoro-2-nitro -benzamide;

215. 2-Amino-N-[5-(3,5-difluoro-benzenesulfonyl)-1H-indazol-3-yl]-4-[methyl-(2-piperidin-1-yl-ethyl)-amino]-benzamide;

216. N-[5-(3,5-Difluoro-benzenesulfonyl)-1H-indazol-3-yl]-4-[(3-dimethylamino -propyl)-methyl-amino]-2-isobutylamino-benzamide;

217. N-[5-(3,5-difluoro-benzenesulfonyl)-1H-indazol-3-yl]-4-[methyl-(2-piperidin -1-yl-ethyl)-amino]-2-nitro-benzamide 218. N-[5-(3-Fluoro-benzenesulfonyl)-1H-indazol-3-yl]-4-nitro-2-(tetrahydro-pyran-4-ylamino)-benzamide;

219. N-[5-(3,5-Difluoro-benzenesulfonyl)-1H-indazol-3-yl]-4-(4-pyrrolidin-1-yl-piperidine-1-carbonyl)-benzamide;

220. N-[5-(3,5-Difluoro-benzenesulfonyl)-1H-indazol-3-yl]-4-((R)-2-pyrrolidin-1-ylmethyl-pyrrolidine-1-carbonyl)-benzamide 221. N-[5-(3,5-Difluoro-benzenesulfonyl)-1H-indazol-3-yl]-4-((S)-2-pyrrolidin-1-ylmethyl-pyrrolidine-1-carbonyl)-benzamide;

222. 1-Piperidin-4-yl-1H-pyrazole-4-carboxylic acid [5-(3,5-difluoro-benzenesulfonyl)-1H-indazol-3-yl]-amide;

223. N-[5-(3,5-Difluoro-benzenesulfonyl)-1H-indazol-3-yl]-2-(2-fluoro-ethylamino)-4-(4-methyl-piperazin-1-yl)-benzamide;

224. N-[5-(3-Fluoro-benzenesulfonyl)-1H-indazol-3-yl]-2-(2-fluoro-ethylamino)-4-(4-methyl-piperazin-1-yl)-benzamide;

225. N-(5-Benzenesulfonyl-1H-indazol-3-yl)-2-(2-fluoro-ethylamino)-4-(4-methyl-piperazin-1-yl)-benzamide;

226. N-[5-(3,5-Difluoro-benzenesulfonyl)-1H-indazol-3-yl]-2-(2-fluoro-1-fluoromethyl-ethylamino)-4-(4-methyl-piperazin-1-yl)-benzamide;

227. N-[5-(3-Fluoro-benzenesulfonyl)-1H-indazol-3-yl]-2-(2-fluoro-1-fluoromethyl-ethylamino)-4-(4-methyl-piperazin-1-yl)-benzamide and 228. N-(5-Benzenesulfonyl-1H-indazol-3-yl)-2-(2-fluoro-1-fluoromethyl-ethylamino)-4-(4-methyl-piperazin-1-yl)-benzamide.

The present invention also provides a process for the preparation of a compound of formula 2.(I).

The synthesis of the compounds of formula 2.(I), is described in U.S. Pat. No. 8,114,865, issued Feb. 14, 2012, which is hereby incorporated by reference in its entirety.

Pharmacology

The short forms and abbreviations used herein have the following meaning: Ci—Curie; DMSO—dimethylsulfoxide; ID—identity; KDa—kiloDalton; microCi—microCurie; Mg—milligram; Microg—microgram; mL—milliliter; microL—microliter; M—molar; mM—millimolar; microM—micromolar; nM—nanomolar.

Molecular Screening

Transcript accumulation levels, genomic locus screening methods, and protein kinase activity assays for ROS1, ALK, TrkA, TrkB, TrkC, or or any kinase recited herein, or a combination thereof, may be performed using methods known to one of skill in the art. Kinase assays may be performed by providing a substrate to a protein extract comprising ROS1, ALK, TrkA, TrkB, TrkC, or any kinase recited herein. ROS1, ALK, TrkA, TrkB, TrkC, or any kinase recited herein locus sequencing may be performed using, for example, whole genome shotgun sequencing, or targeted sequencing of the ROS1, ALK, TrkA, TrkB, TrkC, or any kinase recited herein locus, for example through targeted amplification of the locus or a region spanning the locus wholly or in part, using PCR techniques know to one of skill in the art and primers generated through means known to one of skill in the art, followed by sequencing of any generated amplicons. Molecular alterations can be detected by next generation sequencing (NGS), quantitative reverse-transcription polymerase chain reaction DNA amplification reactions (qPCR), fluorescence in situ hybridization (FISH), and/or immunohistochemistry (IHC) and are inclusive of gene rearrangements, single-nucleotide polymorphisms (SNPs), insertions, deletions, splice variants, gene amplifications, and aberrant RNA/protein expression.

Copy number variations (CNVs), point mutations (SNPs/SNVs), insertions, deletions, gene rearrangements, RNA/protein over expression, and constitutive phosphorylation are measurable alterations that can result in oncogenic perturbation of ROS1, ALK, TrkA, TrkB, TrkC, or any kinase recited herein, such as misregulation, upregulation, or downregulation through and including downregulation to complete loss of activity. A DNA-based test can detect CNVs, SNPs, insertions, deletions, and gene rearrangements. An RNA-based test can detect over expression, under expression (up to and including complete loss of expression) or misexpression of ROS1, ALK, TrkA, TrkB, TrkC, or any kinase recited herein mRNA and many of the alterations detected in the DNA-based test. Protein-based tests allow one to measure the over expression, under expression (through and including complete loss of expression) or misexpression of ROS1, ALK, TrkA, TrkB, TrkC, or any kinase recited herein protein; constitutive phosphorylation, constitutive dephosphorylation or misphosphorylation of the ROS1, ALK, TrkA, TrkB, TrkC, or any kinase recited herein protein; and increase, decrease (through and including complete loss) or altered activity pattern of ROS1, ALK, TrkA, TrkB, TrkC, or any kinase recited herein kinase activity.

Preparation of formulation and dosage forms comprising N-[5-(3,5-difluorobenzyl)-1H-indazol-3-yl]-4-(4-methyl-piperazin-1-yl)-2-(tetrahydro-2H-pyran-4-ylamino) benzamide.

Hard gelatin capsules comprising 50 mg, 100 mg, and 200 mg of N-[5-(3,5-difluorobenzyl)-1H-indazol-3-yl]-4-(4-methyl-piperazin-1-yl)-2-(tetrahydro-2H-pyran-4-ylamino) benzamide were prepared as follows.

The required amounts of active ingredient and excipients are weighed into the warehouse dispensing area. The weight of N-[5-(3,5-difluorobenzyl)-1H-indazol-3-yl]-4-(4-methyl-piperazin-1-yl)-2-(tetrahydro-2H-pyran-4-ylamino) benzamide and the mannitol are adjusted according to the active desired potency of the dosage form. (1) Manually pre-mix N-[5-(3,5-difluorobenzyl)-1H-indazol-3-yl]-4-(4-methyl-piperazin-1-yl)-2-(tetrahydro-2H-pyran-4-ylamino) benzamide and colloidal silicon dioxide into a polyethylene (PE) bag. (2) The resulting mixture from step 1 is passed through a 0.500 mm screen size sieve, along with a portion of the pregelatinized starch and mannitol and the resulting materials are collected in a blender. (3) The resulting mixture from step 2 is further mixed for about 20 minutes at 20-25 rpm. (4) The pregelatinized starch and magnesium stearate and are pre-mixed together and are passed through a 0.500 mm screen size sieve. (5) The material from step 4 are mixed together with the materials from step 3 and mixed for about 20 minutes at 20-25 rpm. (6) The blend resulting from step 5 is filled into hard gelatin capsules using an automatic capsule filling machine. Representative formulations of capsules comprising 50 mg, 100 mg or 200 mg of N-[5-(3,5-difluorobenzyl)-1H-indazol-3-yl]-4-(4-methyl-piperazin-1-yl)-2-(tetrahydro-2H-pyran-4-ylamino) benzamide are shown below.

| 50 mg capsule representative batch formulation | | | |
| --- | --- | --- | --- |
| Components | Function | Batch formula 50 mg (6,000 capsules) | Amount per capsule 50 mg |
| N-[5-(3,5-difluorobenzyl)-1H-indazol-3-yl]-4-(4-methyl-piperazin-1-yl)-2-(tetrahydro-2H-pyran-4-ylamino) benzamide | Active ingredient | 300 g | 50 mg |

-continued

50 mg capsule representative batch formulation

| Components | Function | Batch formula 50 mg (6,000 capsules) | Amount per capsule 50 mg |
|---|---|---|---|
| Mannitol | Filler | 255.00 g | 42.50 mg |
| Pregelatinized starch | Filler | 102.75 g | 17.125 mg |
| Colloidal silicon dioxide | Glidant | 10.50 g | 1.750 mg |
| Magnesium sterate | Lubricant | 6.75 g | 1.125 mg |
| Total | | 675.00 g | 112.50 mg |

100 mg capsule representative batch formulation

| Components | Function | Batch formula 100 mg (3,600 capsules) | Amount per capsule 100 mg |
|---|---|---|---|
| N-[5-(3,5-difluorobenzyl)-1H-indazol-3-yl]-4-(4-methyl-piperazin-1-yl)-2-(tetrahydro-2H-pyran-4-ylamino) benzamide | Active ingredient | 360.0 g | 100.00 mg |
| Mannitol | Filler | 306.00 g | 85.00 mg |
| Pregelatinized starch | Filler | 123.30 g | 34.25 mg |
| Colloidal silicon dioxide | Glidant | 12.60 g | 3.50 mg |
| Magnesium sterate | Lubricant | 8.10 g | 2.25 mg |
| Total | | 810.00 g | 225.00 mg |

200 mg capsule representative batch formulation

| Components | Function | Batch formula 200 mg (4,100 capsules) | Amount per capsule 200 mg |
|---|---|---|---|
| N-[5-(3,5-difluorobenzyl)-1H-indazol-3-yl]-4-(4-methyl-piperazin-1-yl)-2-(tetrahydro-2H-pyran-4-ylamino) benzamide | Active ingredient | 820.00 g | 200.00 mg |
| Mannitol | Filler | 697.00 g | 170.00 mg |
| Pregelatinized starch | Filler | 280.85 g | 68.50 mg |
| Colloidal silicon dioxide | Glidant | 28.70 g | 7.00 mg |
| Magnesium sterate | Lubricant | 18.45 g | 4.50 mg |
| Total | | 1845.00 g | 450.00 mg |

A dose escalation study of N-[5-(3,5-difluorobenzyl)-1H-indazol-3-yl]-4-(4-methyl-piperazin-1-yl)-2-(tetrahydro-2H-pyran-4-ylamino) benzamide was conducted in human patients with advanced solid tumors. N-[5-(3,5-difluorobenzyl)-1H-indazol-3-yl]-4-(4-methyl-piperazin-1-yl)-2-(tetrahydro-2H-pyran-4-ylamino) benzamide was dosed orally once/day in a 4 day on, 3 day off schedule for 3 weeks, followed by a 7 day rest period, in continuous 28-day cycles (Schedule A); once/day in continuous 28-day cycles (Schedule B); and once/day in a 4 day on, 3 day off schedule without interruption in continuous 28-day cycles (Schedule C). A minimum of 3 patients were enrolled at each dose level. Endpoints include safety, PK, and tumor response by response evaluation criteria in solid tumors (RECIST).

Schedule A evaluated ascending oral doses of N-[5-(3,5-difluorobenzyl)-1H- indazol-3-yl]-4-(4-methyl-piperazin-1-yl)-2-(tetrahydro-2H-pyran-4-ylamino) benzamide once daily (fasted state) in a 4-day on, 3-day off schedule for 3 weeks, followed by a 7-day rest period, in continuous 28-day cycles. Dose escalation was conducted according to the standard '3+3' scheme.

Schedule B evaluated ascending oral doses of N-[5-(3,5-difluorobenzyl)-1H-indazol-3-yl]-4-(4-methyl-piperazin-1-yl)-2-(tetrahydro-2H-pyran-4-ylamino) benzamide once daily (fed state) without rest, in continuous 28-day cycles.

Schedule C evaluated ascending oral doses of N-[5-(3,5-difluorobenzyl)-1H-indazol-3-yl]-4-(4-methyl-piperazin-1-yl)-2-(tetrahydro-2H-pyran-4-ylamino) benzamide once daily (fed state) in a 4-day on, 3-day off schedule for 4 weeks without rest, in continuous 28-day cycles.

Patients on each dosing schedule and at each dose

| Schedule | Cohort | Daily Dose Level | # of Patients |
|---|---|---|---|
| A | 1 | 100 mg/m$^2$ | 3 |
| | 2 | 200 mg/m$^2$ | 3 |
| | 3 | 400 mg/m$^2$ | 4 |
| | 4 | 800 mg/m$^2$ | 3 |
| | 5 | 1200 mg/m$^2$ | 3 |
| | 6 | 1600 mg/m$^2$ | 3 |
| B | 1 | 200 mg/m$^2$ | 3 |
| C | 1 | 400 mg/m$^2$ | 3 |

Patient cancer diagnosis and associated molecular alterations

| Primary Diagnosis | Molecular Alteration | Number of patients |
|---|---|---|
| NSCLC | ALK rearrangement | |
| | ROS1 6 rearrangements | 8* |
| | 1 deletion | 8 |
| | 1 copy number gain | |
| CRC | TrkA rearrangement | 1 |
| | ROS1 deletion | 1 |
| Neuroblastoma | ALK mutation | 2 |
| | ROS1 rearrangement | 1 |
| | TrkA overexpression | 1 |
| Glioblastoma | None** | 1 |
| Pancreatic | ROS1 deletion | 1 |
| Leiomyosarcoma | ALK deletion | 1 |

Steady state pK profile of N-[5-(3,5-difluorobenzyl)-1H-indazol-3-yl]-4-(4-methyl-piperazin-1-yl)-2-(tetrahydro-2H-pyran-4-ylamino) benzamide in patients on dosing Schedule A is depicted in the FIGURE.

Exposure to N-[5-(3,5-difluorobenzyl)-1H-indazol-3-yl]-4-(4-methyl -piperazin-1-yl)-2-(tetrahydro-2H-pyran-4-ylamino) benzamide in patients on dosing Schedule A increased in an approximate dose proportional manner up to doses of 800 mg/m$^2$. The mean plasma half-life was 17-44 hours following administration. The most common adverse events (AEs) (mainly grade 1-2) considered possibly treatment-related included nausea, paresthesia, vomiting, diarrhea, asthenia, myalgia, arthralgia, and dysgeusia. There was one possibly treatment-related grade 3 AE of asthenia.

| Adverse Event | G1 (%) | G2 (%) | Total (%)** |
|---|---|---|---|
| Nausea | 14 (56) | 2 (8) | 16 (64) |
| Paresthesia | 15 (60) | 0 (0) | 15 (60) |
| Asthenia | 9 (36) | 3 (12) | 13 (52) |
| Vomiting | 7 (28) | 2 (8) | 9 (36) |
| Diarrhea | 6 (24) | 2 (8) | 8 (32) |
| Myalgia | 6 (24) | 1 (4) | 7 (28) |
| Abdominal pain | 4 (16) | 2 (8) | 6 (24) |
| Back Pain | 5 (20) | 1 (4) | 6 (24) |
| Arthralgia | 3 (12) | 3 (12) | 6 (24) |
| Headache | 6 (24) | 0 (0) | 6 (24) |
| Dyspnea | 3 (12) | 1 (4) | 6 (24) |

| Adverse Event | G1 (%) | G2 (%) | Total (%)** |
|---|---|---|---|
| Pyrexia | 6 (24) | 0 (0) | 6 (24) |
| Dysgeusia | 6 (24) | 0 (0) | 6 (24) |
| Cough | 4 (16) | 1 (4) | 5 (20) |

Results

Non-small cell lung cancer (NSCLC) patients (N=4).

A 46 year old female, with a ROS1 rearrangement, s/p 2 cycles of chemotherapy, achieved complete response after 2 cycles of N-[5-(3,5-difluorobenzyl)-1H -indazol-3-yl]-4-(4-methyl-piperazin-1-yl)-2-(tetrahydro-2H-pyran-4-ylamino) benzamide (400 mg/m2/day, Schedule C). Complete response is ongoing (patient is currently in cycle 2).

A 63 year old female with metastatic adenocarcinoma, ALK rearrangement, s/p 4 cycles of chemotherapy, crizotinib, achieved partial response after 4 cycles of N-[5-(3,5-difluorobenzyl)-1H- indazol-3-yl]-4-(4-methy 1-piperazin-1-yl)-2-(tetrahydro-2H-pyran-4-ylamino) benzamide (1200 mg/m2/day, Schedule A). Partial response is ongoing (patient is currently in cycle 10).

A 44 year old female with metastatic disease (CNS metastases), ROS1 rearrangement, s/p 3 cycles of chemotherapy, erlotinib, s/p surgery/XRT to brain, achieved partial response after 2 cycles of N-[5-(3,5-difluorobenzyl)-1H-indazol-3-yl]-4-(4-methyl -piperazin-1-yl)-2-(tetrahydro-2H-pyran-4-ylamino) benzamide (1200 mg/m$^2$/day, Schedule A). The patient exhibited a partial response that is ongoing (patient currently in cycle 9).

A 63 year old male, ROS1 rearrangement, s/p 3 cycles of chemotherapy, achieved partial response after 1 cycle of N-[5-(3,5-difluorobenzyl)-1H-indazol-3-yl]-4-(4-methyl-piperazin-1-yl)-2-(tetrahydro-2H-pyran-4-ylamino) benzamide (400 mg/m2/day, Schedule C). Partial response is ongoing (patient currently in cycle 3).

Colorectal cancer (CRC) (N=1).

A 75 year old female with metastatic CRC, TrkA rearrangement, s/p 3 cycles of chemotherapy, cetuximab, achieved partial response after 1 cycle of N-[5-(3,5-difluorobenzyl)-1H-indazol-3-yl]-4-(4-methyl-piperazin-1-yl)-2-(tetrahydro-2H-pyran-4-ylamino) benzamide (1600 mg/m$^2$, Schedule A). Partial response lasted for 4 cycles before progressive disease.

Neuroblastoma (NB) (N=1).

A 22 year old female with metastatic NB, ALK mutation, s/p 4 cycles of chemotherapy, achieved partial response after 12 cycles of N-[5-(3,5-difluorobenzyl)-1H -indazol-3-yl]-4-(4-methyl-piperazin-1-yl)-2-(tetrahydro-2H-pyran-4-ylamino) benzamide (started at 200 mg/m$^2$/day and had subsequent dose escalations to1200 mg/m$^2$/day, Schedule A). Partial response is ongoing (the patient is currently in cycle 21).

A total of 25 patients were evaluated across 3 different dosing schedules in this trial of N-[5-(3,5-difluorobenzyl)-1H-indazol-3-yl]-4-(4-methyl-piperazin-1-yl)-2-(tetrahydro-2H-pyran-4-ylamino) benzamide.

There was a complete response in a patient with non-small cell lung cancer (NSCLC) with a ROS1 molecular alteration. There were 5 partial responses (3 of these durable >9 cycles) across multiple tumor types (NSCLC, CRC and NB) in patients with TrkA, ROS1, and ALK molecular alterations; moreover, there were 2 patients with prolonged stable disease (11+cycles) with NSCLC and pancreatic adenocarcinoma.

N-[5-(3,5-difluorobenzyl)-1H-indazol-3-yl]-4-(4-methyl-piperazin-1-yl)-2-(tetrahydro-2H-pyran-4-ylamino) benzamide was well tolerated in all dosing schedules tested, including intermittent and daily continuous administration.

Most common AEs (mainly grade 1-2) considered possibly drug-related were nausea, paresthesia, vomiting, diarrhea, asthenia, myalgia, arthralgia, and dysgeusia.

Only 1 possibly drug-related Grade >3 AE was observed: asthenia (Grade 3 in one patient).

No drug limiting toxicities, study discontinuations due to adverse events, or drug-related serious adverse events were reported.

Schedule A was terminated at 1600 mg/m2/day due to a plateau of N- [5-(3,5-difluorobenzyl)-1H-indazol-3-yl]-4-(4-methyl-piperazin-1-yl)-2-(tetrahydro-2H -pyran-4-ylamino) benzamide exposure and the data were presented previously.

N-[5-(3,5-difluorobenzyl)-1H-indazol-3-yl]-4-(4-methyl-piperazin-1-yl)-2-(tetrahydro-2H-pyran-4-ylamino) benzamide was well tolerated in all dosing schedules tested (both on an intermittent and daily continuous basis). Most AEs <Grade 2.

Only 1 possibly drug-related Grade >3 AE has been observed: asthenia (1200 mg/m$^2$, Schedule A), that subsided with dose reduction to 800 mg/m$^2$/day.

No DLTs, study discontinuations due to AEs, or drug-related SAEs were reported in any dosing schedule.

Exposure to N-[5-(3,5-difluorobenzyl)-1H-indazol-3-yl]-4-(4-methyl -piperazin-1-yl)-2-(tetrahydro-2H-pyran-4-ylamino) benzamide increased in an approximate dose proportional manner up to doses of 800 mg/m$^2$ with mean plasma half- life of 17 to 44 hours.

Responders tended to have higher exposure than non-responders throughout the entire dosing cycle in Schedule A.

The term "comprising" as used herein is synonymous with "including," "containing," or "characterized by," and is inclusive or open-ended and does not exclude additional, unrecited elements or method steps.

The term "wild-type" as used herein refers to the protein, nucleic acid sequence, allele, locus, or activity level of a protein in a disease-free cell of a healthy individual with respect to a disease in question. For example, a wild-type ROS1 activity level corresponds to an activity level of ROS1 in a healthy cell of an individual lacking a ROS1-related disease or pre-disease condition.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of inhibiting deregulated protein kinase activity in a neuroblastoma cell, wherein said deregulated protein kinase activity is one or more of tyrosine kinase ROS1, high affinity receptor tyrosine kinase TrkA, TrkB, or TrkC activity, the method comprising administering to said cell an effective amount of a compound as the sole active agent selected from the group consisting of N-[5-(3,5-difluorobenzyl)-1H-indazol-3-yl]-4-(piperazin-1-yl)-2-(tetrahydro-2H-pyran-4-ylamino) benzamide, N-[5-(3,5-difluorobenzyl)-1H-indazol-3-yl]-4-(4-methyl-piperazin-1-yl)-2-(tetrahydro-2H-pyran-4-ylamino) benzamide, N-[5-(3,5-difluoro-benzenesulfonyl)-1H-indazol-3-yl]-2-((R)-2-methoxy-1-methyl-ethylamino)-4-(4-methyl-piperazin-1-yl)benzamide, and a pharmaceutically acceptable salt thereof.

2. The method of claim 1, wherein the compound is N-[5-(3,5-difluorobenzyl)-1H-indazol-3-yl]-4-(piperazin-1-yl)-2-(tetrahydro-2H-pyran-4-ylamino) benzamide, or a pharmaceutically acceptable salt thereof.

3. The method of claim 1, wherein the compound is N-[5-(3,5-difluorobenzyl)-1H-indazol-3-yl]-4-(4-methyl-piperazin-1-yl)-2-(tetrahydro-2H-pyran-4-ylamino) benzamide, or a pharmaceutically acceptable salt thereof.

4. The method of claim 1, wherein the compound is N-[5-(3,5-difluoro -benzenesulfonyl)-1H-indazol-3-yl]-2-((R)-2-methoxy-1-methyl-ethylamino)-4-(4-methyl -piperazin-1-yl) benzamide, or a pharmaceutically acceptable salt thereof.

5. The method of claim 1, wherein said deregulated protein kinase activity is activity of ROS1.

6. The method of claim 1, wherein said deregulated protein kinase activity is activity of TrkA.

7. The method of claim 1, wherein said deregulated protein kinase activity is activity of TrkB.

8. The method of claim 1, wherein said deregulated protein kinase activity is activity of TrkC.

* * * * *